US012686870B2

(12) United States Patent 
Esashi

(10) Patent No.: US 12,686,870 B2 
(45) Date of Patent: Jul. 21, 2026

(54) TLR9 AGONISTS

(71) Applicant: SBI BIOTECH CO., LTD., Tokyo (JP)

(72) Inventor: Eiji Esashi, Tokyo (JP)

(73) Assignee: SBI Biotech Co., Ltd., Tokyo (JP)

( * ) Notice: Subject to any disclaimer, the term of this patent is extended or adjusted under 35 U.S.C. 154(b) by 951 days.

(21) Appl. No.: 17/787,687

(22) PCT Filed: Jan. 8, 2021

(86) PCT No.: PCT/JP2021/000543 
§ 371 (c)(1), 
(2) Date: Jun. 21, 2022

(87) PCT Pub. No.: WO2021/141121 
PCT Pub. Date: Jul. 15, 2021

(65) Prior Publication Data 
US 2023/0323368 A1     Oct. 12, 2023

(30) Foreign Application Priority Data

Jan. 10, 2020    (JP) ................................. 2020-002715

(51) Int. Cl.

| | |
|---|---|
| *C07H 21/02* | (2006.01) |
| *A61K 45/06* | (2006.01) |
| *A61P 1/00* | (2006.01) |
| *A61P 1/16* | (2006.01) |
| *A61P 11/00* | (2006.01) |
| *A61P 35/00* | (2006.01) |
| *A61P 35/02* | (2006.01) |
| *C12N 15/117* | (2010.01) |

(52) U.S. Cl. 
CPC ............ *C12N 15/117* (2013.01); *A61K 45/06* (2013.01); *A61P 1/00* (2018.01); *A61P 1/16* (2018.01); *A61P 11/00* (2018.01); *A61P 35/00* (2018.01); *A61P 35/02* (2018.01); *C12N 2310/17* (2013.01); *C12N 2310/315* (2013.01)

(58) Field of Classification Search 
CPC ........................ C12N 15/113; C12N 2310/141 
See application file for complete search history.

(56) References Cited

U.S. PATENT DOCUMENTS

| | | |
|---|---|---|
| 2005/0059619 A1 | 3/2005 | Krieg et al. |
| 2008/0305478 A1 | 12/2008 | Chun |
| 2009/0053148 A1 | 2/2009 | Kandimalla et al. |
| 2011/0136897 A1 | 6/2011 | Soreq et al. |
| 2012/0082700 A1 | 4/2012 | Dickey et al. |
| 2015/0299710 A1 | 10/2015 | Esashi et al. |
| 2016/0237493 A1 | 8/2016 | Brandon et al. |
| 2016/0346312 A1 | 12/2016 | Guiducci et al. |
| 2017/0326232 A1 | 11/2017 | Guiducci et al. |
| 2018/0169229 A1 | 6/2018 | Yu et al. |
| 2019/0269773 A1 | 9/2019 | Dickey et al. |

FOREIGN PATENT DOCUMENTS

| | | |
|---|---|---|
| JP | 5011520 | 8/2012 |
| RU | 2400538 | 9/2010 |
| WO | WO 2004/016805 | 2/2004 |
| WO | WO 2009/023819 | 2/2009 |
| WO | WO 2010/111485 | 9/2010 |
| WO | WO 2014/082254 | 6/2014 |
| WO | WO 2014/201516 | 12/2014 |
| WO | WO 2016/196173 | 12/2016 |
| WO | WO 2017/181128 | 10/2017 |
| WO | WO 2018/087699 | 5/2018 |

OTHER PUBLICATIONS

Karapetyan et al. (OncoTargets and Therapy 2020:13, 10039-10060).*

Mohamed et al. (Digestive Diseases and Sciences (2022) 67:1806-1821).*

Badri et al., "Optimization of radiation dosing schedules for proneural glioblastoma," J. Math. Bio, 2016, 72(5):1301-1336.

Baylot et al., "TCTP Has a Crucial Role in the Different Stages of Prostate Cancer Malignant Progression," Results Probl. Cell Differ., 2017, Chapter 13, 64:255-261.

Office Action in Japanese Patent Application No. 2022-534852, dated May 7, 2024, 9 pages (with English Machine Translation).

Office Action in Russian Patent Application No. 2022121544, dated Jun. 26, 2024, 18 pages (with English Translation).

[No. Author Listed], "Warming 'Cold' Melanoma with TLR9 Agonists," Cancer Discovery, 2018, 8(6):670.

Aarts et al., "Cryoablation and immunotherapy: an overview of evidence on its synergy," Insights into Imaging, 2019, 10:53.

Bauer et al., "Human TLR9 confers responsiveness to bacterial DNA via species-specific CpG motif recognition," Proc. Natl. Acad. Sci. U.S.A., 2001, 98(16):9237-9242.

Bedognetti et al., "Toward a comprehensive view of cancer immune responsiveness: a synopsis from the SITC workshop, " Journal for ImmunoTherapy of Cancer, 2019, 7:131 (with Published Correction).

Bhan et al., "TLR9 is required for protective innate immunity in Gram-negative bacterial pneumonia: role of dendritic cells, " J. Immunol., 2007, 179(6):3937-3946.

Bode et al., "Human plasmacytoid dendritic cells elicit a Type I Interferon response by sensing DNA via the cGAS-STING signaling pathway," Eur. J. Immunol., 2016, 46(7):1615-1621.

Chang et al., "Immune mechanism of the antitumor effects generated by bortezomib," J. Immunol., 2012, 189(6):3209-3220.

Charlebois et al., "PolyI:C and CpG Synergize with Anti-ErbB2 mAb for Treatment of Breast Tumors Resistant to Immune Checkpoint Inhibitors," Cancer Research, 2017, 77(2):312-319.

(Continued)

*Primary Examiner* — Amy Rose Hudson 
(74) *Attorney, Agent, or Firm* — Fish & Richardson P.C.

(57) ABSTRACT

The present application provides novel oligonucleotides and therapeutic use thereof. The oligonucleotides of the present invention can be used for the activation or modulation of immunity in the subject.

7 Claims, 41 Drawing Sheets

Specification includes a Sequence Listing.

(56)             References Cited

OTHER PUBLICATIONS

Davola et al., "Oncolytic viruses: how 'lytic' must they be for therapeutic efficacy?" Oncoimmunology, 2019, 8(6):e1596006.

Di Domizio et al., "TLR7 stimulation in human plasmacytoid dendritic cells leads to the induction of early IFN-inducible genes in the absence of type I IFN," Blood, 2009, 114(9):1794-1802.

Ding et al., "Targeting Myeloid Cells in Combination Treatments for Glioma and Other Tumors," Frontiers in Immunology, 2019, 10:1715.

Friedberg et al., "Combination immunotherapy with a CpG oligonucleotide (1018 ISS) and rituximab in patients with non-Hodgkin lymphoma: increased interferon-α/ß-inducible gene expression, without significant toxicity, " Blood, 2005, 105(2):489-495.

Gabrilovich, "Myeloid-Derived Suppressor Cells," Cancer Immunology Research, 2017, 5(1):3-8.

Galluzzi et al., "Immunogenic cell death in cancer and infectious disease," Nat. Rev. Immunol., 2017, 17:97-111.

GenBank Accession No. AM162613, "Leptospira biflexa serovar Patoc LEBIa1094 gene for putative ferric uptake regulation protein," dated Nov. 2, 2006, 1 page.

GenBank Accession No. FJ886804, "Sepsis cynipsea clone SC_K55 microsatellite sequence," dated Oct. 16, 2009, 1 page.

Greminger et al., "Development of polymorphic microsatellite markers for the drug fly (Sepsis cynipsea)," Molecular Ecology Resources, 2009, 9(6):1554-1556.

Harrington et al., "Optimizing oncolytic virotherapy in cancer treatment," Nat. Rev. Drug Discov., 2019, 18:689-706.

Hartmann et al., "Mechanism and function of a newly identified CpG DNA motif in human primary B cells," J. Immunol., 2000, 164:944-953.

Hato et al., "Molecular pathways: the immunogenic effects of platinum-based chemotherapeutics," Clin. Cancer Res., 2014, 20(11):2831-2837.

Hemmi et al., "A Toll-like receptor recognizes bacterial DNA," Nature, 2000, 408:740-745.

Hiramatsu et al., "CpG oligodeoxynucleotides potentiate the anti-tumor activity of anti-BST2 antibody," Cancer Sci., 2015, 106(10):1474-1478.

Hollingsworth et al., "Turning the corner on therapeutic cancer vaccines," NPJ Vaccines, 2019, 4:7.

International Search Report in International Patent Application No. PCT/JP2021/000543, dated Mar. 30, 2021, 4 pages.

Iurescia et al., "Targeting Cytosolic Nucleic Acid-Sensing Pathways for Cancer Immunotherapies," Front. Immunol., 2018, 9:711.

Jahrsdörfer et al., "CpG oligodeoxynucleotides as immunotherapy in cancer," Author Manuscript, Update Cancer Ther., 2008, 3(1):27-32.

Jarry et al., "Treg depletion followed by intracerebral CpG-ODN injection induce brain tumor rejection," J. Neuroimmunol., 2014, 267:35-42.

Kasperkovitz et al., "Toll-like receptor 9 modulates macrophage antifungal effector function during innate recognition of Candida albicans and Saccharomyces cerevisiae," Infect. Immun., 2011, 79(12):4858-4867.

Kleinovink et al., "Photodynamic-Immune Checkpoint Therapy Eradicates Local and Distant Tumors by CD8+ T Cells, " Cancer Immunol. Res., 2017, 5(10):832-838.

Kline et al., "Toll-like receptor 9 activation with CpG oligodeoxynucleotides for asthma therapy," New Drugs and Targets for Asthma and COPD, 2010, 39:95-99.

Krieg, "Development of TLR9 agonists for cancer therapy," J. Clin. Invest., 2007, 117(5):1184-1194.

Krieg, "Therapeutic potential of Toll-like receptor 9 activation," Nat. Rev. Drug Discov., 2006, 5:471-484.

Lee, "The Balance of Th17 versus Treg Cells in Autoimmunity," Int. J. Mol. Sci., 2018, 19:730.

Liu et al., "Metabolic rewiring of macrophages by CpG potentiates clearance of cancer cells and overcomes tumor-expressed CD47-mediated 'don't-eat-me' signal," Author Manuscript, Nat. Immunol., 2019. 20(3):265-275.

Louvel et al., "Comparative and Functional Genomic Analyses of Iron Transport and Regulation in Leptospira spp.," Journal of Bacteriology, 2006, 188(22):7893-7904.

Maeda et al., "A novel plasmacytoid dendritic cell line, CAL-1, established from a patient with blastic natural killer cell lymphoma," Int. J. Hematol., 2005, 81:148-154.

Mantovani et al., "The interaction of anticancer therapies with tumor-associated macrophages," J. Exp. Med., 2015, 212(4):435-445.

Martinez-Quintanilla et al., "Oncolytic viruses: overcoming translational challenges," J. Clin. Invest., 2019, 129(4):1407-1418.

Narita et al., "Plasmacytoid dendritic cell leukemia with potent antigen-presenting ability," Acta Haematol., 2008, 120:91-99.

O'Donnell et al., "The Promise of Neoadjuvant Immunotherapy and Surgery for Cancer Treatment," Clin. Cancer. Res., 2019, 25(19):5743-5751.

Ohto et al., "Toll-like Receptor 9 Contains Two DNA Binding Sites that Function Cooperatively to Promote Receptor Dimerization and activation," Immunity, 2018, 48:649-658.

Ohue et al., "Regulatory T (Treg) cells in cancer: Can Treg cells be a new therapeutic target?" Cancer Sci., 2019, 110:2080-2089.

Pardoll, "The blockade of immune checkpoints in cancer immunotherapy," Author Manuscript, Nat. Rev. Cancer, 2012, 12(4):252-264.

Passardi et al., "Immune Checkpoints as a Target for Colorectal Cancer Treatment," Int. J. Mol. Sci., 2017, 18:E1324.

Patin et al., "Pattern recognition receptors in fungal immunity," Semin. Cell Dev. Biol., 2019, 89:24-33.

Pohar et al., "Phosphodiester backbone of the CpG motif within immunostimulatory oligodeoxynucleotides augments activation of Toll-like receptor 9," Sci. Rep., 2017, 7:14598.

Pohar et al., "Selectivity of Human TLR9 for Double CpG Motifs and Implications for the Recognition of Genomic DNA," J. Immunol., 2017, 198(5):2093-2104.

Puig et al., "Use of thermolytic protective groups to prevent G-tetrad formation in CpG ODN type D: structural studies and immunomodulatory activity in primates," Nucleic Acids Res., 2006, 34(22):6488-6495.

Raja et al., "Oncolytic virus immunotherapy: future prospects for oncology," J. Immuno Ther. Cancer, 2018, 6:140.

Ray et al., "A novel TLR-9 agonist C792 inhibits plasmacytoid dendritic cell-induced myeloma cell growth and enhance cytotoxicity of bortezomib," Author Manuscript, Leukemia, 2014, 28(8):1716-1724.

Reilley et al., "Phase 1 trial of TLR9 agonist lefitolimod in combination with CTLA-4 checkpoint inhibitor ipilimumab in advanced tumors," Journal of Clinical Oncology, 2019, 37(15_suppl):TPS2669.

Ribas et al., "SD-101 in Combination with Pembrolizumab in Advanced Melanoma: Results of a Phase Ib, Multicenter Study," Cancer Discov., 2018, 8(10):1250-1257.

Roda et al., "CpG-containing oligodeoxynucleotides act through TLR9 to enhance the NK cell cytokine response to antibody-coated tumor cells," J. Immunol., 2005. 175(3):1619-1627.

Sargent et al., "Defective mismatch repair as a predictive marker for lack of efficacy of fluorouracil- based adjuvant therapy in colon cancer," J. Clin. Oncol., 2010, 28(20):3219-3226.

Scheiermann et al., "Clinical evaluation of CpG oligonucleotides as adjuvants for vaccines targeting infectious diseases and cancer," Author Manuscript, Vaccine, 2014, 32(48):6377-6389.

Schmitt et al., "The TLR9 agonist cobitolimod induces anti-inflammatory effects and balances the Th17/T-reg cell response in ulcerative colitis," Abstract No. OP004, J. Crohns Colitis, Abstracts of the 13th Congress of ECCO—European Crohn's and Colitis Organisation, 2018, 12(Suppl 1):S003-S004.

Shi et al., "Differential involvement of Th1 and Th17 in pathogenic autoimmune processes triggered by different TLR ligands," J. Immunol., 2013, 191(1):415-423.

Shirota et al., "CpG Oligonucleotides as Cancer Vaccine Adjuvants," Vaccines, 2015, 3:390-407.

(56) References Cited

OTHER PUBLICATIONS

Shirota et al., "Intratumoral injection of CpG oligonucleotides induces the differentiation and reduces the immunosuppressive activity of myeloid-derived suppressor cells," J. Immunol., 2012, 188(4):1592-1599.

Sivanandam et al., "Oncolytic Viruses and Immune Checkpoint Inhibition: The Best of Both Worlds," Mol. Ther. Oncolytics., 2019, 13:93-106.

Spaner et al., "Toll-like receptor agonists in the treatment of chronic lymphocytic leukemia," Leukemia, 2007, 21:53-60.

Spisek et al., "Bortezomib enhances dendritic cell (DC)-mediated induction of immunity to human myeloma via exposure of cell surface heat shock protein 90 on dying tumor cells: therapeutic implications," Blood, 2007, 109(11):4839-4845.

Swiecki et al., "Unraveling the functions of plasmacytoid dendritic cells during viral infections, autoimmunity, and tolerance," Author Manuscript, Immunol. Rev., 2010, 234(1):142-162.

Temizoz et al., "TLR9 and STING agonists synergistically induce innate and adaptive type-II IFN," Eur. J. Immunol., 2015, 45:1159-1169.

Tigno-Aranjuez et al., "Encephalitogenicity of complete Freund's adjuvant relative to CpG is linked to induction of Th17 cells," J. Immunol., 2009, 183:5654-5661.

Wang et al., "A CpG oligodeoxynucleotide acts as a potent adjuvant for inactivated rabies virus vaccine," Vaccine, 2008, 26:1893-1901.

Wang et al., "Intratumoral injection of a CpG oligonucleotide reverts resistance to PD-1 blockade by expanding multifunctional CD8+ T cells," Proc. Natl. Acad. Sci. U.S.A., 2016, 113(46):E7240-E7249.

Weigel et al., "CpG oligodeoxynucleotides potentiate the antitumor effects of chemotherapy or tumor resection in an orthotopic murine model of rhabdomyosarcoma," Clin. Cancer Res., 2003, 9:3105-3114.

Winkler, "Oligonucleotide conjugates for therapeutic applications," Ther. Deliv., 2013, 4(7):791-809.

Xu et al., "CpG oligodeoxynucleotides enhance the efficacy of adoptive cell transfer using tumor infiltrating lymphocytes by modifying the Th1 polarization and local infiltration of Th17 cells," Clin. Dev. Immunol., 2010, 2010:410893.

Yang et al., "Tumor-associated macrophages: from basic research to clinical application," J. Hematol. Oncol., 2017, 10:58.

Zimmerman et al., "Post-traumatic anxiety associates with failure of the innate immune receptor TLR9 to evade the pro-inflammatory NFκB pathway," Transl. Psychiatry, 2012, 2:e78.

Extended European Search Report in European Patent Application No. 21738230.8, dated Dec. 21, 2023, 9 pages.

Vollmer et al., "Immunotherapeutic applications of CpG oligodeoxynucleotide TLR9 agonists," Advanced Drug Delivery Reviews, Mar. 28, 2009, 61(3):195-204.

Office Action in Australian Patent Application No. 2021206355, dated Mar. 17, 2026, 4 pages.

* cited by examiner

[Fig. 1A]
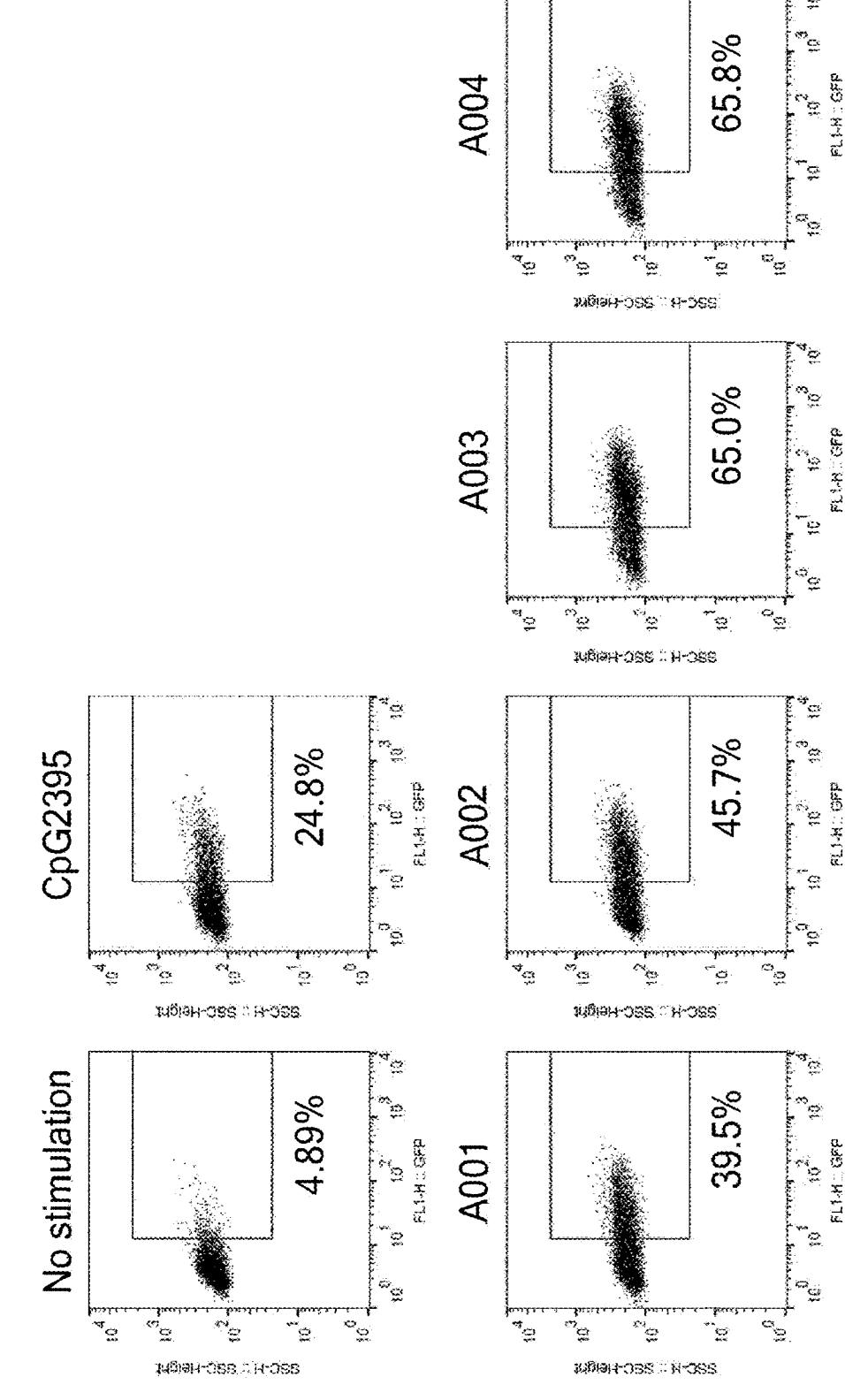

[Fig. 1B]
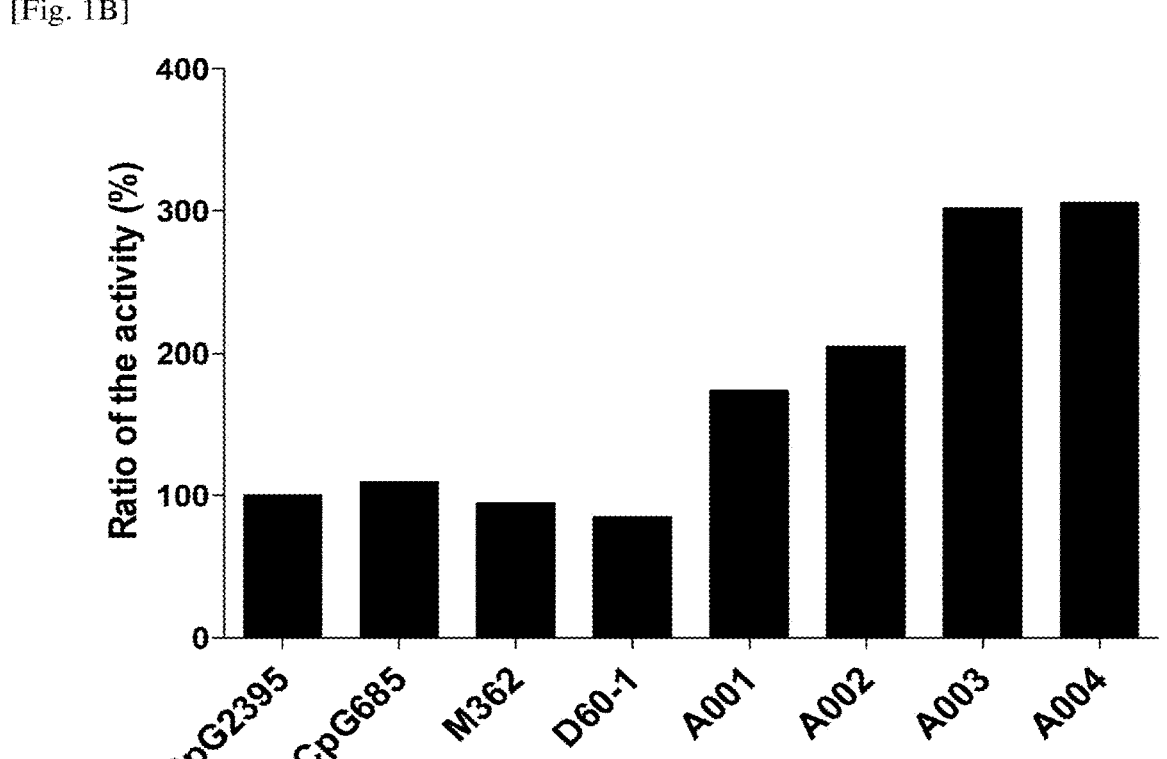

[Fig. 1C]
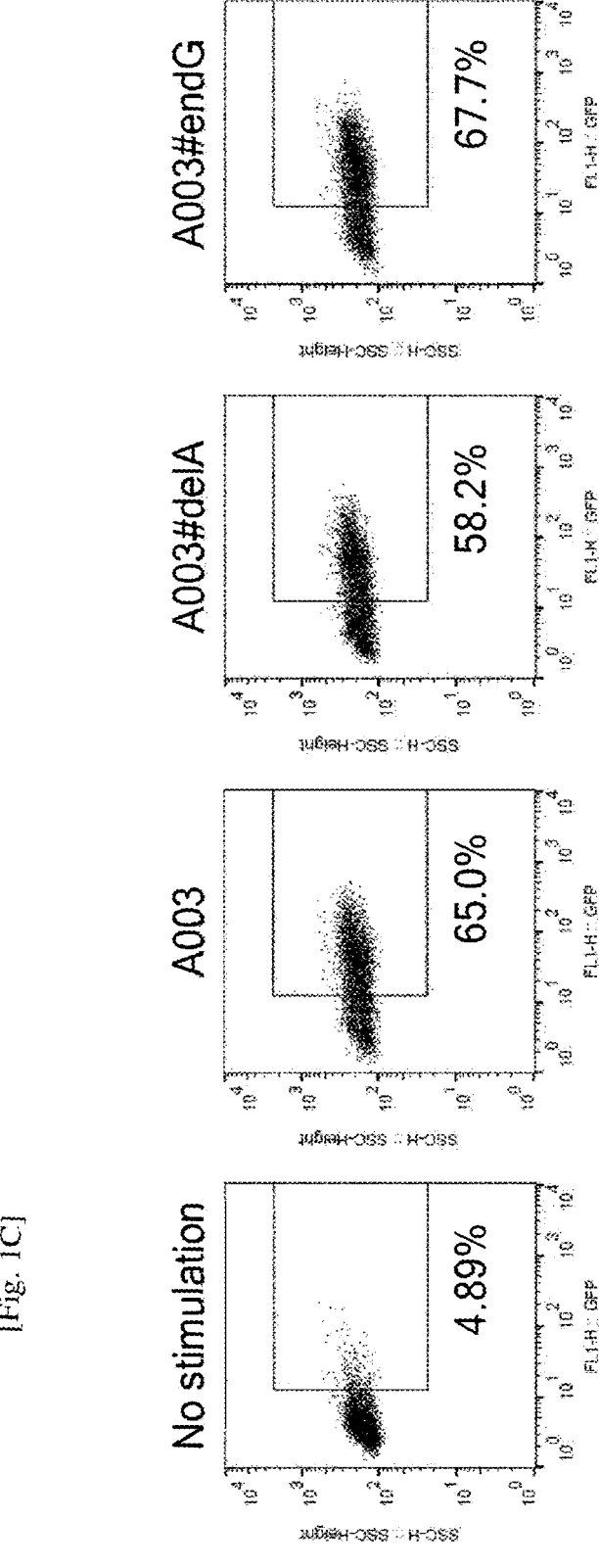

[Fig. 1D]
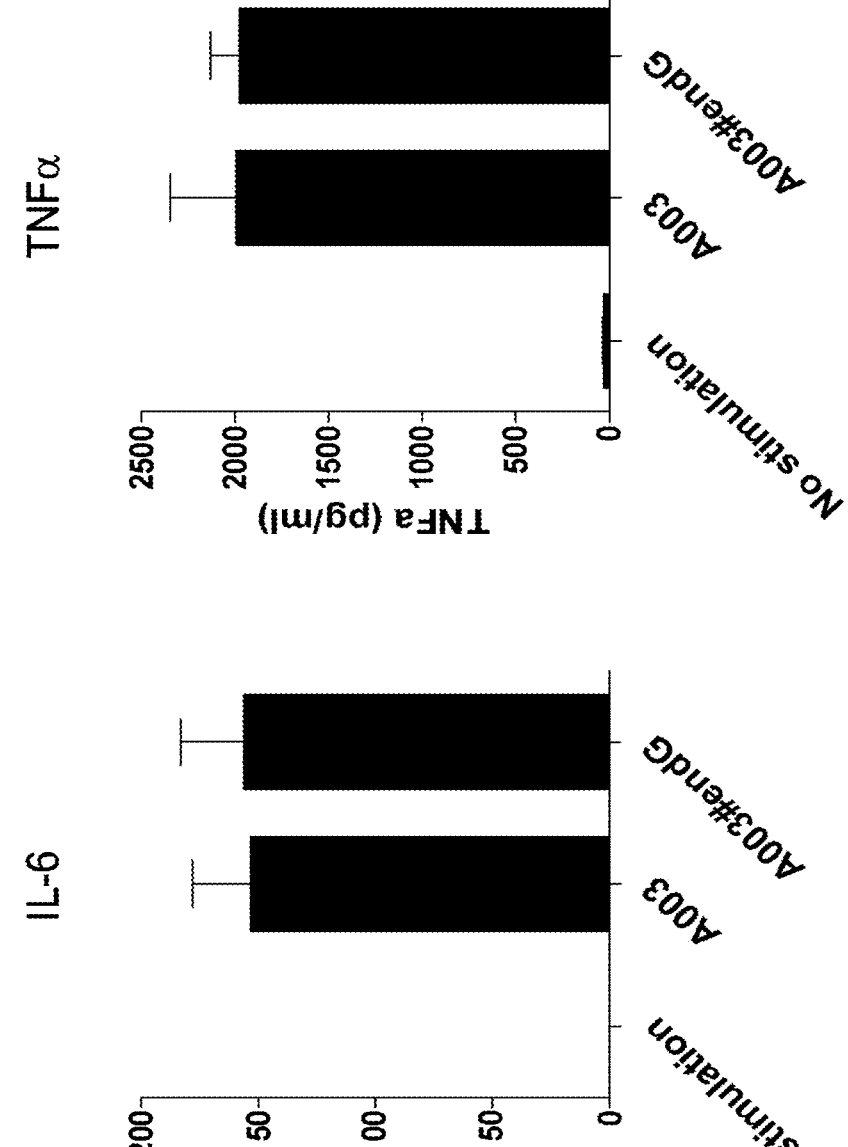

[Fig. 1E]
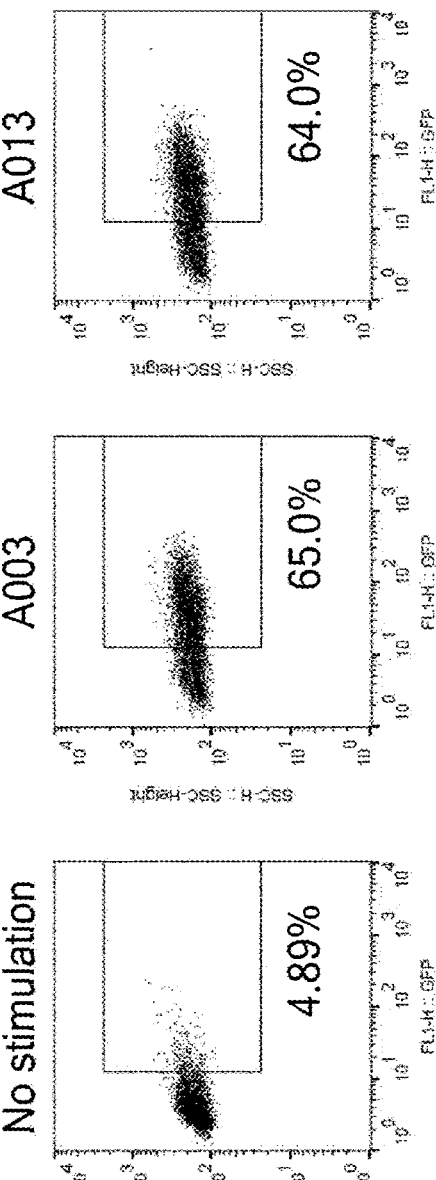

[Fig. 1F]
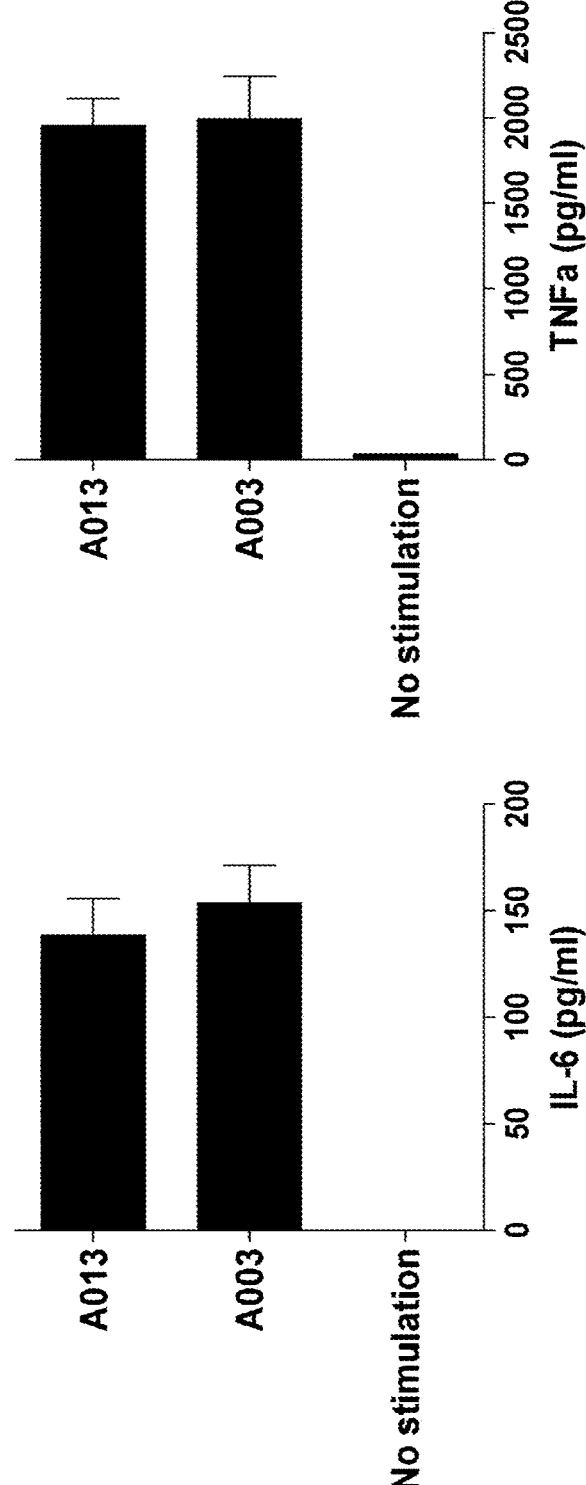

[Fig. 1G]
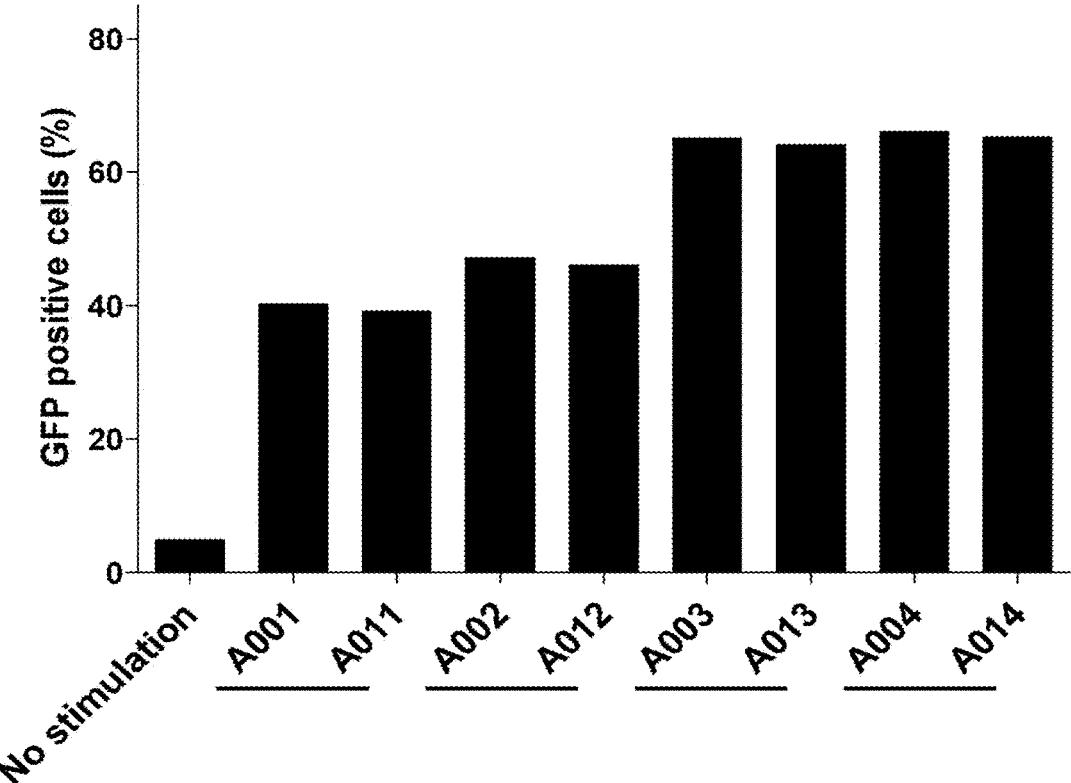
[Fig. 2A]
HEK/TLR7 cells
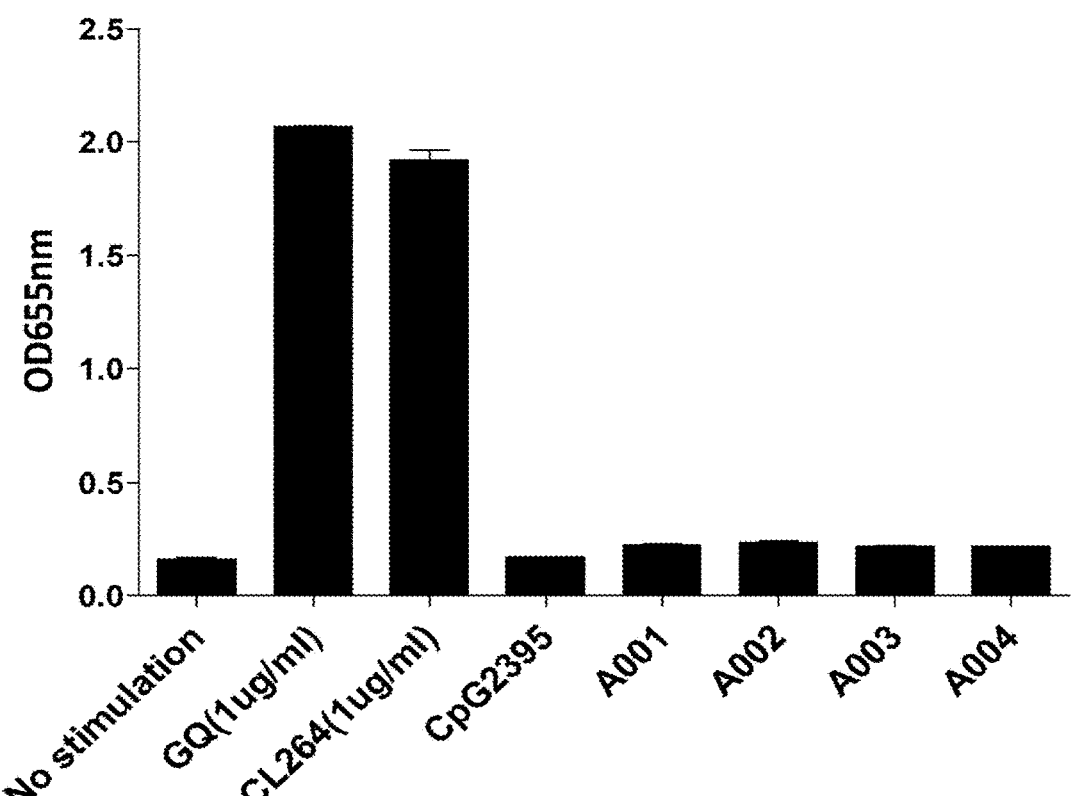

[Fig. 2B]
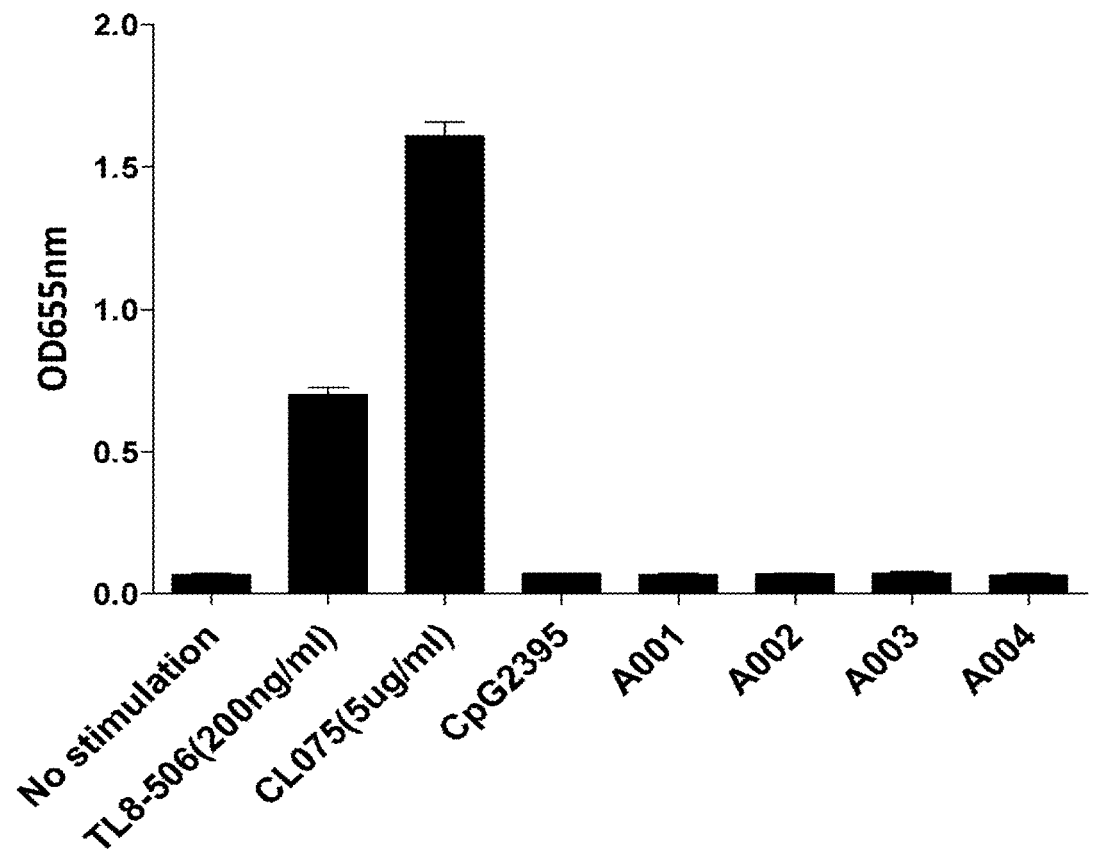
HEK/TLR8 cells

[Fig. 3A]
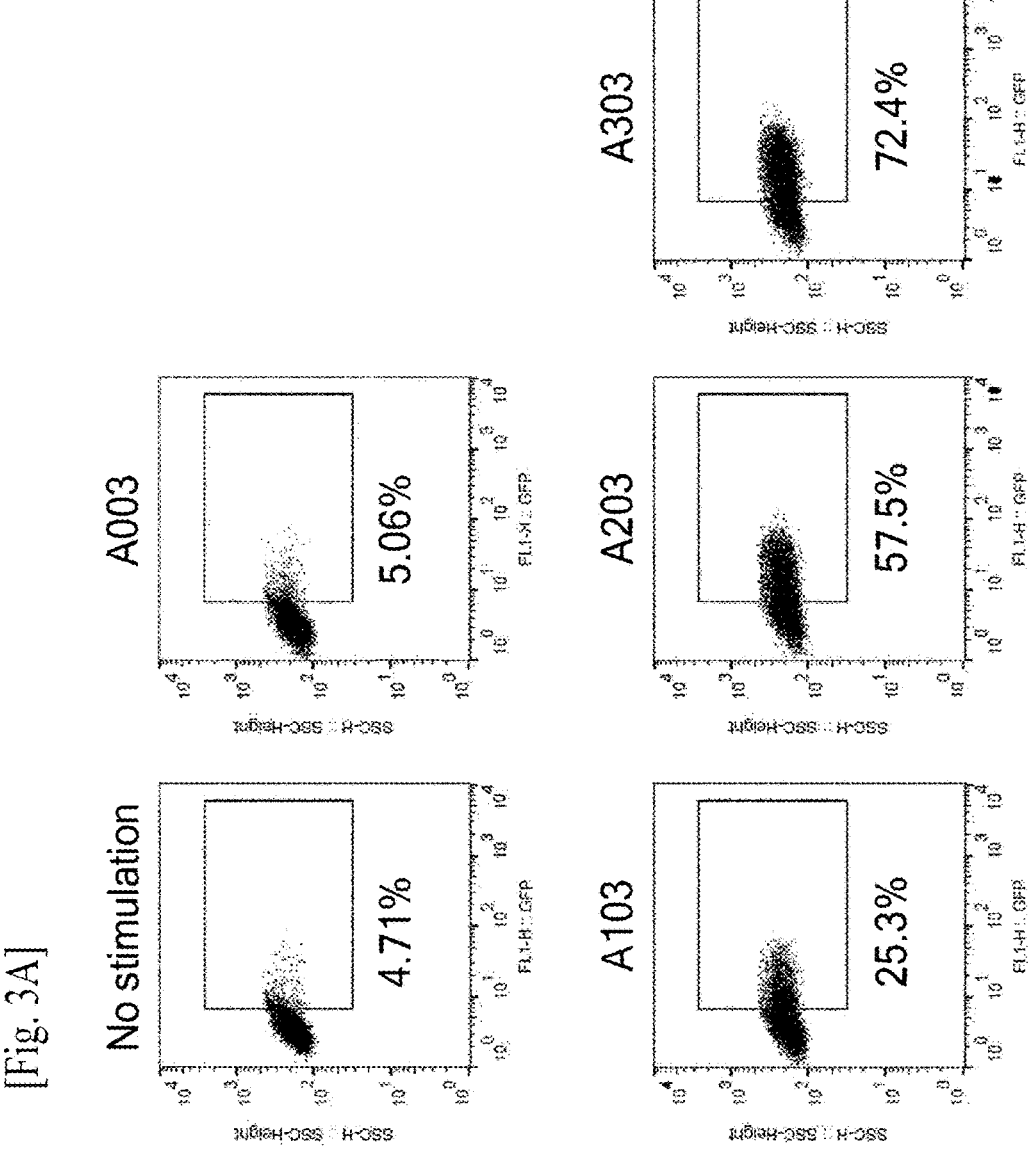

[Fig. 3B]
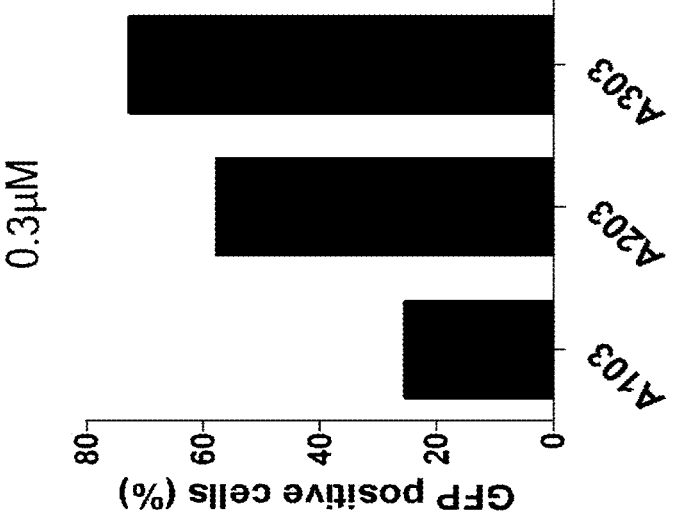
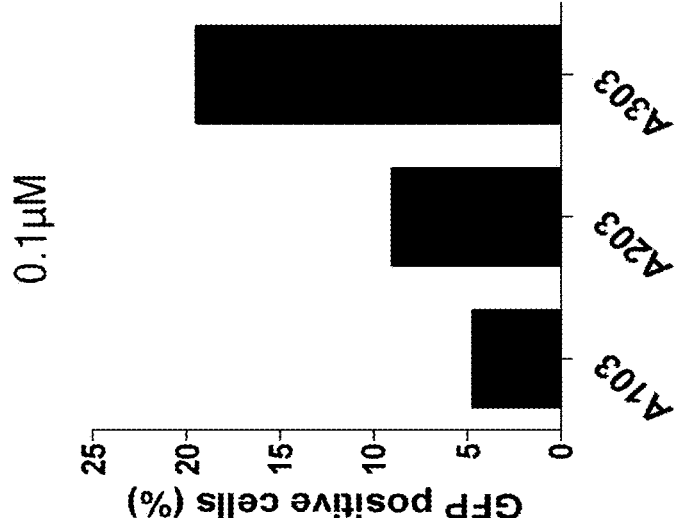

[Fig. 3C]
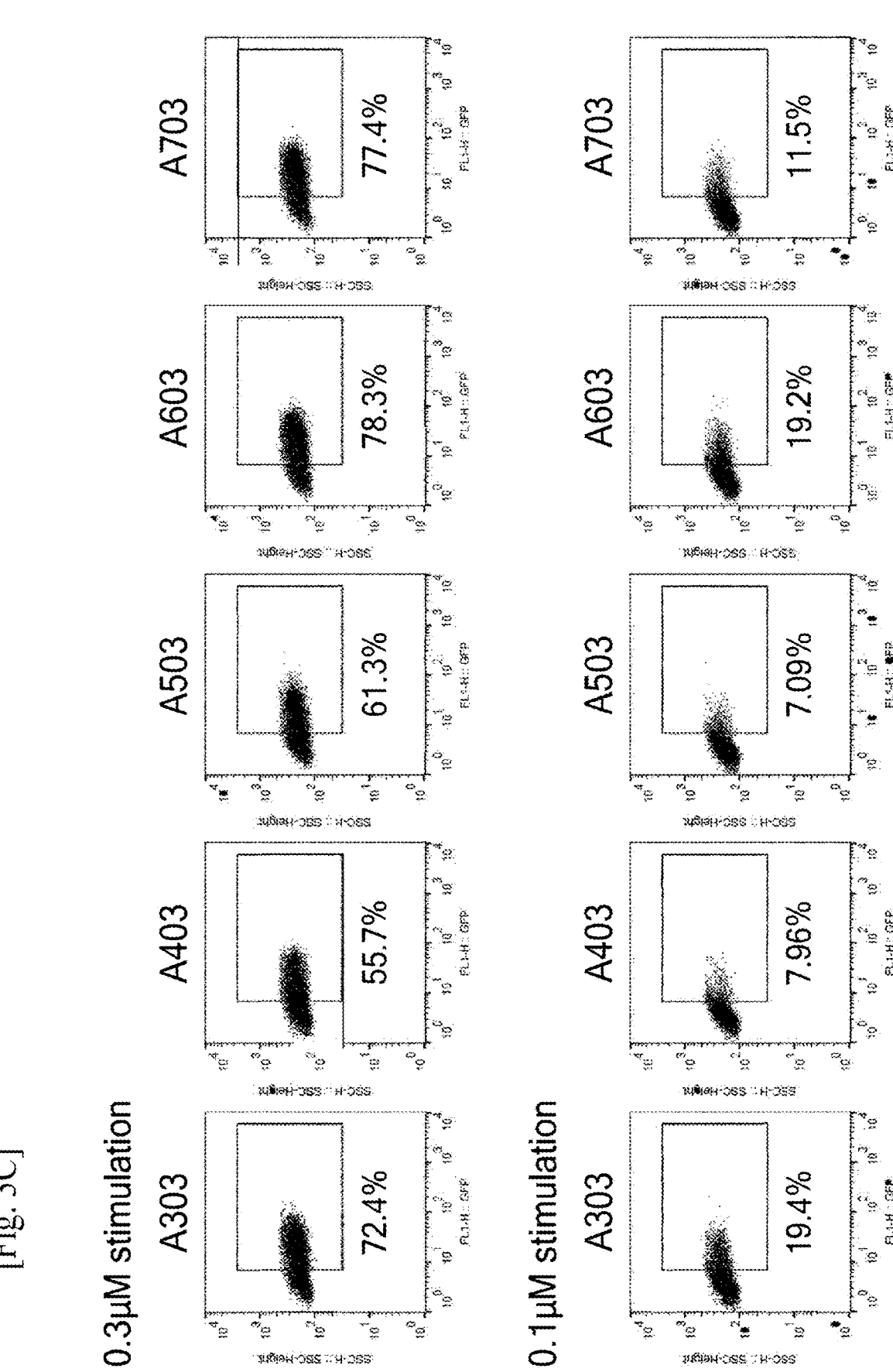

[Fig. 3D]
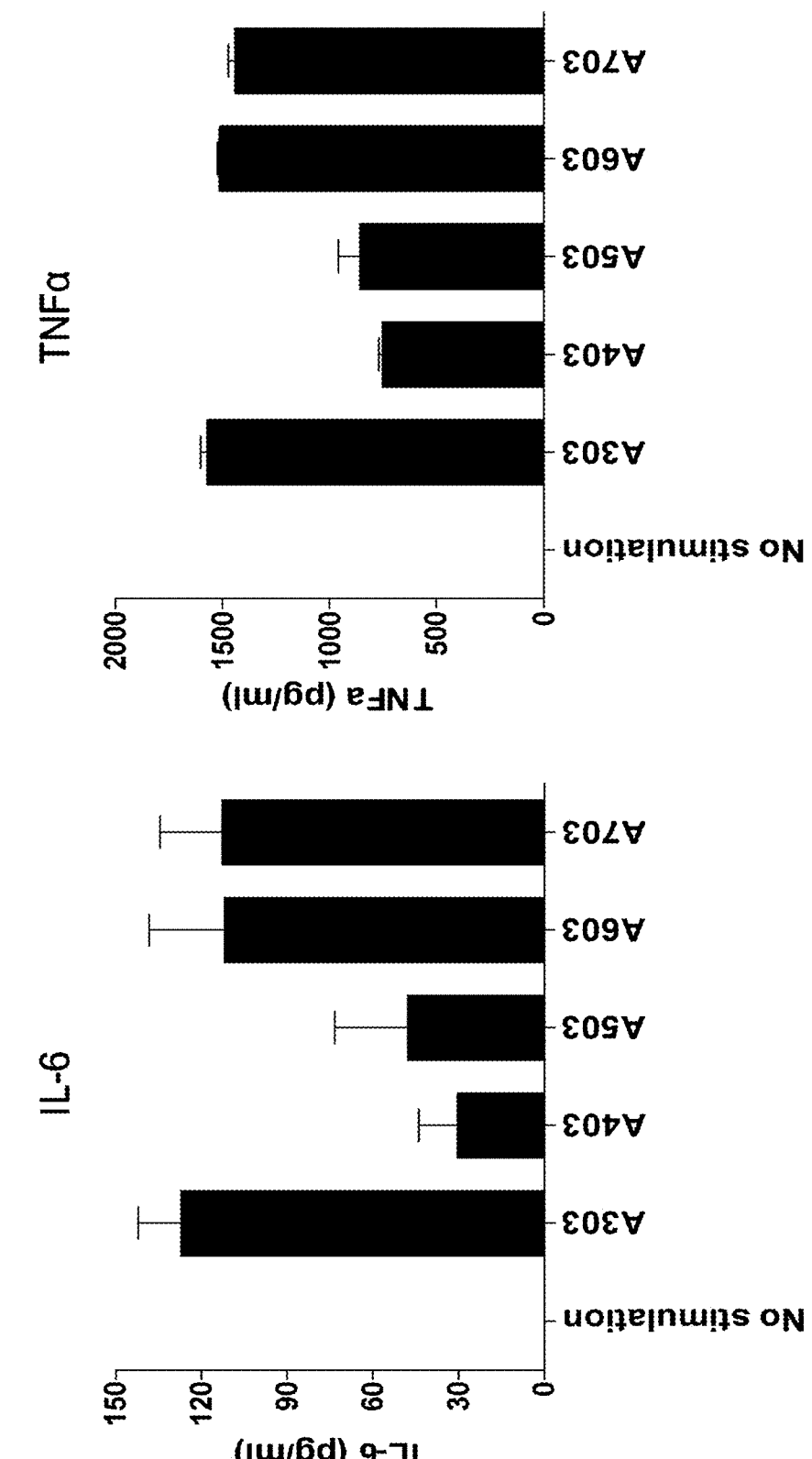

[Fig. 3E]
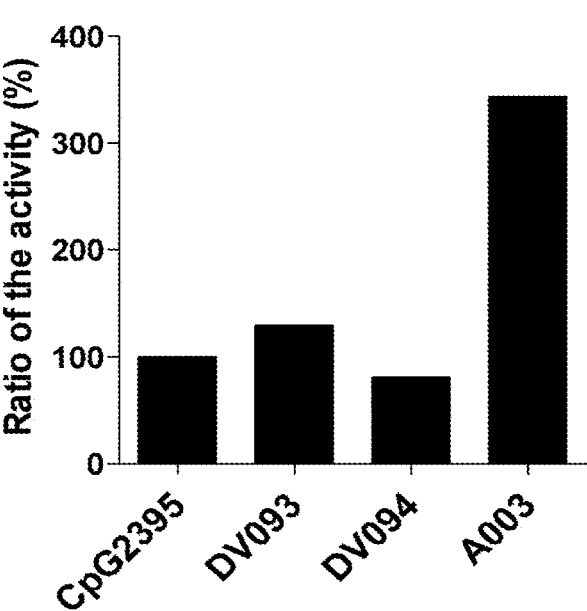

[Fig. 3F]
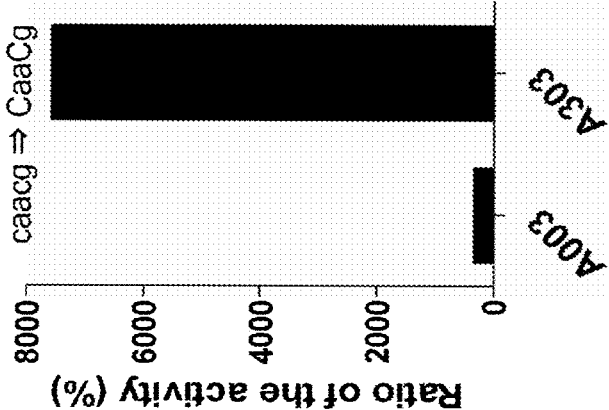
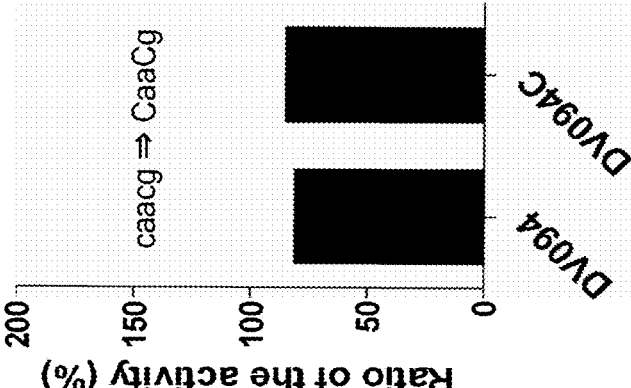
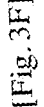
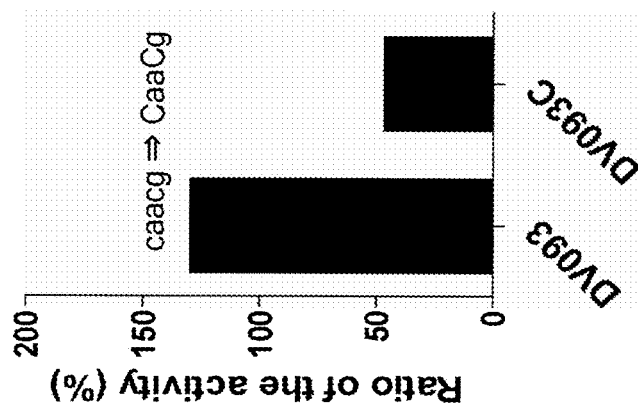

[Fig. 4A]
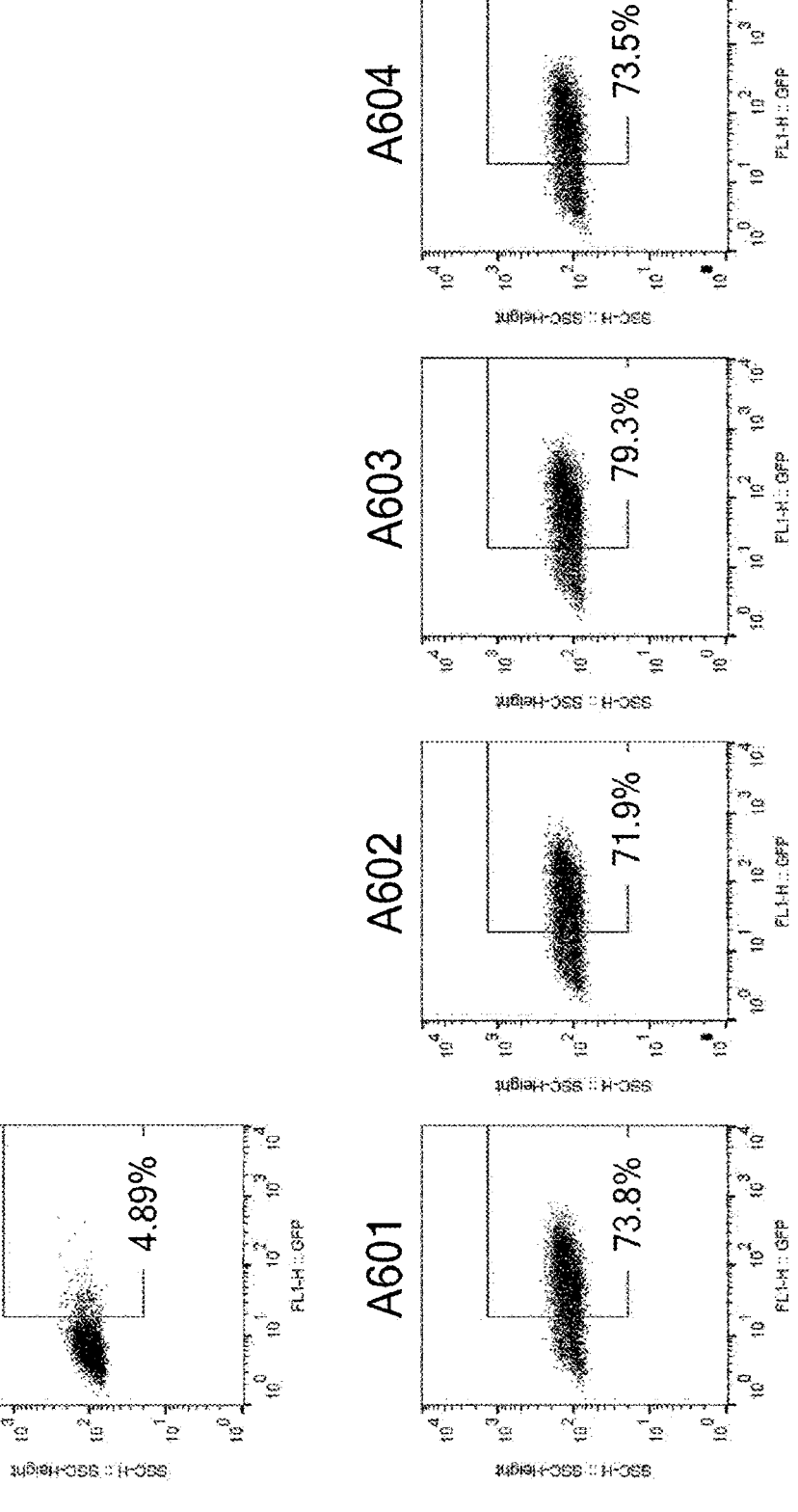

[Fig. 4B]
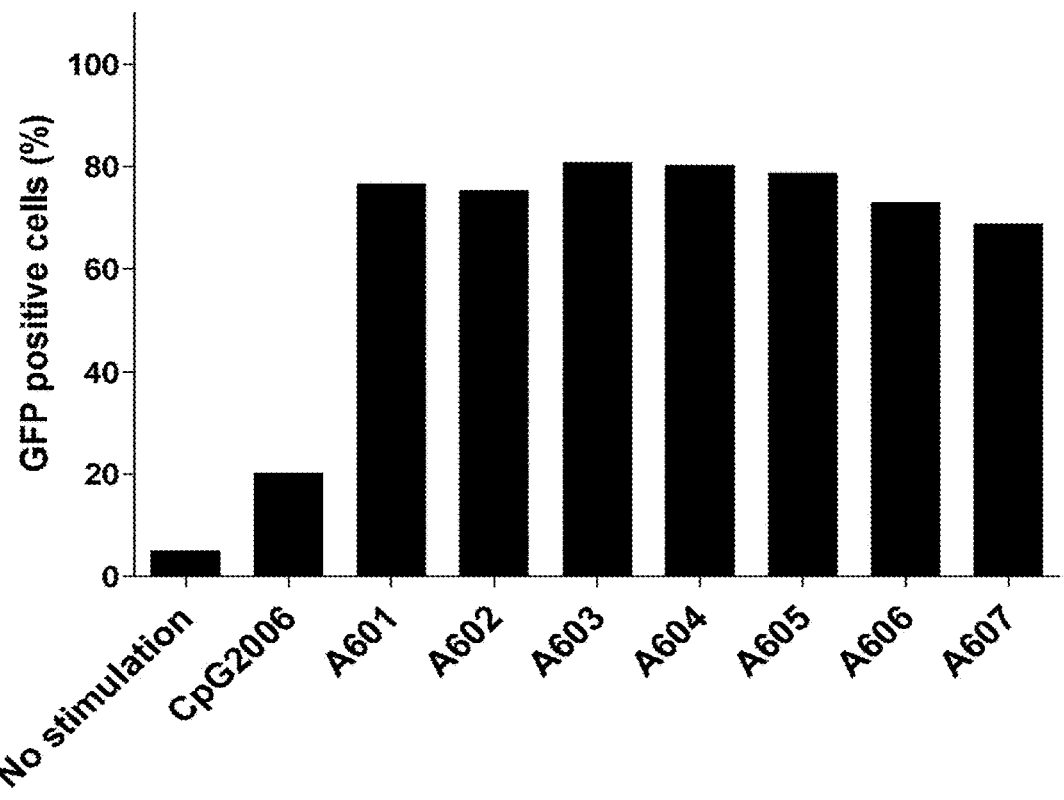
[Fig. 5A]
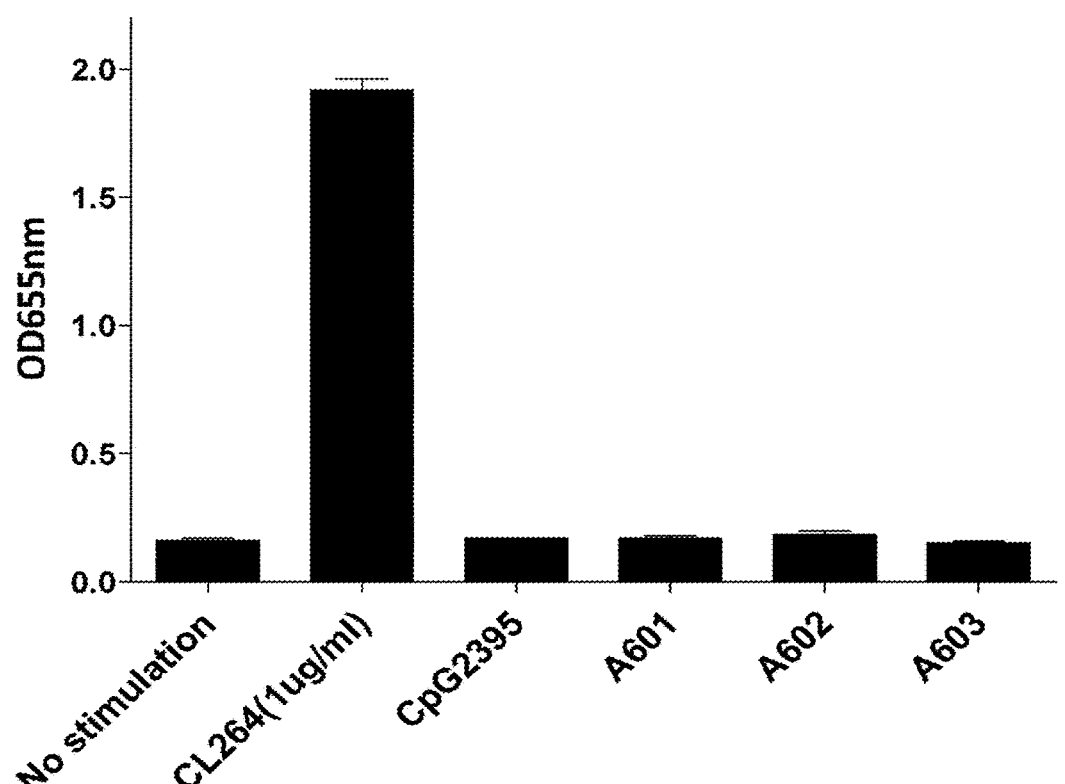

[Fig. 5B]
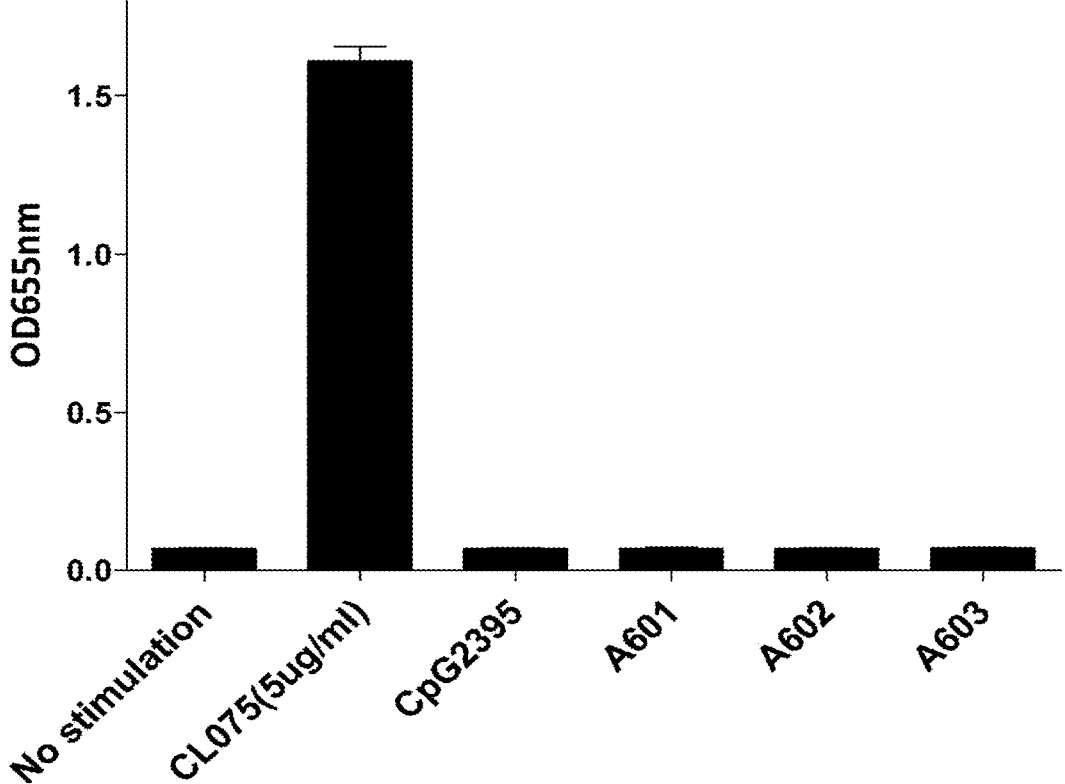

[Fig. 6A]
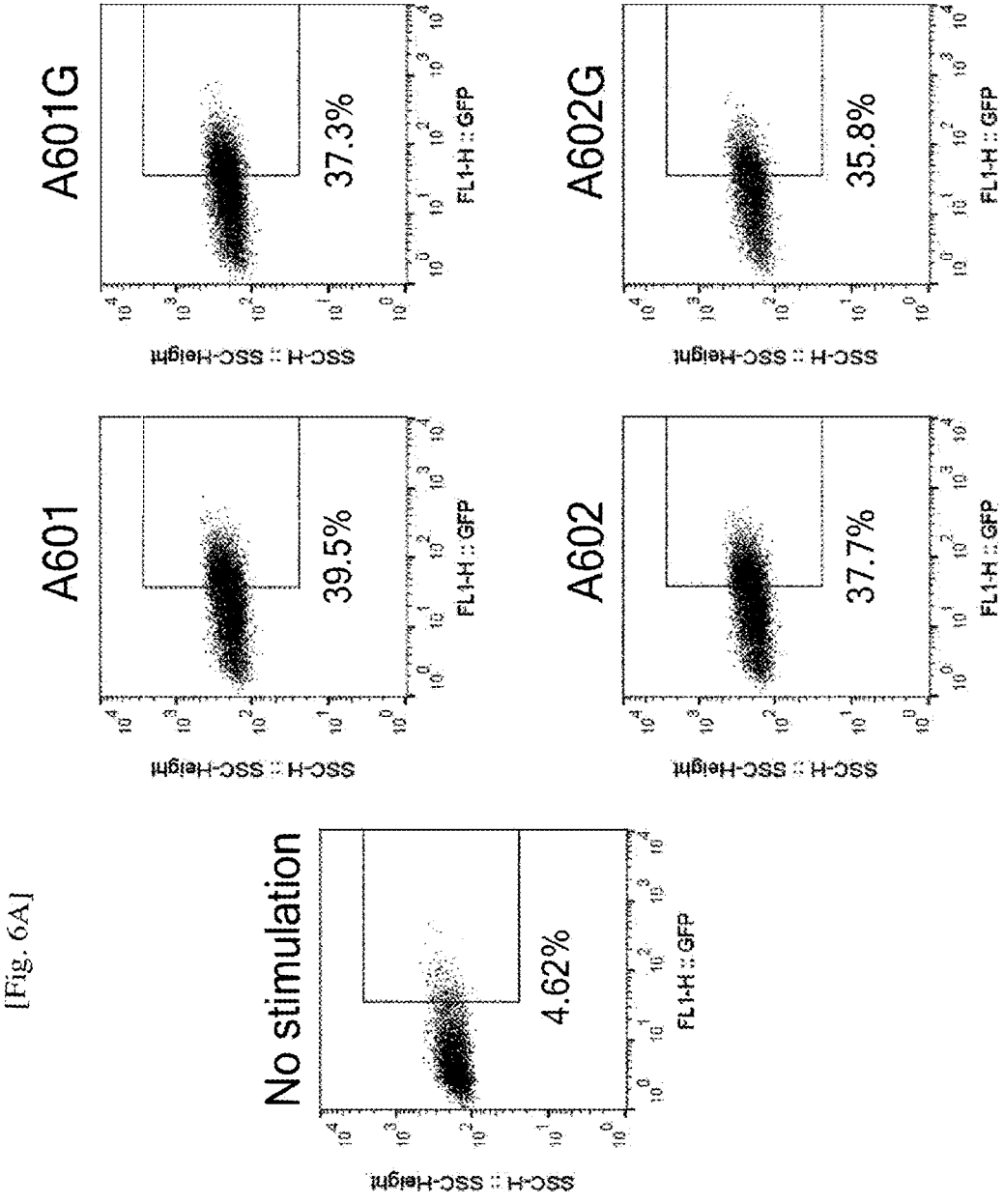

[Fig. 6B]
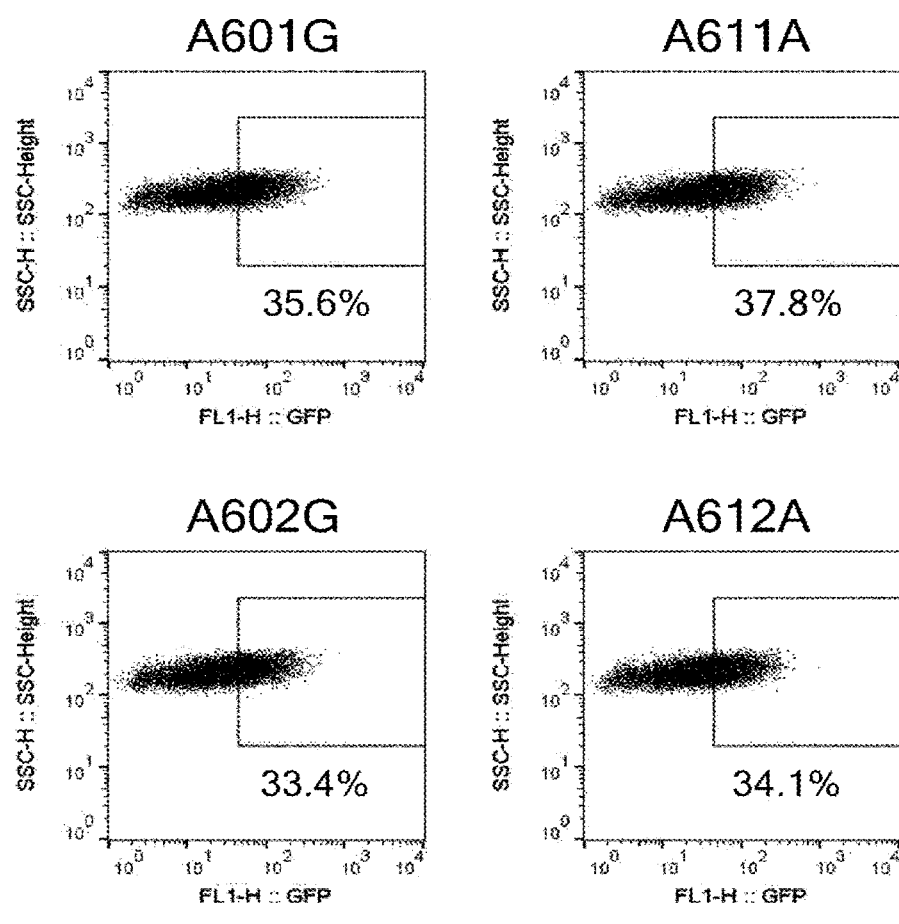

[Fig. 6C]
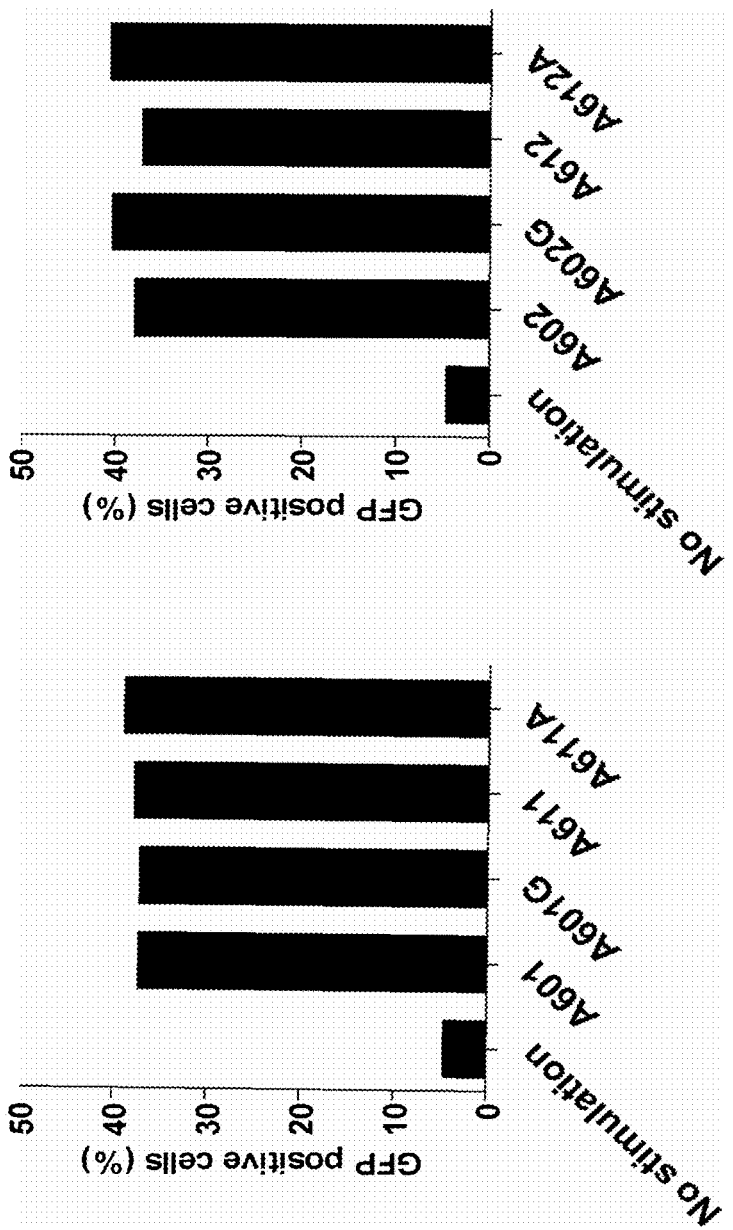

[Fig. 7A]
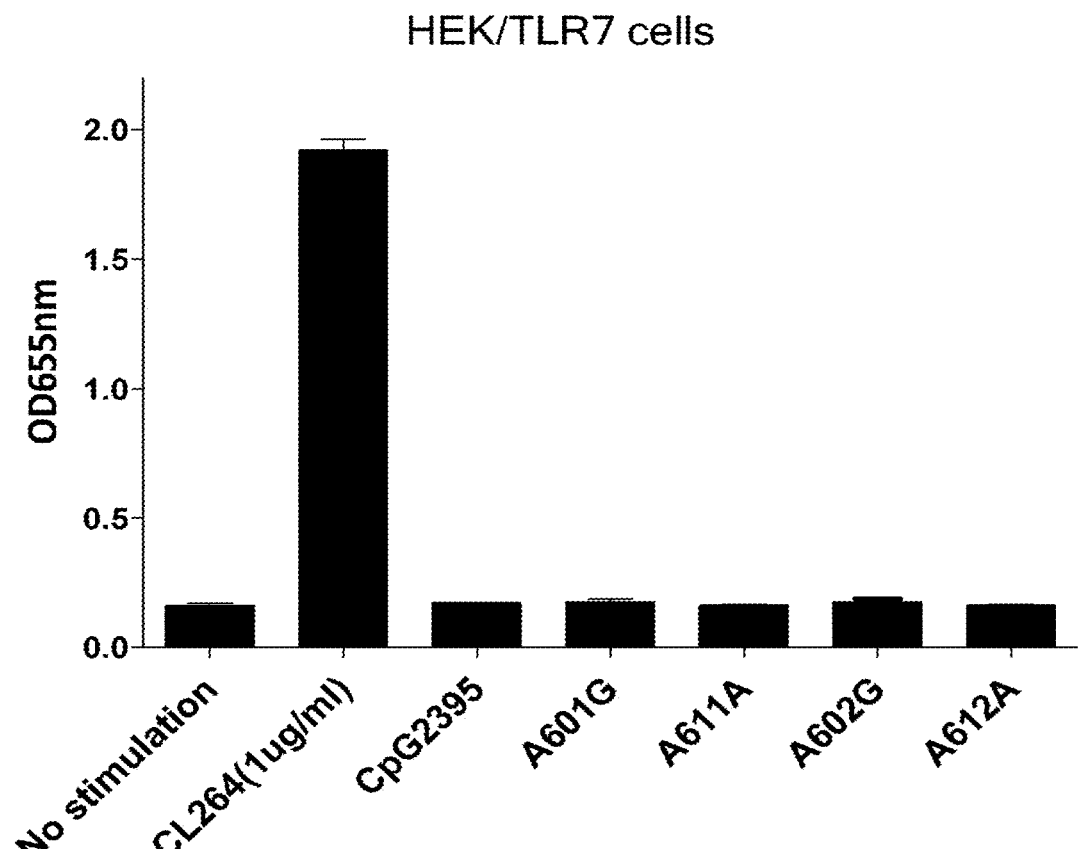

[Fig. 7B]
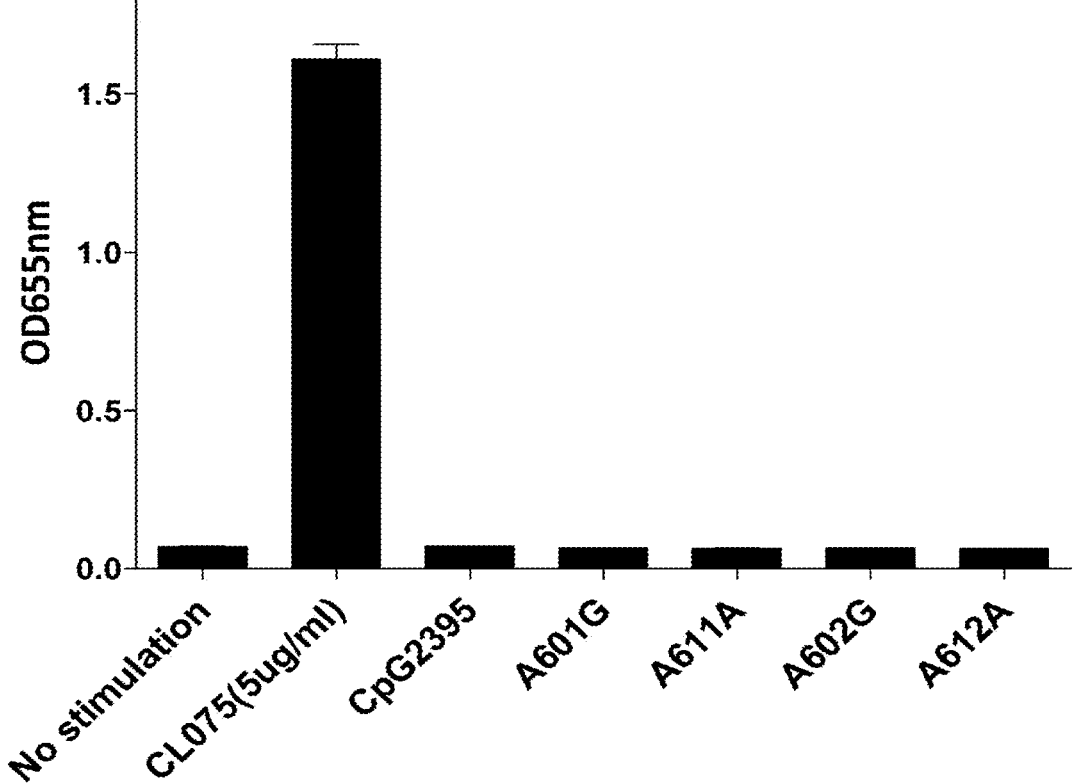
HEK/TLR8 cells

[Fig. 8A]
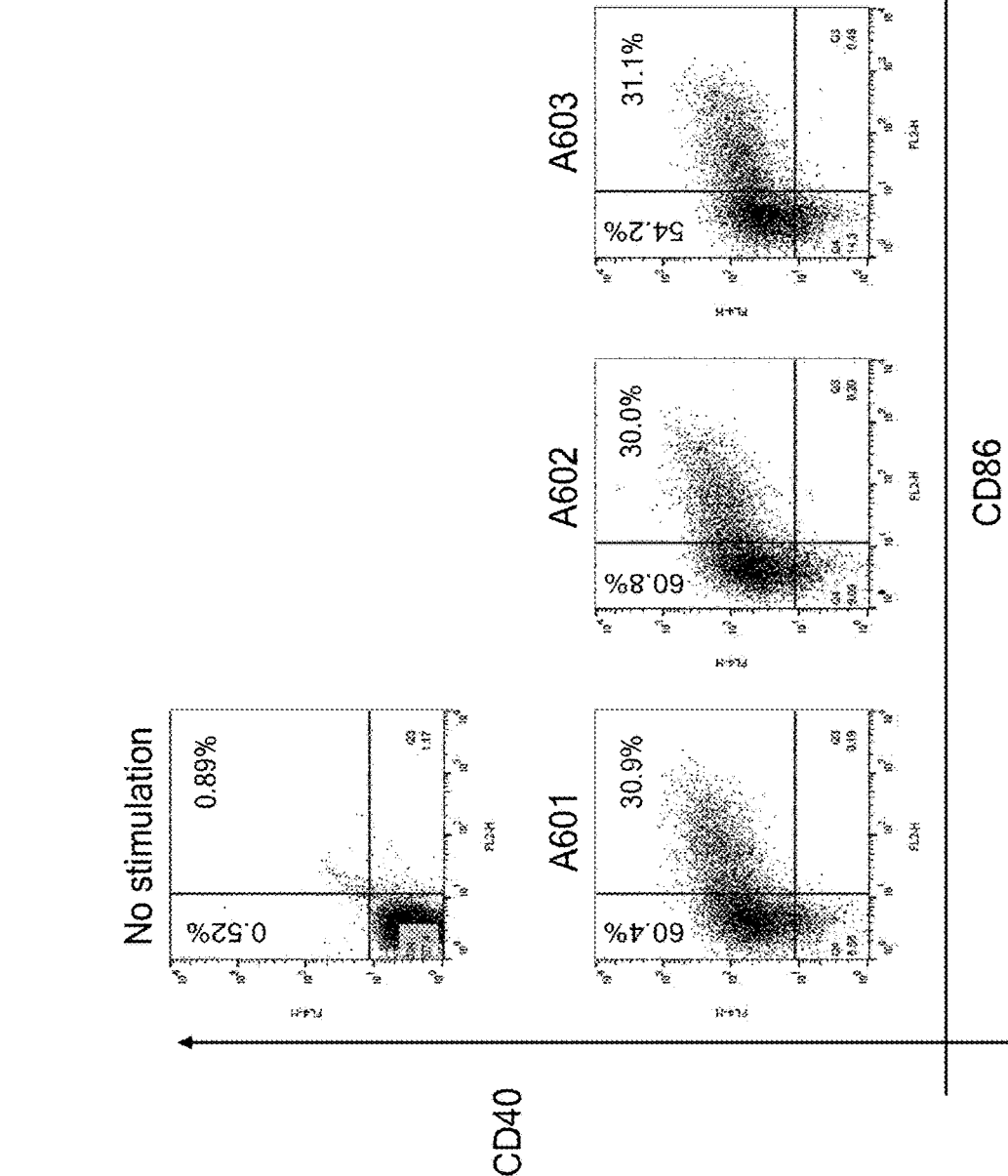

[Fig. 8B]
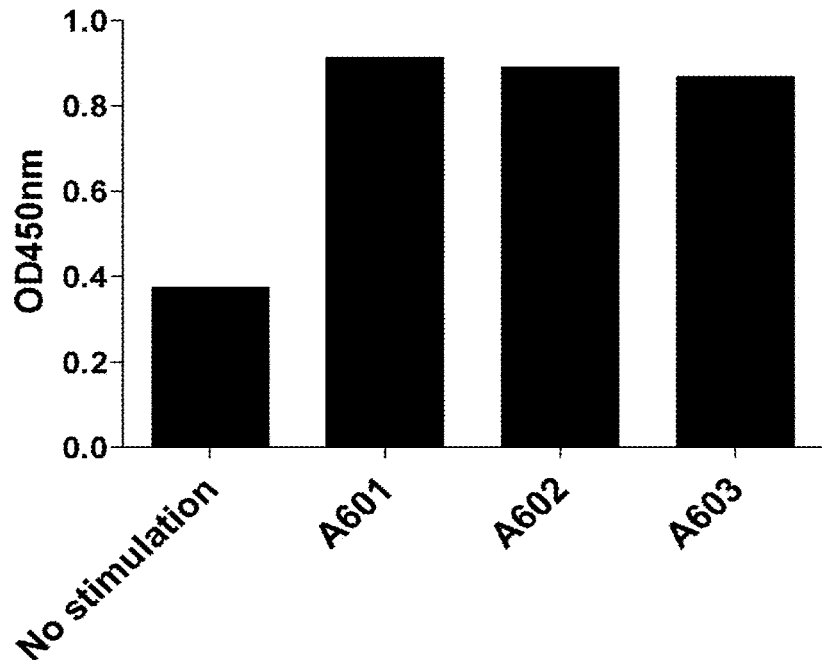

[Fig. 8C]
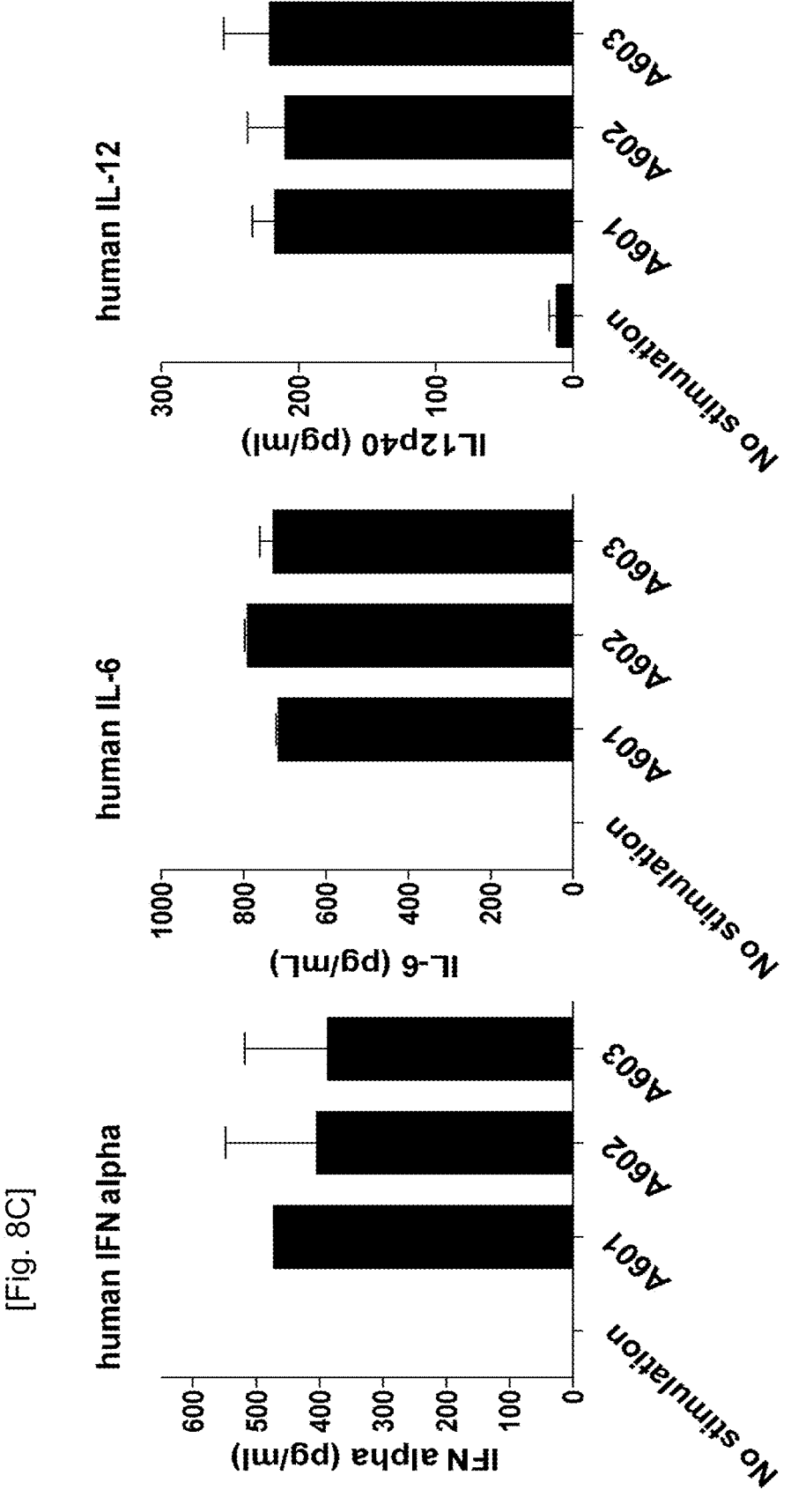

[Fig. 9A]
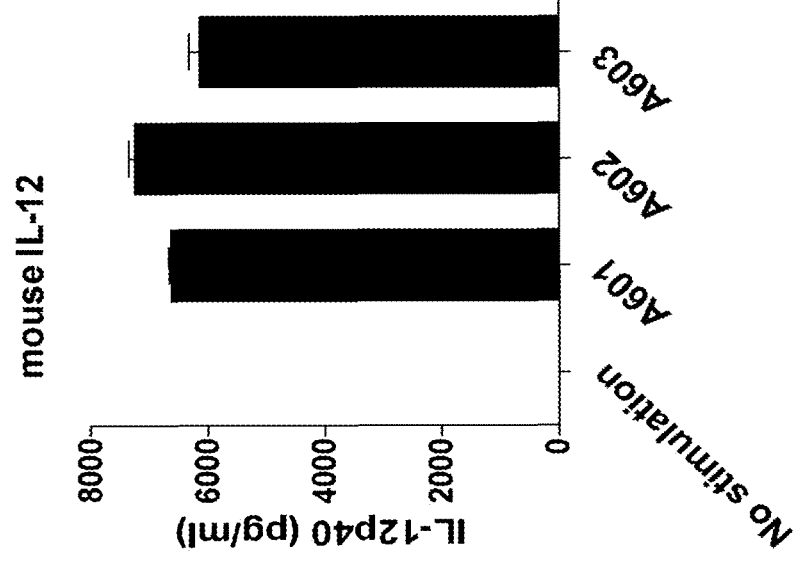
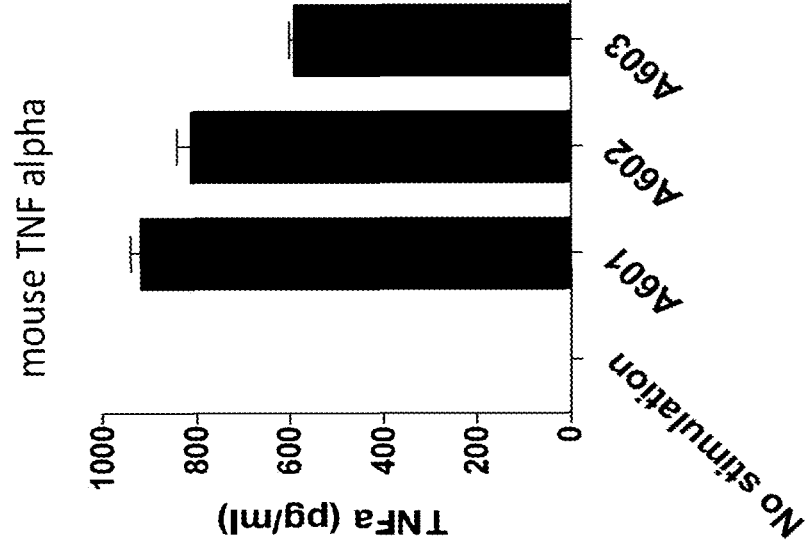

[Fig. 9B]
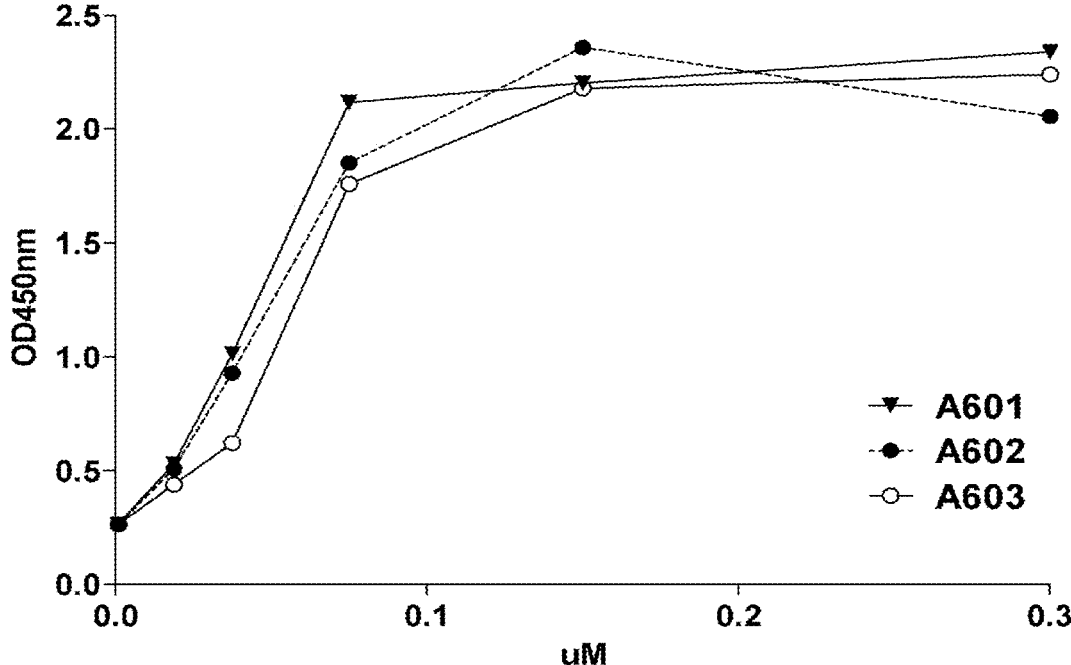
[Fig. 9C]
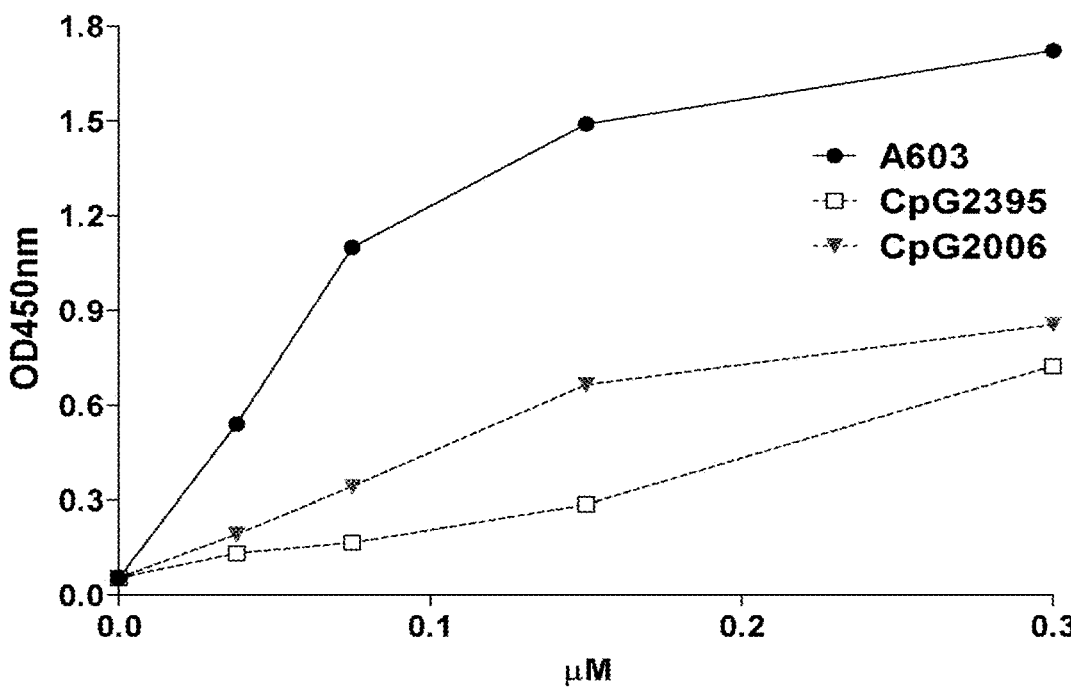

[Fig. 10A]
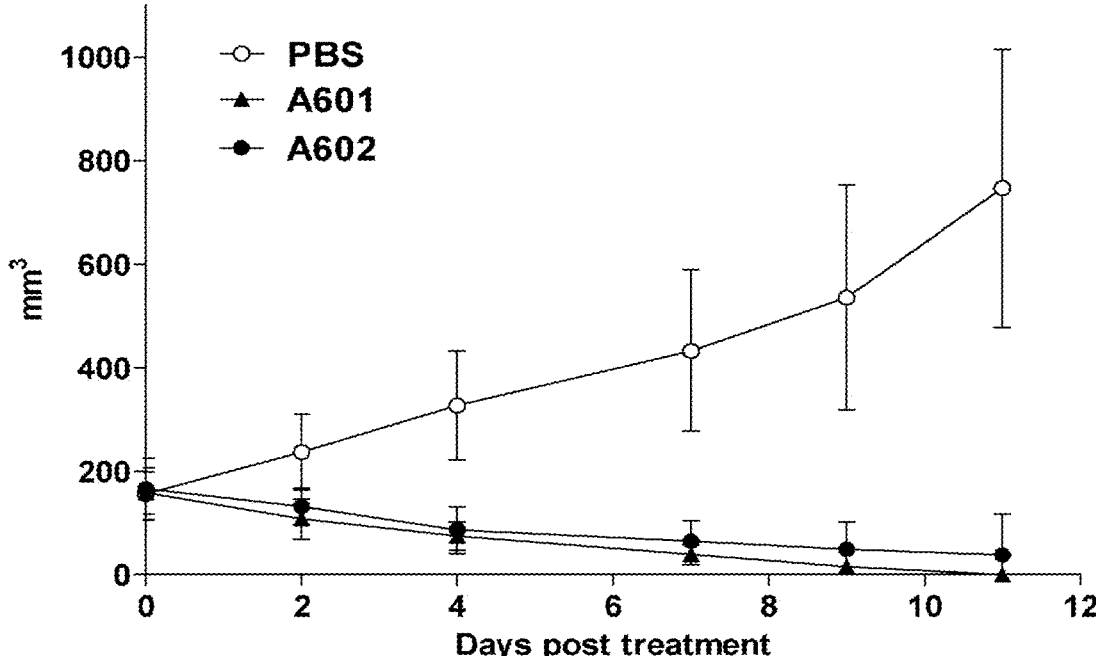
Tumor volume

[Fig. 10B]
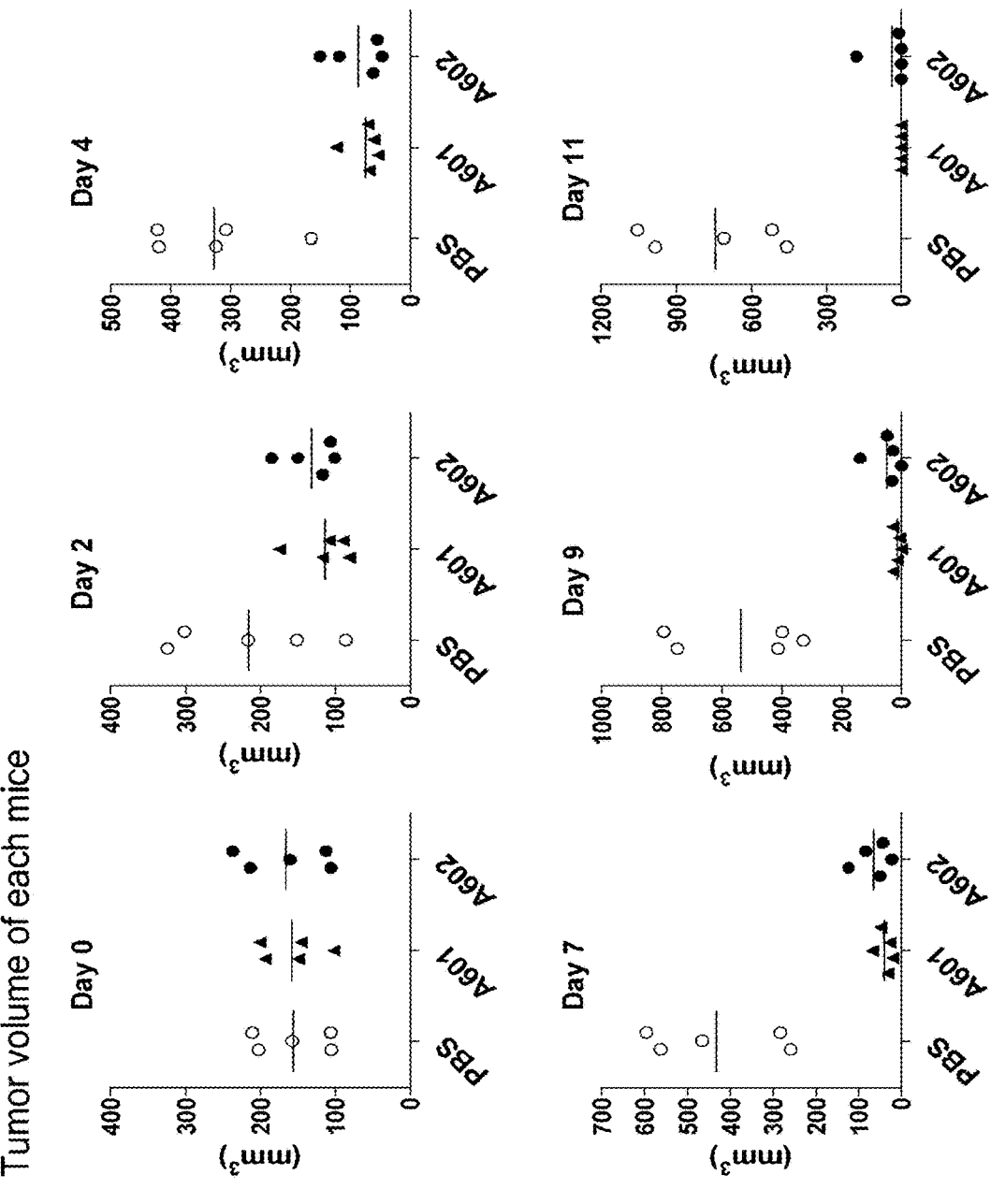
Tumor volume of each mice

[Fig. 10C]
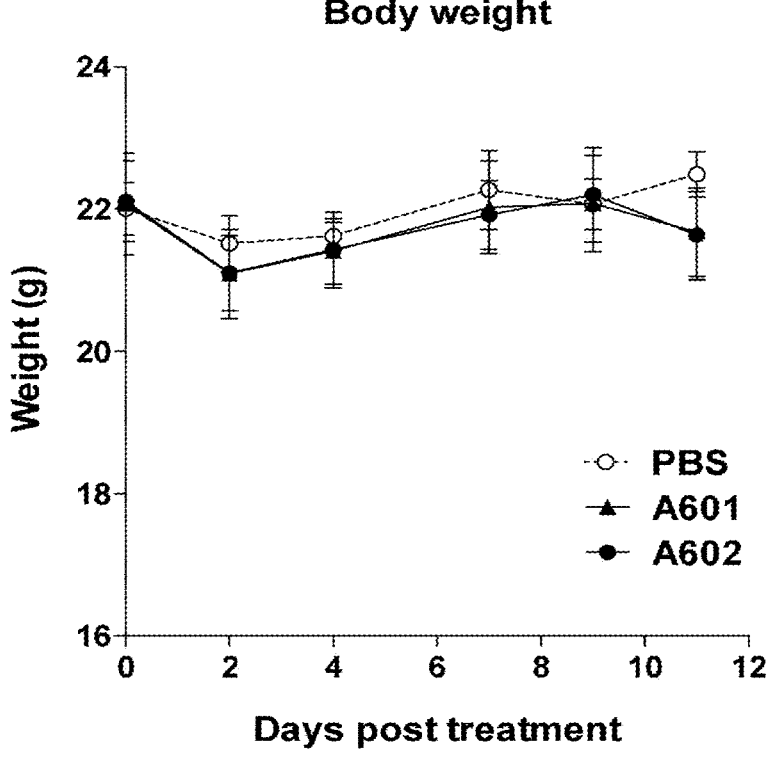

[Fig. 11A]
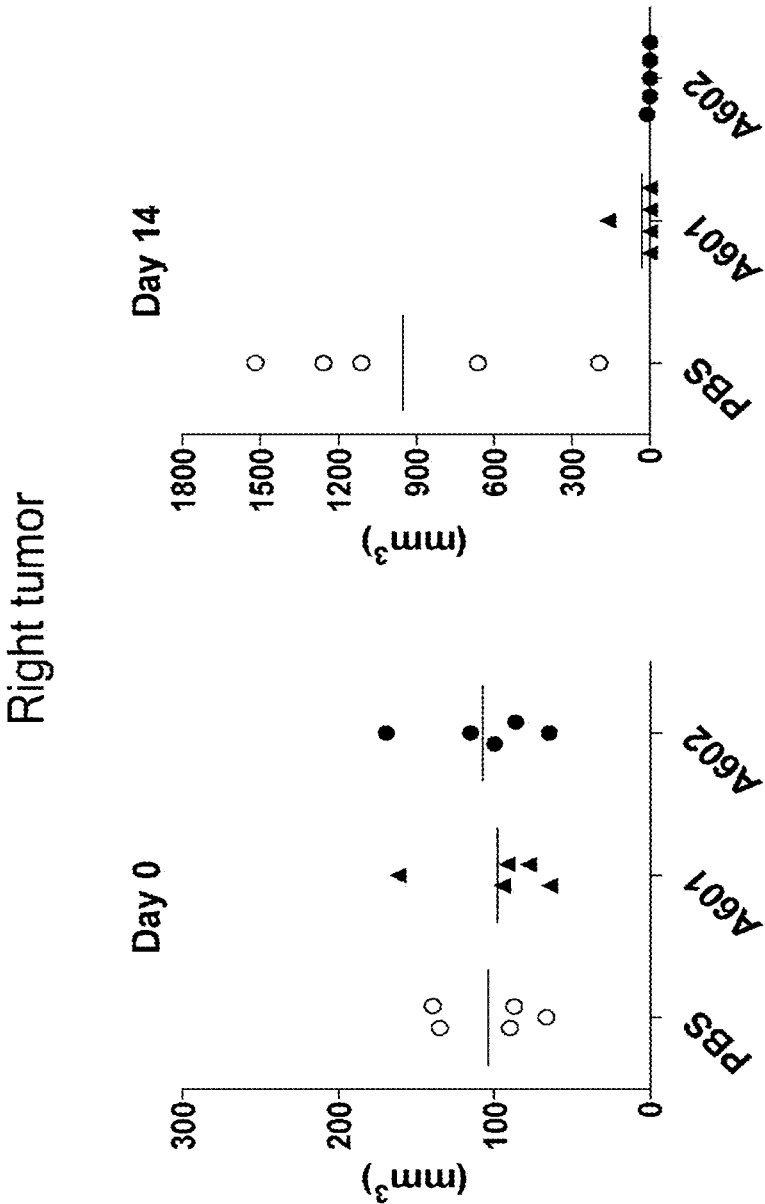

[Fig. 11B]
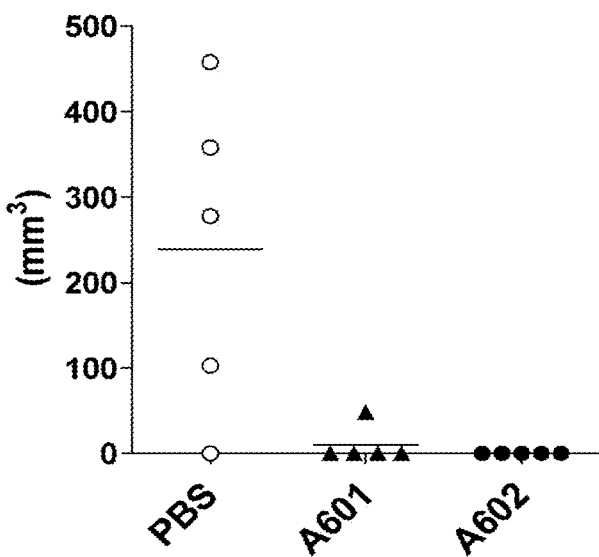
Left tumor
14 days after re-inoculation

[Fig. 12]
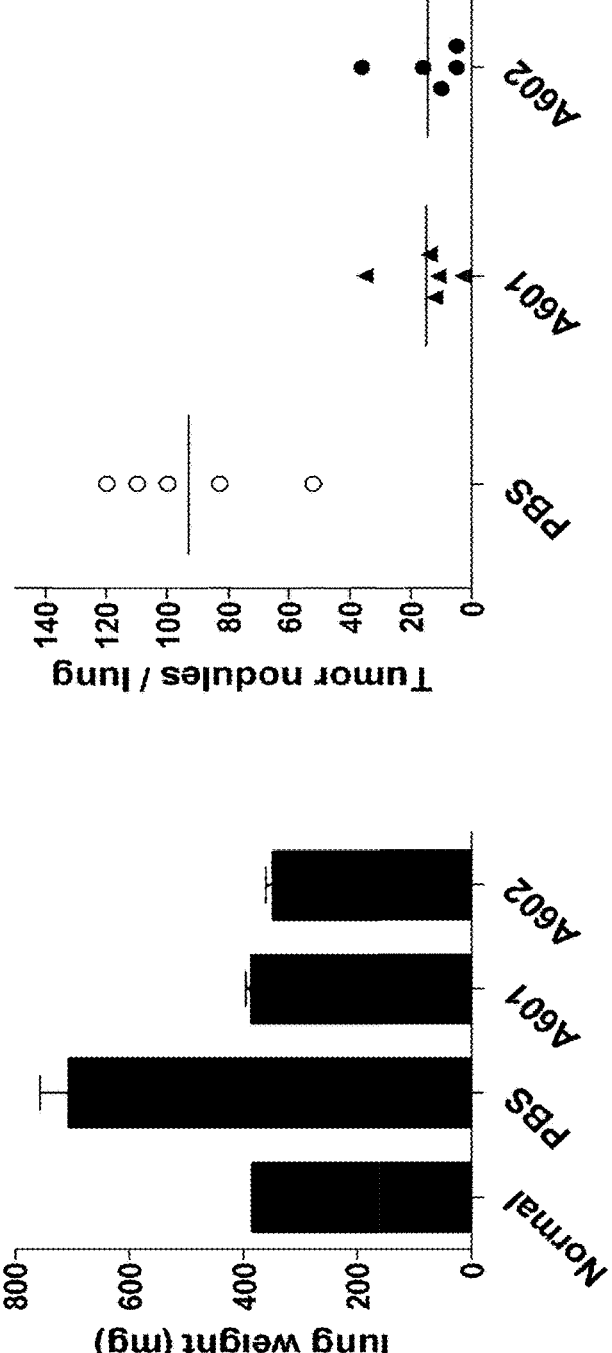
CT26 lung metastasis model
Tumor nodules / lung
Experimental Schedule
Day 0   CT26.WT  5x10⁵cells/200μl/mouse (I.V.)
Day 1   1st administration  ·PBS 50μl/S.C.
                            ·A601 40μg/50μl/S.C.
                            ·A602 40μg/50μl/S.C.
Day 5   2nd administration
Day 18  analysis
lung weight (mg)

[Fig. 13A]
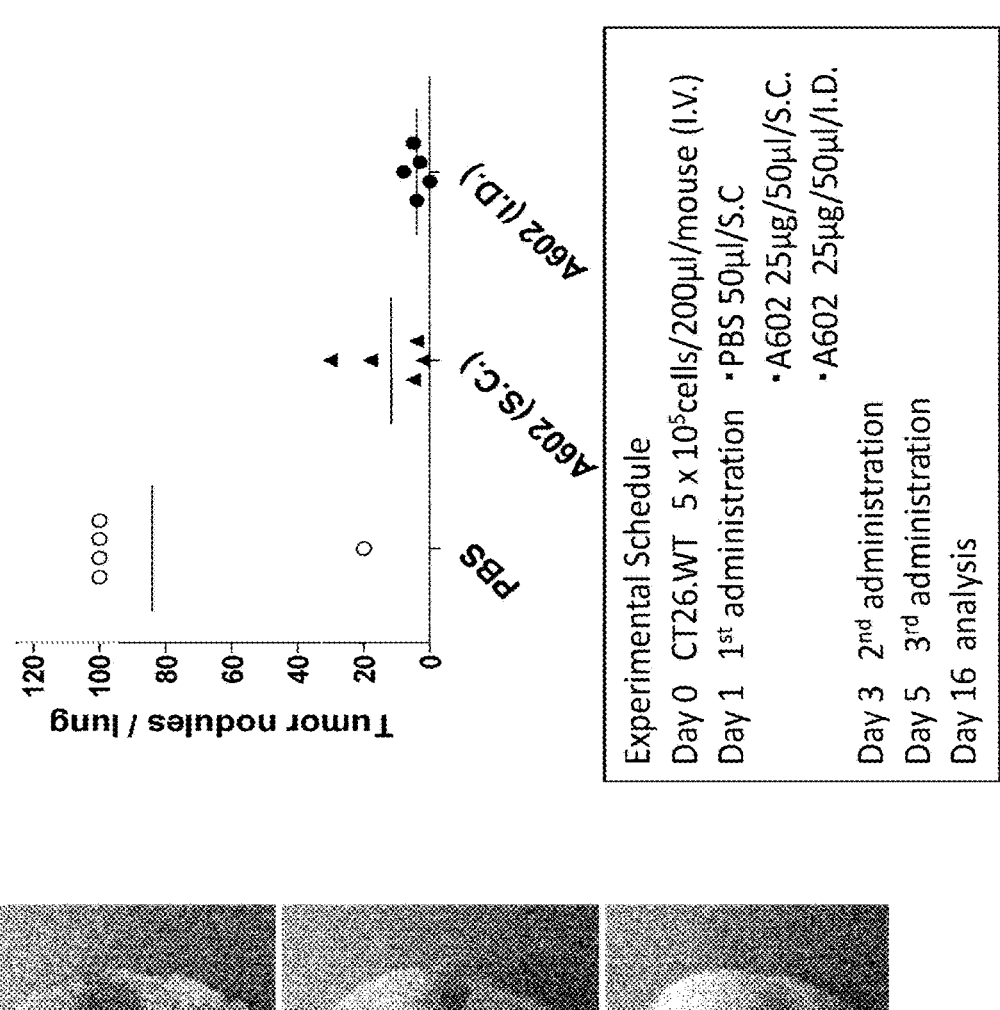
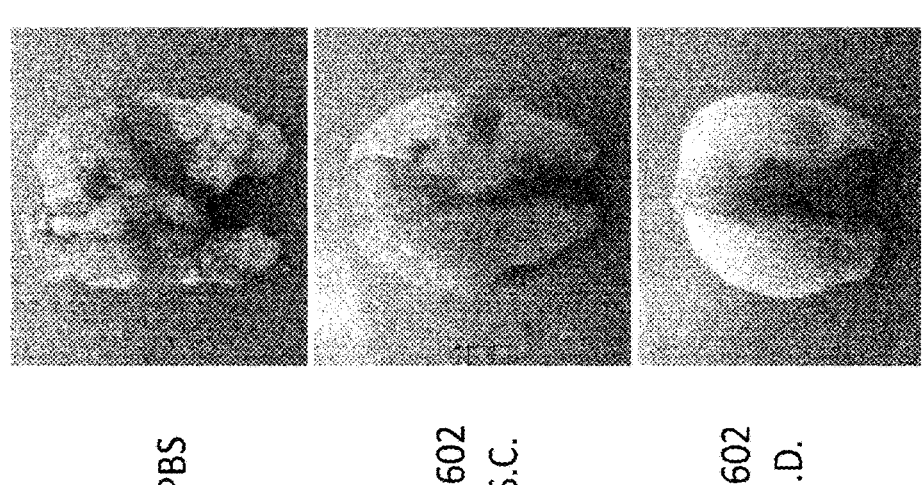

[Fig. 13B]
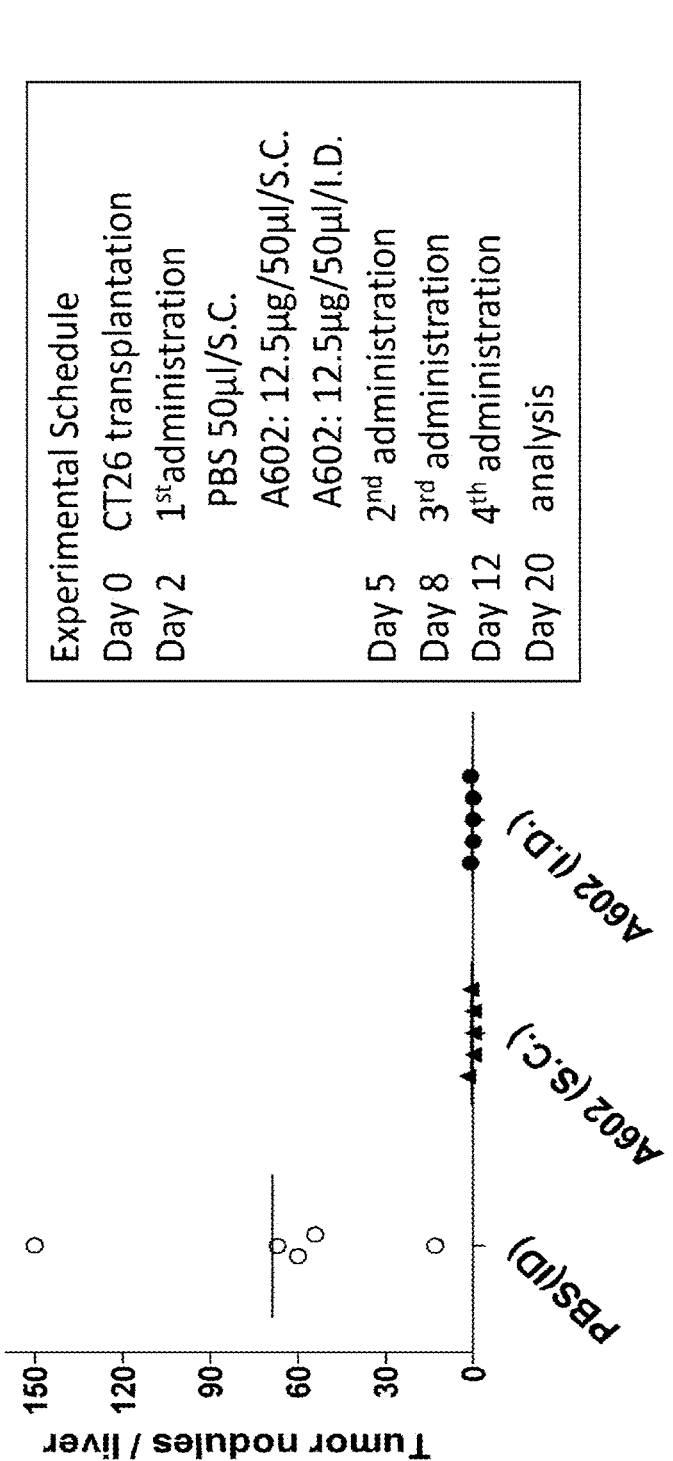
CT26 liver metastasis model

[Fig. 14A]
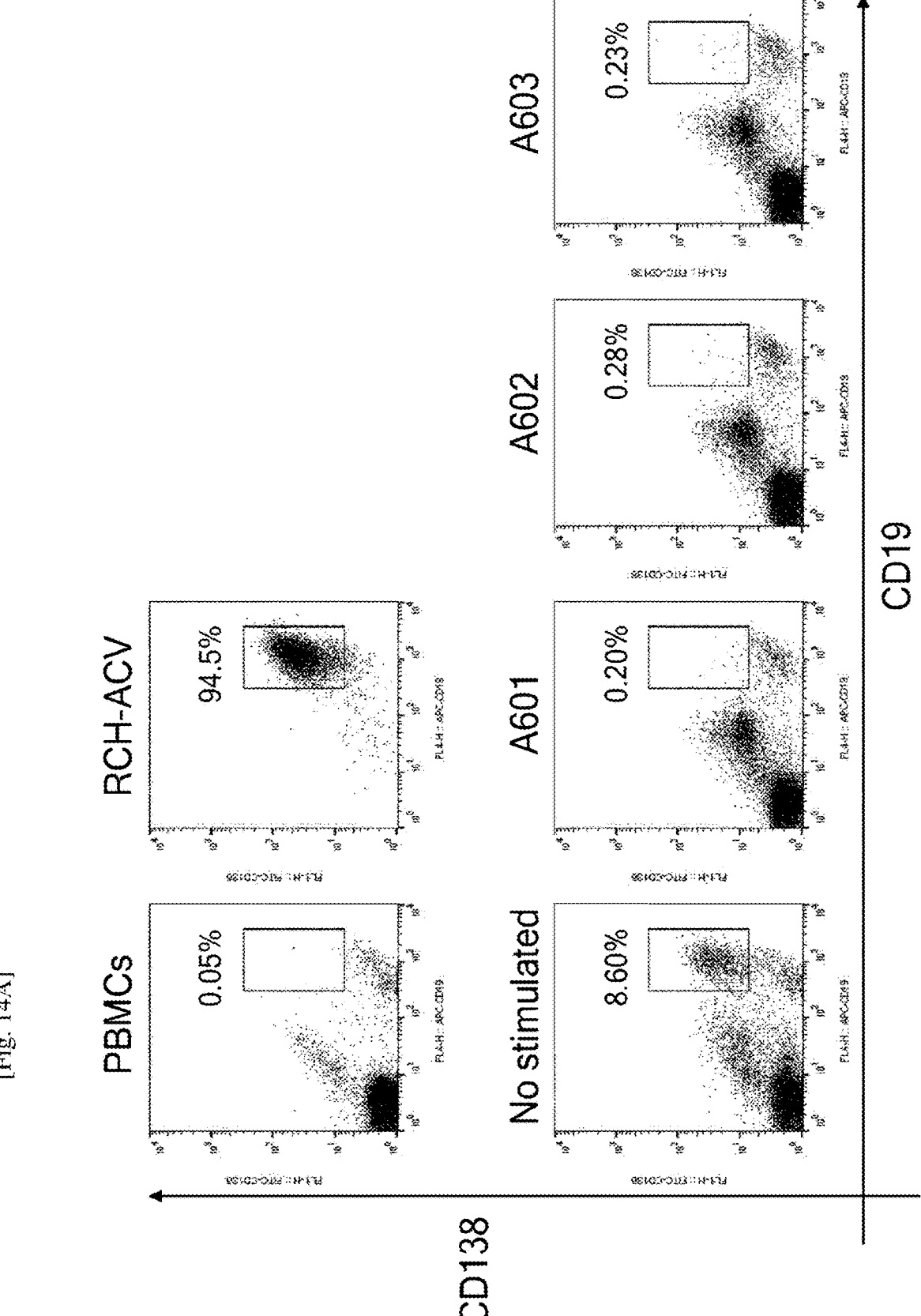

[Fig. 14B]
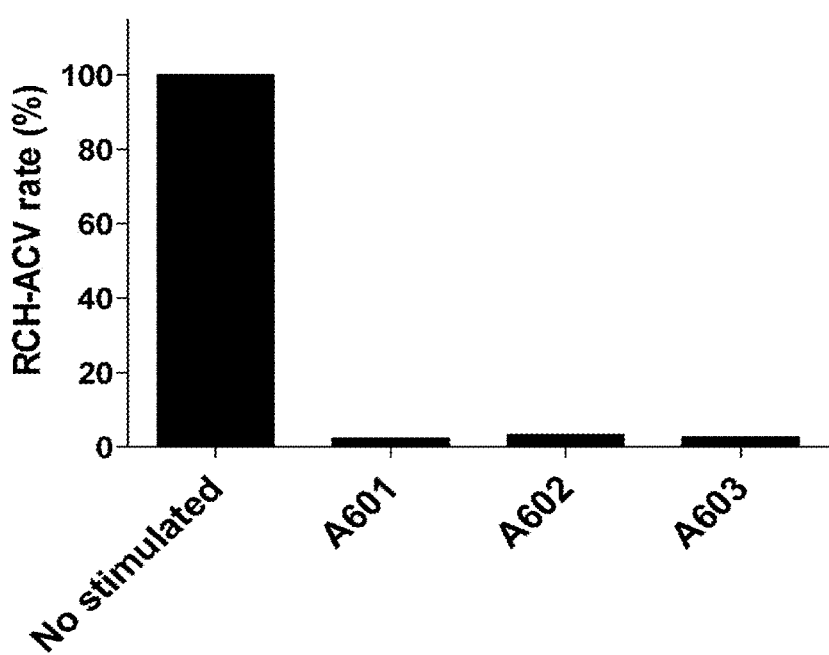

[Fig. 15A]
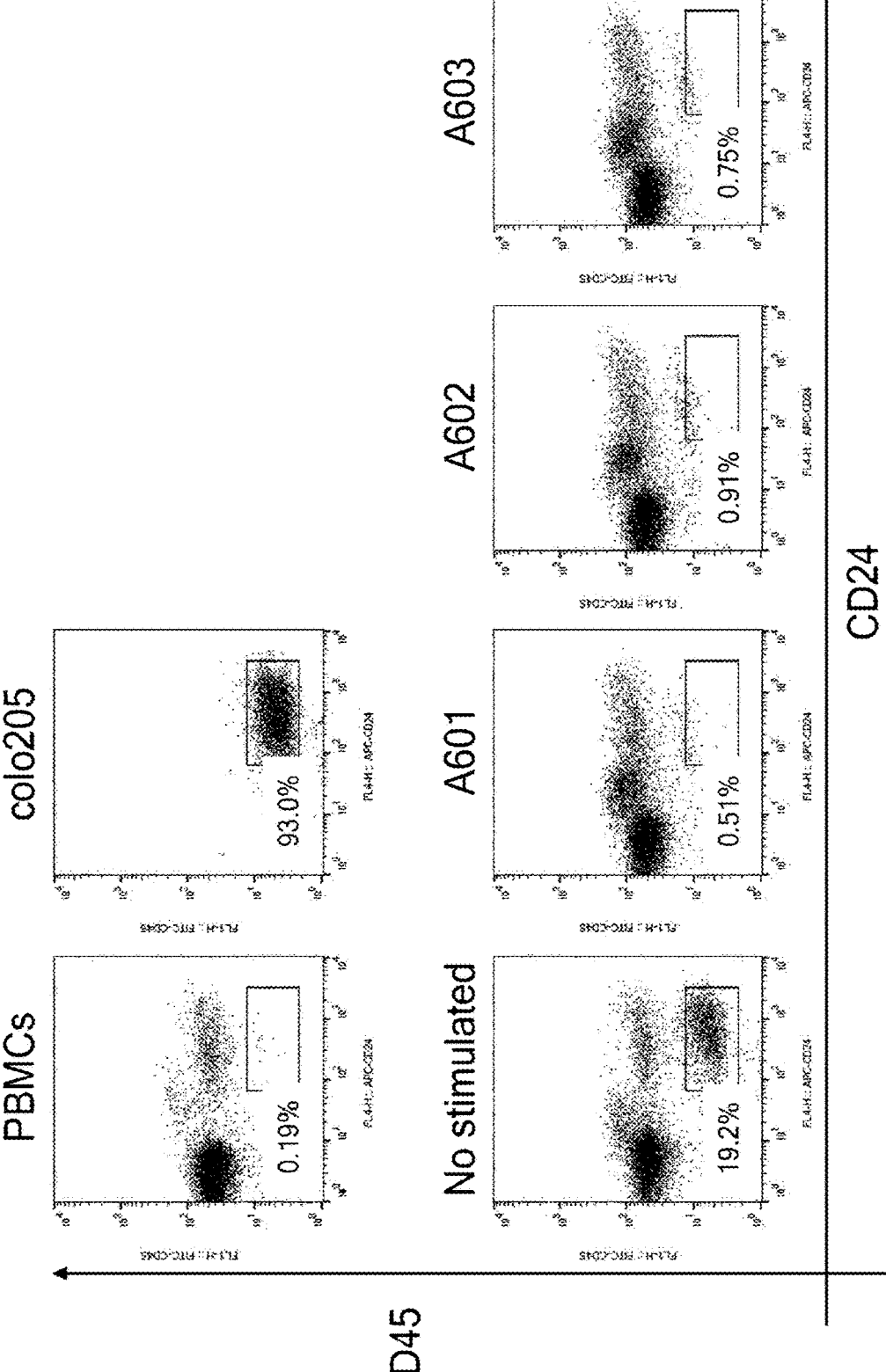

[Fig. 15B]
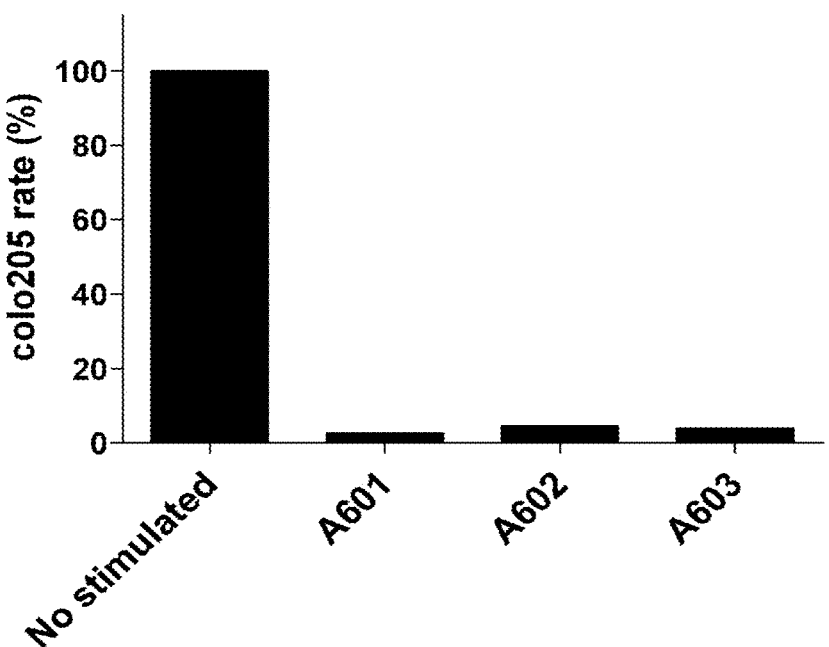

[Fig. 16A]
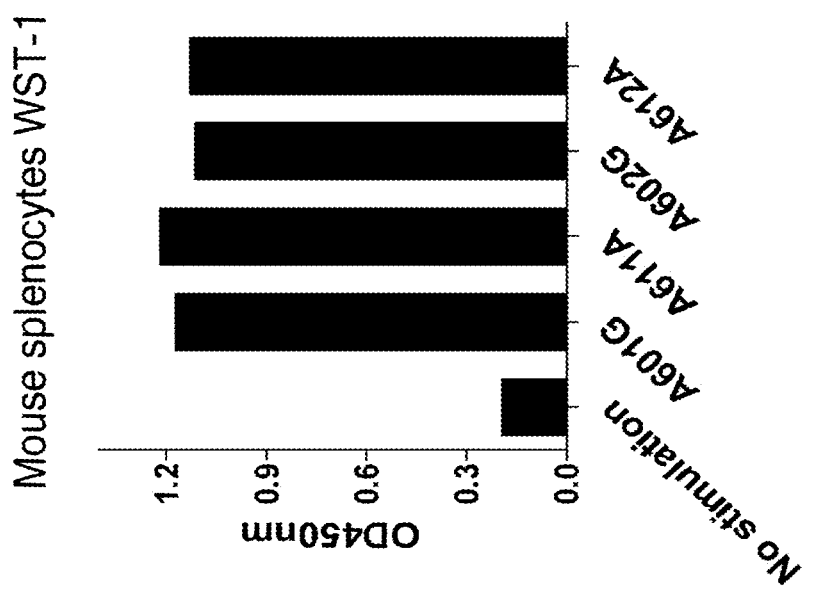
Mouse splenocytes WST-1
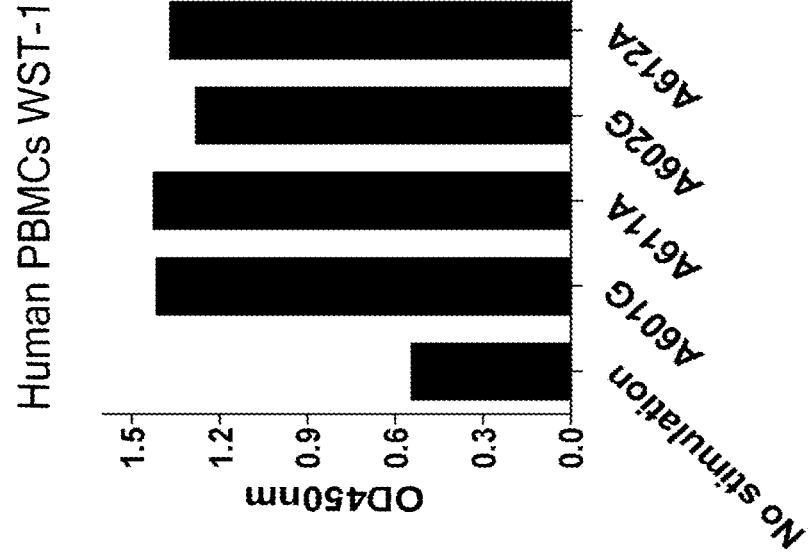
Human PBMCs WST-1

[Fig. 16B]
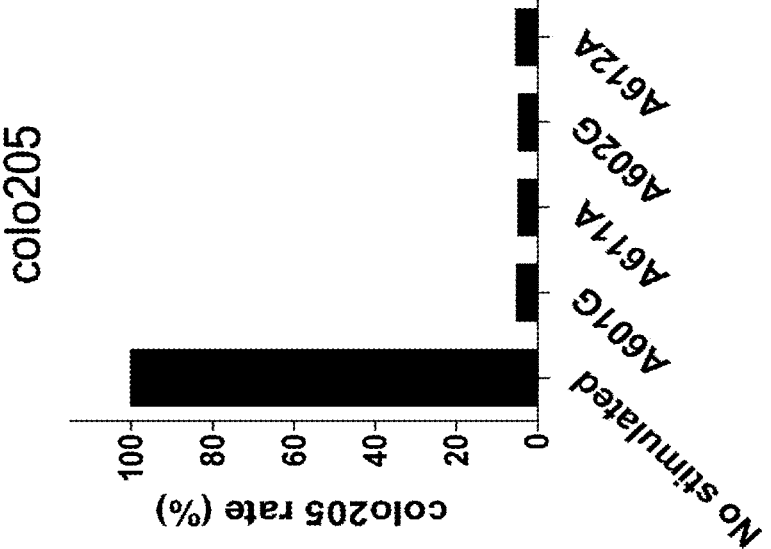
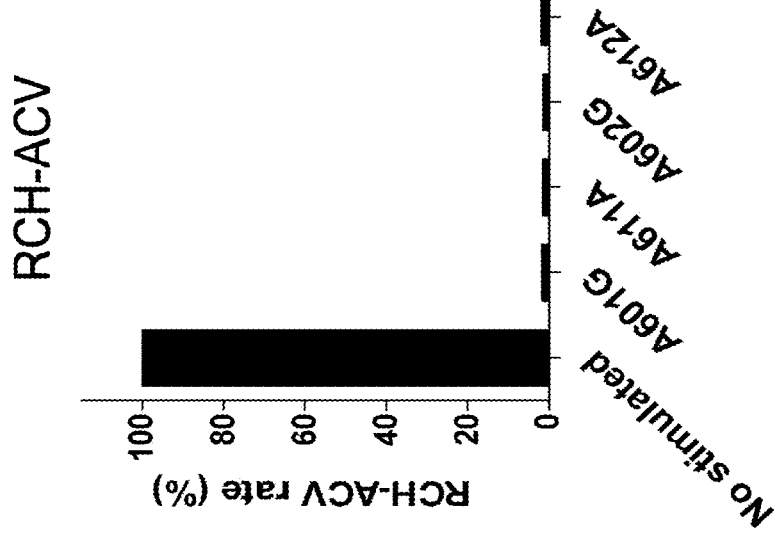

TLR9 AGONISTS

SEQUENCE LISTING

This application contains a Sequence Listing that has been submitted electronically as an ASCII text file named "53916-0002UST SL2 ST25.txt." The ASCII text file, created on Jan. 9, 2023, is 35,243 bytes in size. The material in the ASCII text file is hereby incorporated by reference in its entirety.

TECHNICAL FIELD

All publications, patents, and patent applications mentioned in this specification are herein incorporated by reference to the same extent as if each individual publication, patent, or patent application was specifically and individually indicated to be incorporated by reference.

The present invention relates to a novel oligonucleotide or the derivative oligonucleotide, which can bind to a nucleic acid receptor including TLR9. The present invention further relates to a pharmaceutical composition comprising the oligonucleotide. The present invention further relates to a method of prophylaxis or treatment of a target disease including a cancer or an infectious disease using the oligonucleotide.

BACKGROUND ART

TLR (toll-like receptor) is a family of receptors which recognize pathogen-associated molecular patterns (PAMPs) and which are located on the surface of cell membrane or endosome membrane. Activation of TLR leads to secretion of type I interferons and inflammatory cytokines. Ten kinds of TLRs, from TLR1 to TLR10, are known in human. Among them, TLR3, TLR7, TLR8 and TLR9 are endosome-resident and mainly detect nucleic acids. While TLR3 mainly recognizes double-stranded RNAs and synthetic RNAs called poly (I:C) which are similar to virus RNA. TLR7 and TLR8 mainly recognize single-stranded RNAs. On the other hand, TLR9 mainly recognizes single-stranded DNAs. In human, TLR9 is expressed in plasmacytoid dendritic cells (pDCs), B cells, eosinophils, basophils, macrophages and NK cells (Roda, J. M., et al., J Immunol, 2005. 175(3): p. 1619-27; Liu, M., et al., Nat Immunol, 2019. 20(3): p. 265-275; Hemmi, H., et al., Nature, 2000. 408 (6813): p. 740-5)

TLR9 agonists activate pDCs and B cells to promote their proliferation, productions of inflammatory cytokines and antibodies, antigen presentation, and expressions of co-stimulatory molecules and MHC molecules. Upon receipt of stimulation from TLR9 agonists, pDCs and B cells also increase expressions of chemokine receptors, resistance to apoptosis, and productions of cytokines including Th1-promoting chemokines, such as Macrophage Inflammatory Proteins 1 (MIP1) and Interferon-Inducible Protein of 10 kDa (IP10). Memory B cells especially differentiate into plasma cells, which secrete antibodies, solely depending on the activation of TLR9. An example of TLR9 agonists is CpG DNA (CpG). CpG DNA contain unmethylated cytosine and guanine, which was originally found as an important motif constituting pathogen-associated molecular patterns (PAMPs) in bacterial DNAs. (Krieg, A. M., Nat Rev Drug Discov, 2006. 5(6): p. 471-84)

The CpG-oligodeoxynucleotides (ODNs) are reported to be classified into four classes in view of structures and functions.

Class A ODN, also known as class D ODN, has a phosphorothioated backbone in several nucleotides of the 3' end and in several nucleotides of the 5' end. Class A ODN contains palindromic sequences including CpG which can form a stem-loop structure. The ends of class A ODN contain polyG sequences, which can form parallel quadruplex structures called G-tetrads (Puig M. et al., Nucleic Acids Res. 2006, 34(22): p. 6488-95). Class A ODN strongly promotes productions of interferon-alpha (IFN-α) from pDC, but activates B cells only weakly. Class B ODN, also known as class K ODN, has one and more CpG sequence(s) and has a backbone in which majority of the nucleotides are phosphorothioated. Class B ODN strongly induces proliferation of B cells, promotes secretion of IgM antibodies from B cells, and induces differentiation and maturation of pDCs. Class C ODN has a phosphorothioated backbone. Class C ODN has a palindromic sequence with CpG in the 3' end and the parindromic sequence may anneal intramolecularly to form hairpin structure. Class C ODN promotes IFN-α productions from pDCs and IL-6 productions from B cells. Thus, class C ODN bas similar functions as ones both of class A ODN and class B ODN. Class P ODN has two palindromic sequences. Class P ODN can anneal intermolecularly to form concatemers at the palindrome at the 5' end of intramolecularly to form a hairpin-structure in the GC-rich 3' end. Class PODN strongly induces productions of type I IFNs (Scheiermann, J. et al., Vaccine, 2014. 32(48): p. 6377-89).

Mechanisms that the CpG-ODNs activate cells expressing TLR9 are reported as follows. First, internalized CpG-ODNs bind to TLR9 in the endosome. Once the CpG-ODNs bind to TLR9, the adaptor protein MyD88 binding to the cytosolic side of TLR9 is activated by phosphorylation. The activated MyD88 induces transcription of cytokines including type I interferons (IFNs) through activation of transcription factors such as IRF3, 5 and 7. The activated MyD88 also conveys the signaling through nuclear factor-kappa B (NF-kB) pathway; the signal downstream of MyD88 ubiquitinates IkB (inhibitor of kB or inhibitor of kappa-beta) and induce degradation of IkB, which activates NF-kB. Upon NF-kB activation, NF-kB binds to the NF-kB promoters and activates the expression of target genes. As a result, productions of inflammatory cytokines such as Interleukin-Ibeta (IL-1β), TNF-alpha (TNF-α) and Interleukin-6 (IL-6) are induced.

Since the CpG-ODNs possess above-mentioned biological TLR9 activating activity, the administration of CpG-ODNs is suitable for treatment and/or prevention of several diseases or disorders as follows.

<Anti-Cancer (Tumor) Activity>

The CpG-ODNs can have effects on tumor microenvironment (TME) and convert cold tumor into hot tumor ("Warming "Cold" Melanoma with TLR9 Agonists", Cancer Discov, 2018. 8(6): p. 670). TME is an environment constructed by tumor cells and non-tumor cells surrounding tumors such as immune cells, fibroblasts and vascular cells. The status of a TME profoundly influences tumor progression. Cold tumor is a tumor which contains immunosuppressive cells such as tumor-associated macrophages (TAM), myeloid-derived suppressor cells (MDSC) and regulatory T cells (Tregs), which constitutes immunosuppressive TME, and only few activated tumor infiltrating lymphocytes (TIL). Cold tumor is often resistant to cancer treatments including immunotherapy. Hot tumor is a tumor which contains anti-tumor immune cells including TILs and M1 macrophages, which constitutes immunologically activated TME. Hot tumor is generally responsive to cancer treatments. For example, it is reported that intratumoral administration of CpG-ODNs leads to increase of T cells, pDC and NK cells, reduction of Tregs and suppression of MDSC (Shirota, H., et al., Vaccines (Basel), 2015. 3(2): p. 390-407). In addition, TLR9 agonists are reported to re-educate pro-tumor M2-like macrophages to induce antitumor M1-like macrophage polarization. (Mantovani, A., et al., J Exp Med, 2015. 212(4): p. 435-45) The CpG-ODNs are also reported to strengthen the antitumor activity of macrophages to engulf cancer cells which express 'don't eat me signal' such as CD47 (Liu, M., et al., Nat Immunol, 2019. 20(3): p. 265-275).

The CpG-ODNs can also suppress immunosuppressive nature of monocytic (CD11b+, Ly6G-, Ly6C$^{high}$) MDSC, such as suppressive activity of T cell function (Shirota, Y., et al., J Immunol, 2012. 188(4): p. 1592-9).

<Prophylaxis or Therapies of Th2 or Th17-Mediated Diseases>

The CpG-ODNs are suitable for effective prophylaxis or therapies of Th2 or Th17-mediated diseases. The conventional CpG ODNs have been shown for their immunomodulatory effects to modulate the balance of immune response by activating Th1 cells and Tregs and, as a result, suppress Th2 cells and Th17 cells. It is considered that induction of differentiation into Th1 cells by CpG-ODNs leads to reduction of Th2 cells because Th1 cells and Th2 cells reciprocally inhibit differentiation of each other respectively into Th2 cells or Th1 cells.

Many factors modulating the balance of Th17 cells and Tregs have recently been reported. The examples of such factors are in the downstream signals of T-cell receptors, co-stimulatory molecules, cytokines, metabolic pathways and the intestinal microbiota (Lee, G. R., Int J Mol Sci, 2018. 19(3): p. 730).

It has been reported that TLR4 agonist, LPS, induces differentiation of Th17 cells and TLR2 agonist, peptidoglycan, induces differentiation of Th17 cells and Th1 cells moderately. Meanwhile, CpG-ODNs are reported to preferentially induce differentiation of Th1 cells through IFN-α productions (Shi, G., et al., J Immunol, 2013. 191(1): p. 415-23).

The feasibilities of therapies to maintain the balance of immunity have also been shown in in-vivo setting. For example, when a CpG-ODN was administered to model mice and patients suffering from ulcerative colitis, it was observed that Th17 cell numbers, and the productions of IL-17 and IL-6 were reduced, while Treg numbers and IL-10 productions were increased, which resulted in the improvement in the symptoms (Schmitt, H et al., J Crohns Colitis, 2018, 12 (Suppl1): p. S003). It was also reported that the addition of CpG reduces EAE symptoms of the mice by complete Freund's adjuvant, revealing the effect of CpG in lowering Th17-mediated pathogenesis (Tigno-Aranjuez, J T, et al., J Immunol, 2009, 183(9): p. 5654-61).

It is also suggested that CpG-ODNs are effective for asthma and atopic diseases, which belong to Th17-mediated diseases, based on the observation that CpG ODNs induced production of indoleamine 2,3-dioxygenase (IDO) from dendritic cells, and activation and proliferation of Tregs (Kline, J. N., et al., Drug News Perspect, 2008. 21(8): p. 434-9).

<Combination Therapy>

Further, the CpG-ODNs are also reported to be suitable for combination therapy because the CpG-ODNs exhibit a modulation activity of immune activity as stated above. Previous reports reported combination with the therapies including (i) vaccines; (ii) antibody drugs; (iii) conventional chemotherapy; (iv) molecular targeting drugs; (v) surgical treatment; (vi) cytokines; (vii) adoptive immune cell therapies (also known as adoptive cell transfer (ACT)); and (viii) agonists to the receptors of nucleic acids.

Combination with '(i) Vaccines'

The CpG-ODNs can improve the immunogenicity of vaccines. For example, CpG-ODNs can be administered together with the anti-cancer vaccine, such as melanoma-antigen vaccine (Scheiermann, J. et al., D. M., Vaccine, 2014. 32(48): p. 6377-89; Shirota, H., et al., Vaccines (Basel), 2015. 3(2): p. 390-407) as well as with vaccines against virus such like cytomegalovirus, malaria, anthrax and influenza virus (Scheiermann, J. et al., D. M., Vaccine, 2014. 32(48): p. 6377-89). The hepatitis B vaccine Heplisav-B® comprising a CpG-ODN and hepatitis B antigens was approved by FDA.

Combination with '(ii) Antibody Drugs' (Such as Immune Checkpoint Inhibitors (CPIs) and Cytotoxic Antibodies)

CPIs are the drugs to convert immunosuppressive status of tumor microenvironment or the environment surrounding infected cells by binding to checkpoint molecules or their ligands. For example, combination of a CpG-ODN with Keytruda (pembrolizumab) has been examined in the clinical trial of progressive melanoma (Ribas, A., et al., Cancer Discov, 2018. 8(10): p. 1250-1257). The clinical trial of combinatorial use with Yervoy (ipilimumab) has also been conducted in the aim of treatment of progressive solid tumor (Reilley, M., et al., Journal of Clinical Oncology, 2019. 37(15_suppl): p.TPS2669-TPS2669). Interestingly, it is suggested that combination of CpG-ODNs and CPI is effective for patients who are resistant to standard treatment. For instance, it is reported that combination with a CpG-ODN and CPI shows anti-tumor activity even though patients are resistant to CPI such as PD-1 antibodies (Wang, S., et al., Proc Natl Acad Sci USA, 2016. 113(46): p. E7240-E7249).

Cytotoxic antibodies are the drugs that induce antibody-dependent cellular cytotoxicity (ADCC), complement-dependent cellular cytotoxicity (CDC) and antibody-dependent cellular phagocytosis (ADCP). Synergistic effects by combinatorial use of CpG-ODNs and cytotoxic antibodies have been reported (Hiramatsu, K., et al., Cancer Sci, 2015. 106(10): p. 1474-8). For example, combination of a CpG-ODN with Rituxan (rituximab) has been examined in the clinical trial of non-Hodgkin's lymphoma (Friedberg. J. W., et al., Blood, 2005. 105(2): p. 489-95). It has also been shown that combination of CpO oligonucleotide, poly (I:C) and a cytotoxic antibody had anti-tumor activity even when patients were resistant to the cytotoxic antibody such as Herceptin (trastuzumab) (Charlebois, R., et al., Cancer Res, 2017. 77(2): p. 312-319).

Combination with '(iii) Conventional Chemotherapies'

Conventional chemotherapeutic drugs are made from chemical substances which inhibit proliferation of fast-growing tumor cells and kill such cells. For example, combination of a platinum-based drug, a taxane-based drug, and a CpG-ODN was examined in a clinical study (Krieg, A. M., J Clin Invest, 2007. 117(5): p. 1184-94).

Combination with '(iv) Molecular Targeting Drugs'

The conventional molecular targeting drugs are generally made of small molecules binding to specific target molecules and regulate their functions. The examples of the targeted molecules are such those causing carcinogenesis, related to driver mutations or being involved in homeostasis of the tumor cells. For instance, the synergy between CpG and bortezomib in multiple myeloma was reported in pre-clinical setting and it was concluded to constitute the basis of feasibility to be tested at the clinical stage (Ray. A., et al., Leukemia, 2014. 28(8): p. 1716-24).

5

Combination with (v) Surgical Treatments (Including Radiation Therapy Cryoablation and Radiofrequency Ablation)

It was reported that administration of a CpG-ODN after surgical resection improved survival rate (Weigel, B. J., et al., Clin Cancer Res, 2003. 9(8): p. 3105-14). Radiation therapy is a treatment which damages DNA of proliferating tumor cells and kills such cells with radiation. Cryoablation is a treatment which freezes and kills tumor cells. Radiofrequency ablation is a treatment which coagulates the tumor cells with heat generated from radiofrequency and kills those cells. CpG-ODNs are considered to be effective to evoke immunity against the tumor antigens released from the dead cell killed by these treatments (Jahrsdörfer, B. et al., G. J., Update Cancer Ther, 2008. 3(1): p. 27-32).

Combination with '(vi) Cytokines'

The examples of the cytokines are IFN-α and IL-18, which activate NK cells or dendritic cells. It is reported that the combination of IL-18 and a CpG-ODN induced apoptosis of malignant B cells and these B cells secreted granzyme, which further killed the neighbor malignant B cells (Jahrsdörfer, B. et al., Update Cancer Ther, 2008. 3(1): p. 27-32).

Combination with '(vii) Adoptive Immune Cell Therapies'

Adoptive immune cell therapy is a type of therapy that administers immune cells modified ex vivo; the examples of such therapy are as following: CAR-T therapy, utilizing the genetically modified T cells transduced with TCR against specific cancer antigens, and immune cells, such as TILs or dendritic cells either from the patients or donors, stimulated ex vivo to have anti-tumor effects (Xu, L., et al., Clin Dev Immunol, 2010. 2010: p. 410893).

Combination with '(viii) Agonists to Receptors of Nucleic Acids'

Combination with a TLR7/8 agonist was reported to show synergistic effects in a clinical trial (Shirota, H., et al., Vaccines (Basel), 2015. 3(2): p. 390-407). Synergistic effect between TLR9 agonist, such as CpG and Stimulator of interferon genes (STING) agonist is also reported to enhance Th1-biased immune responses, such as antigen-specific IgG and IFN-γ production in PBMC, as well as cytotoxic CD8(+) T-cell responses (Temizoz B., et al, Eur J Immunol, 2015, 45(4): p. 1159-69)

<Mechanisms Supporting Combination Therapies Including Administration of CpG>

Some of the treatments or drugs described above have been shown to induce immunogenic cell death (ICD) and examined for the combination with CpG-ODNs. ICD is a type of cell death where the cell carcasses or dying cells killed by ICD induce strong immune response by secretion of DAMPs; the molecules constituting DAMPs were reported to be, for example, calreticulin, high-mobility group box (HMGB), heatshock protein or ATP. Presentation of increased amount of such DAMPs has been observed comparing to the usual cell death. (Bedognetti, D., et al., J Immunother Cancer, 2019. 7(1): p. 131) Some chemotherapeutic drugs and some molecular targeting drugs are known as inducers of ICD; such ICD inducers include doxorubicin, mitoxantrone, oxaliplatin and bortezomib. Radiation and photodynamic therapy (PDT) are also known as inducers of ICD. (Galluzzi, L., et al., Nat Rev Immunol, 2017. 17(2): p. 97-111)

Some of the treatments or drugs which suppress or kill Tregs are examined for combination with CpG-ODNs described above. For example, CpG-ODNs synergistically enhance the immune response after depletion of Treg with the anti-CD25 antibody (Jarry, U., et al., J Neuroimmunol, 2014. 267(1-2): p. 35-42).

Consequently, the CpG-ODNs can be administered solo or in combination with at least one active ingredient for the following pharmaceutical purposes: (i) immunostimulatory effects to prevent and treat neoplasms including cancers (for example, metastatic solid cancer, melanoma, cutaneous T-cell lymphoma, chronic lymphocytic leukemia and the like) and infectious diseases, (ii) immunomodulatory effects to prevent or treat immune-mediated diseases such as Th2 or Th17-related diseases including some types of autoimmune diseases and allergic diseases and (iii) modulation of responsiveness of tumor cells expressing TLR7/9 to anti-cancer drugs and immune cells.

CITATION LIST

Patent Literature

WO2014082254A
JP5011520B
WO2004016805A

Non-Patent Literature (No authors listed), Warming "Cold" Melanoma with TLR9 Agonists. Cancer Discov, 2018. 8(6): p. 670.

Aarts, B. M., et al., Cryoablation and immunotherapy: an overview of evidence on its synergy. Insights Imaging, 2019. 10(1): p. 53.

Bauer, S., et al., Human TLR9 confers responsiveness to bacterial DNA via species-specific CpG motif recognition. Proc Natl Acad Sci USA, 2001. 98(16): p. 9237-42.

Bedognetti, D., et al., Toward a comprehensive view of cancer immune responsiveness: a synopsis from the SITC workshop. J Immunother Cancer, 2019. 7(1): p. 131.

Bhan, U., et al., TLR9 is required for protective innate immunity in Gram-negative bacterial pneumonia: role of dendritic cells. J Immunol, 2007. 179(6): p. 3937-46.

Bode, C., et al., Human plasmacytoid dentritic cells elicit a Type I Interferon response by sensing DNA via the cGAS-STING signaling pathway. Eur J Immunol, 2016. 46(7): p. 1615-21.

Chang, C. L., et al., Immune mechanism of the antitumor effects generated by bortezomib. J Immunol, 2012. 189(6): p. 3209-20.

Charlebois, R., et al., PolyI: C and CpG Synergize with Anti-ErbB2 mAb for Treatment of Breast Tumors Resistant to Immune Checkpoint Inhibitors. Cancer Res, 2017. 77(2): p. 312-319.

Davola, M. E., et al., Oncolytic viruses: how "lytic" must they be for therapeutic efficacy? Oncoimmunology, 2019. 8(6): p. e1581528.

Di Domizio, J., et al., TLR7 stimulation in human plasmacytoid dendritic cells leads to the induction of early IFN-inducible genes in the absence of type I IFN. Blood, 2009. 114(9): p. 1794-802.

Ding A. S. et al., Targeting Myeloid Cells in Combination Treatments for Glioma and Other Tumors, Front Immunol, 2019, 10: p. 1715

Friedberg, J. W., et al., Combination immunotherapy with a CpG oligonucleotide (1018 ISS) and rituximab in patients with non-Hodgkin lymphoma: increased interferon-alpha/beta-inducible gene expression, without significant toxicity. Blood, 2005. 105(2): p. 489-95.

Gabrilovich, D. I., Myeloid-Derived Suppressor Cells. Cancer Immunol Res, 2017, 5(1): p. 3-8

Galluzzi, L., et al., Immunogenic cell death in cancer and infectious disease. Nat Rev Immunol, 2017. 17(2): p. 97-111.

Harrington, K., et al., Optimizing oncolytic virotherapy in cancer treatment. Nat Rev Drug Discov, 2019. 18(9): p. 689-706.

Hartmann, G. et al., Mechanism and function of a newly identified CpG DNA motif in human primary B cells. J Immunol, 2000. 164(2): p. 944-53.

Hato, S. V., et al., Molecular pathways: the immunogenic effects of platinum-based chemotherapeutics. Clin Cancer Res, 2014. 20(11): p. 2831-7.

Hemmi. H., et al., A Toll-like receptor recognizes bacterial DNA. Nature, 2000. 408(6813): p. 740-5.

Hiramatsu, K., et al., CpG oligodeoxynucleotides potentiate the antitumor activity of anti-BST2 antibody. Cancer Sci, 2015. 106(10): p. 1474-8.

Hollingsworth, R. E., et al., Turning the corner on therapeutic cancer vaccines. NPJ Vaccines, 2019. 4: p. 7.

Iurescia, S., et al., Targeting Cytosolic Nucleic Acid-Sensing Pathways for Cancer Immunotherapies. Front Immunol, 2018. 9: p. 711.

Jahrsdörfer. B. et al., CpG oligodeoxynucleotides as immunotherapy in cancer. Update Cancer Ther, 2008. 3(1): p. 27-32.

Jarry, U., et al., Treg depletion followed by intracerebral CpG-ODN injection induce brain tumor rejection. J Neuroimmunol, 2014. 267(1-2): p. 35-42.

Kasperkovitz, P. V., et al., Toll-like receptor 9 modulates macrophage antifungal effector function during innate recognition of Candida albicans and Saccharomyces cerevisiae. Infect Immun, 2011. 79(12): p. 4858-67.

Kleinovink, J. W., et al., Photodynamic-Immune Checkpoint Therapy Eradicates Local and Distant Tumors by CD8. Cancer Immunol Res. 2017. 5(10): p. 832-838.

Kline, J. N., et al., Toll-like receptor 9 activation with CpG oligodeoxynucleotides for asthma therapy. Drug News Perspect, 2008. 21(8): p. 434-9.

Krieg, A. M., Therapeutic potential of Toll-like receptor 9 activation. Nat Rev Drug Discov, 2006. 5(6): p. 471-84.

Krieg, A. M., Development of TLR9 agonists for cancer therapy. J Clin Invest, 2007. 117(5): p. 1184-94.

Lee, G. R., The Balance of Th17 versus Treg Cells in Autoimmunity. Int J Mol Sci, 2018. 19(3): p. 730.

Liu, M., et al., Metabolic rewiring of macrophages by CpG potentiates clearance of cancer cells and overcomes tumor-expressed CD47-mediated 'don't-eat-me' signal. Nat Immunol, 2019. 20(3): p. 265-275.

Maeda, T., et al., A novel plasmacytoid dendritic cell line, CAL~1, established from a patient with blastic natural killer cell lymphoma. Int J Hematol, 2005. 81(2): p. 148-54.

Mantovani, A., et al., The interaction of anticancer therapies with tumor-associated macrophages. J Exp Med, 2015. 212(4): p. 435-45.

Martinez-Quintanilla, J., et al., Oncolytic viruses: overcoming translational challenges. J Clin Invest, 2019. 130: p. 1407-1418, Narita, M., et al., Plasmacytoid dendritic cell leukemia with potent antigen-presenting ability. Acta Haematol. 2008. 120(2): p. 91-9.

O'Donnell, J. S., et al., The Promise of Neoadjuvant Immunotherapy and Surgery for Cancer Treatment. Clin Cancer Res, 2019, 25(19): p. 5743-5751.

Ohto, U., et al., Toll-like Receptor 9 Contains Two DNA Binding Sites that Function Cooperatively to Promote Receptor Dimerization and activation. Immunity, 2018. 48(4): p. 649-658.

Ohue, Y., et al., Regulatory T (Treg) cells in cancer: Can Treg cells be a new therapeutic target? Cancer Sci, 2019. 110(7): p. 2080-2089.

Pardoll, D. M., The blockade of immune checkpoints in cancer immunotherapy. Nat Rev Cancer, 2012. 12(4): p. 252-64.

Passardi, A., et al., Immune Checkpoints as a Target for Colorectal Cancer Treatment. Int J Mol Sci. 2017. 18(6): E1324

Patin, E. C., et al., Pattern recognition receptors in fungal immunity. Semin Cell Dev Biol, 2019. 89: p. 24-33.

Pohar, J., et al., Phosphodiester backbone of the CpG motif within immunostimulatory oligodeoxynucleotides augments activation of Toll-like receptor 9. Sci Rep, 2017. 7(1): p. 14598.

Pohar, J., et al., Selectivity of Human TLR9 for Double CpG Motifs and Implications for the Recognition of Genomic DNA. J Immunol, 2017. 198(5): p. 2093-2104.

Puig M. et al., Use of thermolytic protective groups to prevent G-tetrad formation in CpG ODN type D: structural studies and immunomodulatory activity in primates, Nucleic Acids Res. 2006, 34(22): p. 6488-95

Raja. J., et al., Oncolytic virus immunotherapy: future prospects for oncology, J Immunother Cancer, 2018. 6(1): p. 140.

Ray, A., et al., A novel TLR-9 agonist C792 inhibits plasmacytoid dendritic cell-induced myeloma cell growth and enhance cytotoxicity of bortezomib. Leukemia. 2014. 28(8): p. 1716-24.

Reilley, M., et al., Phase I trial of TLR9 agonist lefitolimod in combination with CTLA-4 checkpoint inhibitor ipilimumab in advanced tumors. Journal of Clinical Oncology, 2019. 37(15_suppl): p.TPS2669-TPS2669.

Ribas, A., et al., SD-101 in Combination with Pembrolizumab in Advanced Melanoma: Results of a Phase Ib, Multicenter Study. Cancer Discov. 2018. 8(10): p. 1250-1257.

Roda, J. M., et al., CpG-containing oligodeoxynucleotides act through TLR9 to enhance the NK cell cytokine response to antibody-coated tumor cells. J Immunol, 2005. 175(3): p. 1619-27.

Sargent, D. J., et al., Defective mismatch repair as a predictive marker for lack of efficacy of fluorouracil-based adjuvant therapy in colon cancer. J Clin Oncol, 2010. 28(20): p. 3219-26.

Scheiermann, J, and Klinman, D. M., Clinical evaluation of CpO oligonucleotides as adjuvants for vaccines targeting infectious diseases and cancer. Vaccine, 2014. 32(48): p. 6377-89.

Shi, G., et al., Differential involvement of Th1 and Th17 in pathogenic autoimmune processes triggered by different TLR ligands. J Immunol, 2013. 191(1): p. 415-23.

Shirota, H., et al., CpG Oligonucleotides as Cancer Vaccine Adjuvants. Vaccines (Basel), 2015. 3(2): p. 390-407.

Shirota, Y., et al., Intratumoral injection of CpG oligonucleotides induces the differentiation and reduces the immunosuppressive activity of myeloid-derived suppressor cells. J Immunol, 2012. 188(4): p. 1592-9.

Schmitt, H et al., OP004 The TLR9 agonist cobitolimod induces anti-inflammatory effects and balances the Th17/T-reg cell response in ulcerative colitis. J Crohns Colitis, 2018, 12 (Suppl1): p. S003

Sivanandam, V., et al., Oncolytic Viruses and Immune Checkpoint Inhibition: The Best of Both Worlds. Mol Ther Oncolytics, 2019. 13: p. 93-106.

Spaner, D. E., et al., Toll-like receptor agonists in the treatment of chronic lymphocytic leukemia. Leukemia, 2007. 21(1): p. 53-60.

Spisek, R., et al., Bortezomib enhances dendritic cell (DC)-mediated induction of immunity to human myeloma via exposure of cell surface heat shock protein 90 on dying tumor cells: therapeutic implications. Blood, 2007. 109(11): p. 4839-45.

Swiecki, M., et al., Unraveling the functions of plasmacytoid dendritic cells during viral infections, autoimmunity, and tolerance. Immunol Rev, 2010. 234(1): p. 142-62.

Temizoz B., et al. TLR9 and STING agonists synergistically induce innate and adaptive type-II IFN. Eur J Immunol, 2015, 45(4): p. 1159-69

Tigno-Aranjuez, J T, et al., Encephalitogenicity of complete Freund's adjuvant relative to CpG is linked to induction of Th17 cells. J Immunol, 2009, 183(9): p. 5654-61

Wang, S., et al., Intratumoral injection of a CpG oligonucleotide reverts resistance to PD-1 blockade by expanding multifunctional CD8+ T cells. Proc Natl Acad Sci USA, 2016. 113(46): p. E7240-E7249.

Wang, X., et al., A CpG oligodeoxynucleotide acts as a potent adjuvant for inactivated rabies virus vaccine. Vaccine, 2008. 26(15): p. 1893-901.

Weigel, B. J., et al., CpG oligodeoxynucleotides potentiate the antitumor effects of chemotherapy or tumor resection in an orthotopic murine model of rhabdomyosarcoma. Clin Cancer Res. 2003. 9(8): p. 3105-14.

Winkler, J., Oligonucleotide conjugates for therapeutic applications. Ther Deliv, 2013. 4(7): p. 791-809.

Xu. L., et al., CpG oligodeoxynucleotides enhance the efficacy of adoptive cell transfer using tumor infiltrating lymphocytes by modifying the Th1 polarization and local infiltration of Th17 cells. Clin Dev Immunol, 2010: p. 410893.

Yang, L. et al., Tumor-associated macrophages: from basic research to clinical application. J Hematol Oncol, 2017. 10(1): p. 58.

Zimmerman, G., et al., Post-traumatic anxiety associates with failure of the innate immune receptor TLR9 to evade the pro-inflammatory NFκB pathway. Transl Psychiatry, 2012. 2: p. e78.

SUMMARY OF INVENTION

Technical Problems

The present invention provides novel TLR agonists and therapeutic uses thereof.

Solution to Problem

The inventors newly found that
(1) the oligonucleotides of the present invention can be used for the activation or modulation of immunity in the subject; and
(2) the oligonucleotides of the present invention are especially useful for the treatment of a subject suffering from diseases including tumor, infection of a microorganism, a primary immunodeficiency disease and a Th2/Th17-related disease or for the prophylaxis of such diseases.

The present invention includes the following embodiments:
(1) A single strand oligonucleotide comprising sequence motifs 5'-tegcaacgttt-3' (SEQ ID NO: 1) and 5'-cgaeg-3'.
(2) The oligonucleotide according to (1), wherein the oligonucleotide comprises a nucleotide sequence motif 5-togcaacgttt-n-cgacg-n-cg-nn-cg-3' (SEQ ID NO:2), wherein n denotes any base.
(3) The oligonucleotide according to (1) or (2), wherein the total nucleotide number is from 20 to 25, preferably from 21 to 24, more preferably from 22 to 23.
(4) The oligonucleotide according to any one of (1)-(3), wherein the oligonucleotide comprises a sequence motif selected from the group consisting of the followings:

```
                                    (SEQ ID NO: 54)
    5'-tcgcaacgtttgcgacgtcggtcga;

(SEQ ID NO: 55)
    5'-tcgcaacgtttgcgacggcgctcga;

(SEQ ID NO: 56)
    5'-tcgcaacgtttgcgacgtcgttcga;

(SEQ ID NO: 57)
    5'-tcgcaacgtttgcgacggcgttcga;

(SEQ ID NO: 58)
    5'-tcgcaacgtttgcgacgtcgttcg;

(SEQ ID NO: 59)
    5'-tcgcaacgtttgcgacgtcgttcgg;

(SEQ ID NO: 60)
    5'-tcgcaacgtttacgacgtcggtcga;

(SEQ ID NO: 61)
    5'-tcgcaacgtttacgacggcgctcga;

(SEQ ID NO: 62)
    5'-tcgcaacgtttacgacgtcgttcga; and (SEQ ID NO: 63)
    5'-tcgcaacgtttacgacggcgttcga.
```

(5) The oligonucleotide according to any one of (1)-(4), wherein the internucleotide linkage(s) of the oligonucleotide is partially or fully chemically modified.
(6) The oligonucleotide according to (5), wherein the chemically-modified internucleotide linkage is a phosphorothioated.
(7) The oligonucleotide according to (6), wherein the oligonucleotide comprises a partially phosphorothioated oligonucleotide stretch selected from the group consisting of

```
                                    (SEQ ID NO: 16)
    5'-tCgcaacgtttgcgacgtcgttcgA-3';

(SEQ ID NO: 17)
    5'-tCgcaaCgtttgcgacgtcgttcgA-3';

(SEQ ID NO: 18)
    5'-tCgCaaCgtttgcgacgtcgttcgA-3';

(SEQ ID NO: 19)
    5'-tCgCaacgtttgCgaCgtcgttcgA-3';
```

-continued

```
                                (SEQ ID NO: 20)
5'-tCgCaacgtttgCgaCgtcgttCgA-3';

(SEQ ID NO: 21)
5'-tCgCaaCgtttgcgacgtCgttCgA-3';

(SEQ ID NO: 22)
5'-tCgCaaCgtttgCgaCgtCgttCgA-3';

(SEQ ID NO: 23)
5'-tCgCaaCgtttgcgacgtCggtCgA-3';

(SEQ ID NO: 24)
5'-tCgCaaCgtttgcgacggCgctCgA-3';

(SEQ ID NO: 26)
5'-tCgCaaCgtttgcgacggCgttCgA-3';

(SEQ ID NO: 27)
5'-tCgCaaCgtttgcgacgcCgttCgA-3';

(SEQ ID NO: 28)
5'-tCgCaaCgtttgcgacggCgtaCgA-3';

(SEQ ID NO: 29)
5'-tCgCaaCgtttgcgacggCgtgCgA-3';

(SEQ ID NO: 30)
5'-tCgCaaCgtttacgacgtCggtCgA-3';

(SEQ ID NO: 31)
5'-tCgCaaCgtttacgacgCgctCgA-3';

(SEQ ID NO: 32)
5'-tCgCaaCgtttacgacgtCgttCgA-3';

(SEQ ID NO: 33)
5'-tCgCaaCgtttGcgacgtCggtCgA-3';

(SEQ ID NO: 34)
5'-tCgCaaCgtttAcgacgtCggtCgA-3';

(SEQ ID NO: 35)
5'-tCgCaaCgtttGcgacggCgctCgA-3';

(SEQ ID NO: 36)
5'-tCgCaaCgtttAcgacggCgctCgA-3';

(SEQ ID NO: 37)
5'-tCgCaaCgtttGcgacgtCgttCgA-3';

(SEQ ID NO: 38)
5'-tCgCaaCgtttAcgacgtCgttCgA-3';

(SEQ ID NO: 39)
5'-tCgCaaCgtttGcgacgtCggtCgG-3';

(SEQ ID NO: 40)
5'-tCgCaaCgtttAcgacgtCggtCgG-3';

(SEQ ID NO: 41)
5'-tCgCaaCgtttGcgacggCgctCgG-3';

(SEQ ID NO: 42)
5'-tCgCaaCgtttAcgacggCgctCgG-3';

(SEQ ID NO: 43)
5'-tCgCaaCgtttGcgacgtCgttCgG-3'; and (SEQ ID NO: 44)
5'-tCgCanCgittAcgacgtCgttCgG-3';
``` wherein the capital letter denotes a nucleoside with no modified internucleotide linkage at 3', and the small letter denotes a nucleoside with an internucleotide linkage with phosphorothioation at 3'.

(8) The oligonucleotide according to (6), wherein the oligonucleotide comprises a partially phosphorothio-ated oligonucleotide stretch selected from the group consisting of,

```
                                (SEQ ID NO: 33)
5'-tCgCaaCgtttGcgacgtCggtCgA-3';

(SEQ ID NO: 34)
5'-tCgCaaCgtttAcgacgtCggtCgA-3';

(SEQ ID NO: 35)
5'-tCgCaaCgtttGcgacggCgctCgA-3'; and (SEQ ID NO: 36)
5'-tCgCaaCgtttAcgacggCgctCgA-3',
``` wherein the capital letter denotes a nucleoside with no modified internucleotide linkage at 3', and the small letter denotes a nucleoside with an internucleotide linkage with phosphorothioate at 3'.

(9) The oligonucleotide according to any one of (1)-(8), wherein the oligonucleotide is constituted with DNA.

(10) The oligonucleotide according to any one of (1)-(9), wherein the oligonucleotide is further deleted with, replaced with, or added with one or several nucleotide(s)

(11) The oligonucleotide according to any one of (1)-(10), wherein the oligonucleotide is comprised in an expression vector.

(12) The oligonucleotide according to any one of (1)-(10), wherein the oligonucleotide is circularized.

(13) The oligonucleotide according to any one of (1)-(10), wherein the oligonucleotide is linear.

(14) The oligonucleotide according to (13), wherein 3' end of the linear oligonucleotide has no phosphoric acid.

(15) A double-strand oligonucleotide comprising the oligonucleotide according to any one of (1)-(10) and a complementary strand oligonucleotide thereof.

(16) The oligonucleotide according to any one of (1)-(15), which is conjugated with active molecules.

(17) The oligonucleotide according to (16), wherein the active molecule is selected from the group consisting of (poly) peptides/antibodies and nucleic acids/oligonucleotides.

(18) The oligonucleotide according to (16) or (17), wherein the conjugation is made through a linker.

(19) The oligonucleotide according to (18), wherein the linker is selected from the group consisting of glycerol, (S)-(−)-1,2,4-Butanetriol, 1,3,5-Pentanetriol, cis,cis-1,3,5,-Cyclohexanetriol, cistrans-1,3,5-Cyclohexanetriol, 1,3,5-tris-(2-Hydroxyethyl) isocyanurate, Tetraethyleneglycol, and Hexaethyleneglycol, diols such as 1,3-propane diol or dodecane-1,12-diol, cyclohexanediol, cholesterol, nitroindol, triethylene glycol, hexaethylene glycol, d-spacer, PEG-spacer and alkyl linker.

(20) A pharmaceutical composition, comprising a therapeutically effective amount of the oligonucleotide according to any one of (1)-(19) and a pharmaceutical acceptable carrier.

(21) A pharmaceutical composition for prophylaxis or treatment of a target disease or disorder, comprising a therapeutically effective amount of the oligonucleotide according to any one of (1)-(19), wherein the target disease or disorder is any one selected from the group consisting of neoplasms, infectious disease, disease related to Th2/Th17, primary immunodeficiency disease, and Post-traumatic stress disorder (PTSD).

(22) The pharmaceutical composition according to (21), wherein the target disease or disorder is a neoplasm selected from the group consisting of malignant neoplasm, epithelial neoplasm or hematopoietic organ tumor, sarcoma, mesothelioma, benign tumor, dysplasia and metaplasia.

(23) The pharmaceutical composition according to (21), wherein the target disease or disorder is an infectious disease caused by microorganisms including viruses, bacteria, or fungi

(24) The pharmaceutical composition according to (21), wherein the target disease or disorder is a disease related to Th2/Th17 selected from the group consisting of asthma, atopic disease, allergy, multiple sclerosis, Inflammatory Bowel Disease including ulcerative colitis and Crohn disease, cutaneous lichen planus and Alzheimer's disease.

(25) The pharmaceutical composition according to (21), wherein the target disease or disorder is a primary immunodeficiency disease caused by IRAK4 deficiency, MyD88 deficiency, Unc93B deficiency or mutations in TLRs.

(26) The pharmaceutical composition according to (20) or (21), wherein the composition further comprises at least one active ingredient.

(27) The pharmaceutical composition according to (20) or (21), wherein the composition is co-administered with at least one active ingredient.

(28) The pharmaceutical composition according to (26) or (27), wherein the active ingredient is selected from the group consisting of anti-cancer drugs; molecular targeting drugs including tyrosine kinase inhibitors, angiogenesis inhibitors and proteasome inhibitors; anti-cancer antibody drugs; cytokines; vaccines; antibacterial agents: antifungal agents; antivirus agents; antiparasitic drugs; antibody drugs to neutralize toxin: agonists of other TLRs and combination thereof.

(29) The pharmaceutical composition according to (20) or (21), wherein the composition is administered to a subject through a dosage route selected from the group consisting of enteral administration, parenteral administration, topical administration and inhalation.

(30) The pharmaceutical composition according to (29), wherein the subject is human.

(31) The pharmaceutical composition according to (30), wherein the composition is administered to the subject to at 0.3-60 mg/day, preferably 1-30 mg/day, more preferably 2-8 mg/day.

(32) The pharmaceutical composition according to (20) or (21), wherein the composition is administered before or after adoptive immune cell therapies or surgical treatments including radiation therapy, cryoablation, radiofrequency ablation and photodynamic therapy (PDT).

(A1) Use of the oligonucleotides according to any one of (1)-(19) in the manufacture of a medicament for treatment or prophylaxis of a target disease or disorder selected from the group consisting of a neoplasm, infection, disease related to Th2/Th17, primary immunodeficiency disease, and Post traumatic stress disorder (PTSD).

(A2) Use of the oligonucleotides according to any one of (1)-(19) in the manufacture of a medicament for modulation of immune response in a subject.

(A3) The use according to (A1), wherein the target disease or disorder is a neoplasm selected from the group consisting of malignant neoplasm, epithelial neoplasm or hematopoietic organ tumor, sarcoma, mesothelioma, benign tumor, dysplasia and metaplasia.

(A4) The use according to (A1), wherein the target disease or disorder is an infectious disease caused by microorganisms including viruses, bacteria, or fungi (A5) The use according to (A1), wherein the target disease or disorder is a disease related to Th2/Th17 selected from the group consisting of asthma, atopic disease, allergy, multiple sclerosis, Inflammatory Bowel Disease including ulcerative colitis and Crohn disease, cutaneous lichen planus and Alzheimer's disease.

(A6) The use according to (A1), wherein the target disease or disorder is a primary immunodeficiency disease caused by IRAK4 deficiency, MyD88 deficiency. Unc93B deficiency or mutations in TLRs.

(A7) The use according to (A1) or (A2), wherein the medicament further comprises at least one active ingredient.

(A8) The use according to (A1) or (A2), wherein the medicament is co-administered with at least one active ingredient.

(A9) The use according to (A7) or (A8), wherein the active ingredient is selected from the group consisting of anti-cancer drugs; molecular targeting drugs including tyrosine kinase inhibitors, angiogenesis inhibitors and proteasome inhibitors; anti-cancer antibody drugs; cytokines; vaccines; antibacterial agents; antifungal agents; antivirus agents; antiparasitic drugs; antibody drugs to neutralize toxin; agonists of other TLRs and combination thereof.

(A10) The use according to (A1) or (A2), wherein the medicament is administered to a subject through a dosage route selected from the group consisting of enteral administration, parenteral administration, topical administration and inhalation.

(A11) The use according to (A10), wherein the subject is human.

(A12) The use according to (A11), wherein the medicament is administered to the subject at 0.3-60 mg/day, preferably 1-30 mg/day, more preferably 2-8 mg/day.

(A13) The use according to (A1) or (A2), wherein the medicament is administered before or after adoptive immune cell therapies or surgical treatments including radiation therapy, cryoablation, radiofrequency ablation and photodynamic therapy (PDT).

(B1) A method of treating or preventing a target disease or disorder in a subject, comprising administering the oligonucleotide according to any one of (1)-(19) to a subject, wherein the target disease or disorder is any one selected from the group consisting of a neoplasm, infection, disease related to Th2/Th17, primary immunodeficiency disease, and Post traumatic stress disorder (PTSD); preferably wherein the target disease or disorder is treated or prevented by activating NF-kB with the oligonucleotide in the subject.

(B2) The method according to (B1), wherein the target disease or disorder is a neoplasm selected from the group consisting of malignant neoplasm, epithelial neoplasm or hematopoietic organ tumor, sarcoma, mesothelioma, benign tumor, dysplasia and metaplasia.

(B3) The method according to (B1), wherein the target disease or disorder is an infectious disease caused by microorganisms including viruses, bacteria, or fungi (B4) The method according to (B1), wherein the target disease or disorder is a disease related to Th2/Th17 selected from the group consisting of asthma, atopic disease, allergy, multiple sclerosis, Inflammatory Bowel Disease including ulcerative colitis and Crohn disease, cutaneous lichen planus and Alzheimer's disease.

(B5) The method according to (B1), wherein the target disease or disorder is a primary immunodeficiency disease caused by IRAK4 deficiency, MyD88 deficiency, Unc93B deficiency or mutations in TLRs.

(B6) The method e according to (B1), wherein the oligonucleotide is co-administered with at least one active ingredient.

(B7) The method according to (B6), wherein the active ingredient is selected from the group consisting of anti-cancer drugs; molecular targeting drugs including tyrosine kinase inhibitors, angiogenesis inhibitors and proteasome inhibitors; anti-cancer antibody drugs; cytokines; vaccines; antibacterial agents; antifungal agenta; antivirus agents; antiparasitic drugs; antibody drugs to neutralize toxin; agonists of other TLRs and combination thereof.

(B8) The method according to (B1), wherein the oligonucleotide is administered to a subject through a dosage route selected from the group consisting of enteral administration, parenteral administration, topical administration and inhalation.

(B9) The method according to (B8), wherein the subject is human.

(B10) The method according to (B9), wherein the oligonucleotide is administered to the subject at 0.3-60 mg/day, preferably 1-30 mg/day, more preferably 2-8 mg/day.

(B11) The method according to (B1), further comprising a step of adoptive immune cell therapies or surgical treatments including radiation therapy, cryoablation, radiofrequency ablation and photodynamic therapy (PDT).

(C1) A method for stimulating an immune response in a subject comprising administering to a subject a therapeutically effective amount of the oligonucleotide according to any one of (1)-(19) to induce an inflammatory cytokine in the subject.

(C2) A method for redirecting Th2-biased immune response to Th1-biased immune response in a subject comprising administering to the subject a therapeutically effective amount of the oligonucleotide according to any one of (1)-(19) to induce inflammatory cytokines in the subject.

(C3) A method according to (C1) or (C2), wherein the inflammatory cytokine is selected from the group consisting of IL-6. TNF-$\alpha$, IFN-$\gamma$, and IL-12.

(D1) An oligonucleotide according to any one of (1)-(19) for use in the prophylaxis or treatment of a target disease or disorder, wherein the target disease or disorder is any one selected from the group consisting of a neoplasm, infectious disease, disease related to Th2/Th17, primary immunodeficiency disease, and Post-traumatic stress disorder (PTSD).

(D2) The oligonucleotide for use according to (D1), wherein the target disease or disorder is a neoplasm selected from the group consisting of malignant neoplasm, epithelial neoplasm or hematopoietic organ tumor, sarcoma, mesothelioma, benign tumor, dysplasia and metaplasia.

(D3) The oligonucleotide for use according to (D1), wherein the target disease or disorder is an infectious disease caused by microorganisms including viruses, bacteria, or fungi (D4) The oligonucleotide for use according to (D1), wherein the target disease or disorder is a disease related to Th2/Th17 selected from the group consisting of asthma, atopic disease, allergy, multiple sclerosis, Inflammatory Bowel Disease including ulcerative colitis and Crohn disease, cutaneous lichen planus and Alzheimer's disease.

(D5) The oligonucleotide for use according to (D1), wherein the target disease or disorder is a primary immunodeficiency disease caused by IRAK4 deficiency, MyD88 deficiency, Unc93B deficiency or mutations in TLRs.

(D6) The oligonucleotide for use according to (D1), wherein the oligonucleotide is co-administered with at least one active ingredient.

(D7) The oligonucleotide for use according to (D6), wherein the active ingredient is selected from the group consisting of molecular targeting drugs including tyrosine kinase inhibitors, angiogenesis inhibitors, proteasome inhibitors, anti-cancer antibody drugs and cytokines and combination thereof.

(D8) The oligonucleotide for use according to (D1), wherein the oligonucleotide is administered to a subject through a dosage route selected from the group consisting of enteral administration, parenteral administration, topical administration and inhalation.

(D9) The oligonucleotide for use according to (D8), wherein the subject is human.

(D10) The oligonucleotide for use according to (D9), wherein the oligonucleotide is administered to the subject at 0.3-60 mg/day, preferably 1-30 mg/day, more preferably 2-8 mg/day.

(D11) The oligonucleotide for use according to (D1), wherein the oligonucleotide is administered before or after adoptive immune cell therapies or surgical treatments including radiation therapy, cryoablation, radiofrequency ablation and photodynamic therapy (PDT).

(E1) Use of the oligonucleotide according to any one of (1)-(19) for treatment or prophylaxis of a target disease or disorder selected from the group consisting of a neoplasm, infection, disease related to Th2/Th17, primary immunodeficiency disease, and Post traumatic stress disorder (PTSD).

(F1) An in vivo or in vitro agent for modulation of immune response, comprising an effective amount of the oligonucleotide according to any one of (1)-(19).

Advantageous Effects of the Invention

The present invention can provide novel CpG oligonucleotides and therapeutic use of the oligonucleotides.

BRIEF DESCRIPTION OF DRAWINGS

FIG. 1 NF-kB activation and production of pro-inflammatory cytokines by TLR agonists in human plasmacytoid dendritic cell (pDC) cell line The CAL-1/NF-kB-GFP cell line was designed for monitoring the activity of NF-kB transcription factor in cell-based assays. Vector encoding GFP reporter gene driven by NF-kB consensus transcriptional response element was transfected into human pDC cell line, CAL-1.

A. CAL-1/NF-kB-GFP cells were stimulated with oligodeoxynucleotides (ODNs) of the present invention or positive control for 6 hours at 1 μM (micromolar). GFP expressions induced by the TLR9 agonists were shown by the dot plots.

B. A graph depicting ratio of the CAL-1/NF-kB-GFP cells activated with TLR9 by the ODNs. CAL-1/NF-kB-GFP cells were stimulated with ODNs of the present invention or positive controls for 6 hours at 0.3 μM. The ratio of GFP positive cells in the sample with CpG2395 was set to 100%. The activity of each ODN was calculated by the comparison of ratio of GFP positive cells with the one of CpG2395.

C. CAL-1/NF-kB-GFP cells were stimulated with ODNs of the present invention for 6 hours at 1.0 µM. The activity of A003 #delA was slightly weaker comparing to A003, but the activity was still much stronger than the one of authentic TLR9 agonist, CpG2395 (see FIG. 1A). The TLR9 activating activities of A003 #endG and A003 were in the similar levels, indicating that nucleoside at the 3' is not important for the activity.

D. CAL-1/NF-kB-GFP cells were stimulated with ODNs at 1 µM for 6 hours and the culture supernatants were recovered. The cytokine productions were evaluated by ELISA.

E, F. CAL-1/NF-kB-GFP cells were stimulated with ODNs for 6 hours at 1.0 µM. The GFP expressions were examined (FIG. 1E) and the cytokine productions in the culture supernatants were evaluated by ELISA (FIG. 1F). The activities of A003 and A013 were almost in the same levels comparing to each other, indicating that the change of the base in the oligonucleotide does not affect the activity.

G. CAL-1/NF-kB-GFP cells were stimulated with ODNs at 1.0 µM for 6 hours and the GFP expressions were examined. Each set of A001/A011, A002/A012, A003/A013 or A004/A014 exhibited the same activity to each other, indicating that the base change in each set of the ODNs does not affect the activity.

FIG. 2 Human TLR7 and TLR& activation

A. HEK blue™ TLR7 cells were stimulated with TLR agonists for 24 hours. As shown, TLR7 agonists Gardiquimod (GQ) and CL264 activated TLR7 and gave positive signals. In contrast, an authentic TLR9 agonist, CpG2395, and the ODNs of the present invention, A001-A004, at 0.3 µM could not activate TLR7 signaling pathway.

B. HEK blue™ TLR8 cells were stimulated with ODNs for 24 hours. As shown in the figure, TLR8 agonists, TL8-506 and CL075, activated TLR8 and gave positive signals. In contrast, CpG2395, and A001-A004 (0.3 µM) could not activate TLR8 signaling pathway.

FIG. 3 NF-kB activation and production of pro-inflammatory cytokines

A. CAL-1/NF-kB-GFP cells were stimulated with the ODNs of the present invention for 6 hours at 0.3 µM. CaaCg is important for human TLR9 activation.

B. CAL-1/NF-kB-GFP cells were stimulated with the ODNs of the present invention for 6 hours at 0.3 µM or 0.1 µM. Ratios of GFP positive cells (shown in %) are shown.

C. CAL-1/NF-kB-GFP cells were stimulated with the ODNs of the present invention for 6 hours at 0.3HM or 0.1 µM. A303, A603 and A703 showed higher activity than other tested ODNs, suggesting that existence of CaaCg is more important than numbers of Cg.

D. CAL-1/NF-kB-GFP cells were stimulated with the ODNs for 6 hours at 0.3 µM and the culture supernatants were recovered. The cytokine productions were evaluated by ELISA. A403 and A503 clearly showed lower levels of inductive activities of cytokine productions, suggesting that CaaCg is important for optimal TLR9 stimulation.

E. CAL-1/NF-kB-GFP cells were stimulated with the ODNs of the present invention for 6 hours at 0.3 µM. GFP positive cell ratio of CpG2395 was set to be 100% in the figure. The activity of each ODN was calculated from the GFP positive cell ratio comparing to the one of CpG2395. DV093 and DV094 showed lower TLR9 activities than A003, suggesting that specific caacg motif localized in A003, but not caacg motif in random location, is important for TLR9 activity.

F. CAL-1/NF-kB-GFP cells were stimulated with the ODNs for 6 hours at 0.3 µM. GFP positive cell ratio of Cp02395 was set to be 100%. The activity of each ODN was calculated from the GFP positive cell ratio compared to the one of CpG2395. Note that structural change from caacg stretch to CaaCg stretch in DV093 and DV094 by the change of internucleotide linkages does not strengthen TLR9 activity.

FIG. 4 Dispensable nucleotides in the 3' region of the ODNs of the present invention A, B. CAL-1/NF-kB-GFP cells were stimulated with the ODNs at 0.3 µM for 6 hours. Ratio of GFP positive cells (%) were shown in (B). An authentic TLR9 agonist CpG2006 showed much weaker in activity comparing to A601, A602. A603, A604, A605, A606 and A607 (B).

FIG. 5 Human TLR7 and TLR8 activation

A. HEK blue™ TLR7 cells were stimulated with the ODNs or the positive control for 24 hours. TLR7 agonist CL264 activated TLR7 and gave positive signal. In contrast, CpG2395, A601, A602 and A603 (0.3M) could not activate TLR7 signaling pathway.

B. HEK blue™ TLR8 cells were stimulated with the ODNs or the positive control for 24 hours. TLR8 agonist CL075 activated TLR& and gave positive signal. In contrast, CpG2395, A601, A602 and A603 (0.3HM) could not activate TLR8 signaling pathway.

FIG. 6 Negligible effect on the TLR9 activating activity by the changes in internucleotide linkages and base changes in the middle of the ODNs.

A. CAL-1/NF-kB-GFP cells were stimulated with A601, A601G, A602 or A602G (0.3 µM) for 3 hours.

B. CAL-1/NF-kB-GFP cells were stimulated with A601G, A611A, A602G or A612A (0.3 µM) for 3 hours.

C. CAL-1/NF-kB-GFP cells were stimulated with the ODNs for 3 hours at 0.3 µM. Ratio of GFP positive cells (%) was shown.

FIG. 7 Human TLR7 and TLR8 activation

A. HEK blue™ TLR7 cells were stimulated with TLR agonists for 24 hours. TLR7 agonist CL264 activated TLR7 and gave positive signal. In contrast, CpG2395, A601G, A611A, A602G and A612A (0.3 µM) could not activate TLR7 signaling pathway.

B. HEK blue™ TLR8 cells were stimulated with TLR agonists for 24 hours. TLR8 agonist CL075 activated TLR8 and gave positive signal. In contrast, CpG2395, A601G, A611A, A602G and A612A (0.3 µM) could not activate TLR8 signaling pathway.

FIG. 8 Activities inducing cytokine productions in human B cells or in human PBMCs A. HAL-01 cells were stimulated with the ODNs of the present invention for 24 hours at 1 µM. Cells were stained with anti-CD40 antibody (Ab) and anti-CD86 Ab. Induction of CD40 and CD86 expressions were evaluated with flow cytometer.

B. Human PBMCs were stimulated with the ODNs of the present invention (0.1 µM) for 24 hours and the cell proliferations were evaluated with WST-1 assay.

C. Human PBMCs were stimulated with the ODNs of the present invention (0.3 µM) for 24 hours and the culture supernatants were recovered. The cytokine productions were evaluated with ELISA.

FIG. 9 Agonistic activities on mouse cells

A. Mouse splenocytes were stimulated with the ODNs of the present invention for 24 hours and the supernatants were recovered. The cytokine productions were evaluated with ELISA.

B, C. Mouse splenocytes were stimulated with the ODNs of the present invention for 48 hours. The cell proliferations were evaluated with WST-1 assay. A601, A602 and A603 exhibited stronger activities than authentic TLR9 agonists, CpG2395 and CpG2006.

FIG. 10 in vivo anti-tumor activity

A. CT26 cells were inoculated to right flanks and the mice were kept un-treated for two weeks. Tumor volumes were measured and the mice were divided into three groups based on the tumor volumes. Administration of the ODNs of the present invention or PBS into peritumor regions was conducted on the grouping day (day 0) and repeated at day 2. The ODNs of the invention was administered twice in total during the study. The tumor volumes of each group mice were measured every two days.

B. Tumor volume of each mouse on each day.

C. The mean of body weight of the mice in each group during the study. No severe weight loss was observed in all the groups.

FIG. 11 Induction of memory of anti-tumor immunity

A. CT26 cells were inoculated to the right flanks and mice were kept un-treated for two weeks. Tumor volumes were measured and the mice were divided into three groups based on the tumor volumes. Administration of the ODNs of the present invention or PBS was started on the grouping day (day 0) and repeated on day 2. The ODNs of the invention were administered twice in total during the study. The tumor volumes of each group mice were measured every two days.

B. CT26 cells were re-inoculated to left flank of each group mice on day 14 and then the mice were kept un-treated. The tumor volumes in the left flanks were measured until 14 days after CT26 re-inoculation. Note that the mice treated with ODNs of the present invention rejected re-challenged tumor without any further treatment for 2 weeks, indicating that the ODNs of present invention induced memory of anti-tumor immunity.

FIG. 12 in vivo efficacy in lung metastasis model

In order to induce lung metastasis of CT26 cells, the cell suspension was intravenously injected into BALB/c mice ($5\times10^5$ cells/mouse) from the tail vein (day 0). On day 1, administrations of the ODNs of the present invention were started (subcutaneous injection to the skin of the back, 40 µg/50 µl/mouse). The ODNs of the same dose were re-administered on day 5. On day 18, the mice were sacrificed. The lung weights were measured and the metastatic tumor nodules in each lung from the mice were counted.

FIG. 13 Systemic effect against tumor metastasis

A. In order to induce lung metastasis of CT26 cells, the cell suspensions were intravenously injected to BALB/c mice ($5\times10^5$ cells/mouse) from the tail veins (day 0). On the next day of the tumor inoculation (day 1), administration of A602 was started. Two administration routes were tested. One is subcutaneous (S.C.) injection to the skin of the back and another is intradermal (I.D.) injection into the root of the ear (25 µg/mouse). Same dose of administrations were conducted on day 3 and day 5. On day 16, the mice were sacrificed and the metastatic tumor nodules in each lung from the mice were counted (graph in the right). Photographs: isolated lungs of the tested mice at day 16.

B. In order to induce liver metastasis of CT26 cells, the cell suspensions were injected to spleen ($1\times10^5$ cells/mouse, day 0). On day 2, the mice were divided into three groups based on the body weight and administration of A602 was started. Two administration routes, S.C. injection to the skin of the back and I.D. injection into the root of the ear (12.5 µg/mouse), were tested in this study. Same dose of administration was conducted on day 5, day 8 and day 12 as well. On day 20, the mice were sacrificed and the metastatic tumor nodules in each liver from the mice were counted.

FIG. 14 Elimination of B-ALL cells by activated PBMCs

A. Human PBMCs were co-cultured with human B-ALL cells, RCH-ACV, together with the ODNs of the present invention (0.1 µM) for 3 days and the whole cells were analyzed by flow cytometry after staining with CD19 and CD138 antibodies.

B. The ratios of RCH-ACV populations in the samples are depicted comparing to the non-stimulated sample which is set to 100%.

FIG. 15 Elimination of colon carcinoma cells by activated PBMCS

A. Human PBMCs ($5\times10^5$) were co-cultured with human colon carcinoma cells. COLO205, together with the ODNs of the present invention (0.1 µM) for 3 days and the whole cells were analyzed by staining with CD45 and CD24 antibodies.

B. The ratios of COLO205 populations in the samples are depicted comparing to the non-stimulated sample which is set to 100%.

FIG. 16 Effect on immune cells

A. Human PBMCs and mouse splenocytes were stimulated with the ODNs of present invention (0.15 µM) for 24 hours and the cell proliferations were evaluated with WST-1 assay.

B. Human PBMC's were co-cultured with cancer cells (RCH-ACV or COLO205) together with the ODNs of the present invention (0.1 µM) for 3 days. The elimination of cancer cells by human PBMCs was evaluated. The ratios of cancer cells in the sample are depicted by the comparison with non-stimulated sample which is set to be 100%.

PREFERRED EMBODIMENT

Unless otherwise noted, all terms in the present invention have the same meaning as commonly understood by one with ordinary skill in the art to which this disclosure belongs. The singular terms "a," "an," and "the" include plural referents unless context indicates otherwise. Similarly, the word "or" is intended to include "and" unless the context indicates otherwise. The term "a few" means numeral from 2 to 3 in this description. The term "several" means numeral from 2 to 6 in this description. In case of conflict, the present specification, including explanations of terms, will control. In addition, the materials, methods and examples are illustrative only and not intended to be limiting. Treat, treating or treatment shall have the same meaning without concerning the grammar. Similarly, prevent, preventing or prevention shall have the same meaning without concerning the grammar.

"nucleotide": A nucleotide constitutes a nucleic acid molecule such as DNA, RNA and chimeric molecule of DNA and RNA. A nucleotide may consist of a base, a phosphoric acid and a sugar. A nucleotide may be a phosphate ester of a nucleoside.

"nucleoside": A nucleoside may consist of a base and a molecule of sugar and is a component of a nucleotide. The nucleoside may include deoxyadenosine, deoxyguanosine, deoxythymidine, deoxycytidine, adenosine, guanosine, uridine and cytidine.

"oligonucleotide": An oligonucleotide is a polymer/oligomer of nucleotides which are joined with internucleotide linkage. The conformation of an oligonucleotide can be linear or circular.

"base": A base is one of components of a nucleotide and a nucleoside. Natural bases include two groups, purine bases such as guanine and adenine, and pyrimidine bases such as thymine, cytosine and uracil.

"sugar": A sugar is one of components of a nucleotide and a nucleoside. Basically, a sugar contained in DNA is a deoxyribose and a sugar contained in RNA is a ribose.

"internucleotide linkage": An internucleotide linkage shall mean an linkage between two adjacent nucleotides of a nucleic acid molecule.

A part of nucleotide, a nucleoside, a base and a sugar can be substituted or modified with another molecule which is referred as an analog of them. For example, a nucleotide may further include a non-natural artificial nucleotide such as PNA; base may further include non-natural base such as hypoxanthine (i.e., inosine as a nucleoside); and a sugar may include a non-natural artifact such as 2'-4' bridge in locked nucleic acid.

In the present application, "(sequence) motif" is prescribed only based on "base", while "(sequence) stretch" is prescribed based on "base", "sugar" and "internucleotide linkage".

The oligonucleotide of the present invention may be constituted with deoxyribonucleic acids with deoxyribose backbone, ribonucleic acids with ribose backbone or their mixture; the sugar backbones can also be replaced with synthetic molecules, such as locked nucleic acid (LNA), bridged nucleic acid (BNA), morpholino or peptide nucleic acid (PNA).

The oligonucleotide of the present invention may comprise chemically modified nucleosides and/or modified internucleotide linkages to enhance one or more properties, such as nuclease resistance, or pharmacokinetics.

The chemically modified nucleosides may comprise modified bases as following or the ones with related structures, but not limited to:

8-halogen (bromo, chloro, fluoro, iodo)-, 8-amino-, 8-thiol-, 8-thioalkyl-, 8-hydroxyl-, 8-aza-, 8-oxo- and other 8-substituted purines;

5-halogen (bromo, chloro, fluoro, iodo)-, 5-difluoromethyl-, 5-trifluoromethyl-, 5-hydroxy. 5-Carboxy-, 5-hydroxymethyl-, 5-bromovinyl-, 5-Formyl-, 5-aza-, 5-alkynyl-5-propynyl-, 5-(C1-C6)-alkyl-, 5-(C2-C6)-alkenyl-, 5-(C2-C6)-alkynyl-, and other 5-substituted pyrimidines;

5,6-dihydroxy-5,6-dihydrothymine, N6-methyl-adenine; N4-ethylcytosine, N4-alkylcytosine and other N4-substituted-cytosine;

2-mercapto-cytosine, iso-cytosine, pseud-isocytosine, 4-thio-uracil, dihydrouracil, pseudouracil, 2-thiouracil, 4-thiouracil, 2-aminopurine, 2,6-diaminopurine, 2-amino-6-chrolopurine, 2,4-diaminopurine, 6-thio-guanine, N2-methyl-guanine, N2-dimethylguanine and other N2-substituted guanines.

Modified nucleobases may also be bases replaced with other heterocycles, for example 7-deaza-adenine, 8-Aza-7-deaza-Adenine, 7-deaza-guanine, 2-aminopyridine and 2-pyridone.

Modified nucleobases may also comprise additional fused rings and the examples of such nucleobases are N6-etheno-adenosine, N4-ethenocytidine, N2-ethenoguanosine, and other related derivatives.

Internucleotide linkages are the covalent backbone linkages between nucleotides in oligo/poly nucleotides. Typically, natural internucleotide linkages are phosphodiester structure, but various modifications have been reported to affect chemical or physical properties of the molecules. The chemical modification in the modified internucleotide linkages which can be used in the oligonucleotide of the present invention comprise conversion of a natural phosphodiester structure into the following bond structures: phosphorothioate, phosphorodithioate, methylphosphonate, methylphosphorothioate, ethylphosphate, phosphonoacetate, alpha-hydroxybenzylphosphate, isopropyl-phenoxyacetate, boranophosphate, phosphonocarboxylate, alpha-hydroxybenzyl phosphonate, phosphate-(C1-C21)-O-alkylester, phosphate-[(C6-C12) aryl-(C1-C21)-O-alkyl]ester, phosphotriester, phosphotriesteramide, ether, acetal, thioether, thioacetal, phosphoramidate, siloxane, carbonate, carboxymethylester, acetamidate, carbamate, urea, thiourea, sulfonamide, or sulfonyl urea, carbonate, carboxymethyl, amide, ethylene oxide linker, sulfonate, thioformacetal, formacetal, oxime, methyleneimino, methyleneaminocarbonyl, methylenemethylimino (MMI), methylenehydrazo, methylenedimethylhydrazo (MDH), and methyleneoxymethylimino.

The oligonucleotide of the present invention can be, but not limited to, single-stranded deoxyribonucleic acid, a single-stranded ribonucleic acid or chimeric molecule thereof.

The oligonucleotide of the present invention can either be single strand, double strand or the hybrid of single and double strand. They can also form circular structure by connecting 5' and 3' ends of the single molecule; more than one oligonucleotide of this invention can be connected by covalent bonding or through distinctive linkers either at 5' or 3' end to form tandemly-connected elongated structures or multivalent structures. The oligonucleotides can be annealed intermolecularly or intramolecularly to form elongated structures, multimeric structures, or concatemers. The oligonucleotides can be bound to other molecules in order to form multimer. The oligonucleotide of the present invention can be bound to other oligonucleotides. The oligonucleotide of the present invention can be included in an expression vector including plasmid vectors and virus vectors.

The oligonucleotide of the present invention may comprise a CpG motif, namely non-methylated dinucleotides, cytosine and guanine.

The oligonucleotide of the present invention may comprise common sequence motifs, tcgcaacgtit (SEQ ID NO:1) and cgaeg, preferably, tcgcaacgttt-n-cgaeg-n-eg-nn-cg (SEQ ID NO:2), or more preferably, tegcaacgttt-r-cgacg-k-cg-bd-cg (SEQ ID NO:3); wherein each of a, t, c or g denotes a base, respectively corresponding to adenine, thymine/uracil, cytosine or guanine: n denotes any base; r denotes adenine or guanine; k denotes guanine or thymine/uracil, respectively; b denotes cytosine, guanine or thymine/uracil; and d denotes adenine, guanine or thymine/uracil. The oligonucleotide of the present invention may have r (adenine or guanine) at the 3' of the motif, forming tcgcaacgttt-r-cgaeg-k-cg-b n-cg-r (SEQ ID NO:4)

The oligonucleotide of the present invention may comprise phosphorothioated internucleotide linkages. Each of the phosphorothioated internucleotide linkages may comprise stereogenic α-phosphorus atom, resulting in the R or S diastereomer. The phosphorothioated internucleotide linkages may also comprise phosphorodithioate structures. The oligonucleotide of the present invention preferably comprises characteristic partially phosphorothioated stretch, CaaCg in the 5' regions of the oligonucleotides with partially phosphorothioated or phosphodiester internucleotide linkages, wherein the capital letter denotes a nucleoside with the unstabilized 3' internucleotide linkage, such as phosphodiester linkage without non-natural chemical modification, and the small letter denotes a nucleoside with the 3' internucleotide linkage being stabilized structure, such as phosphorothioate linkage.

The partially phosphorothioated version of oligonucleotide of the present invention may preferably comprise partially phosphorothioated stretch such as tCgCaaCgitt-n-cgacg-n-Cg-nn-C-g (SEQ ID NO:5), wherein the small letter denotes a nucleoside with the 3' internucleotide linkage being stabilized structure, such as phosphorothioate linkage.

The above-mentioned motifs or stretches are needed to be located in row in the same oligonucleotide; the motifs can be separated in the middle by an insertion/insertions of nucleotide(s), but the nucleotide(s) inserted in each location are preferably 1 or 2. The motifs mentioned above can be mutated, but the nucleotide(s) mutated in each motif are preferably 1 or 2. The motifs can be partially deleted at the ends up to 2 bases.

In one embodiment, the oligonucleotide of the present invention may be selected from the oligonucleotides with following sequence motifs shown in the Table 1, wherein the internucleotide linkages can be selected from natural (ex. phosphodiester) or synthetic ones (ex. phosphorothioation) or their mixture:

TABLE 1

| sequences | SEQ ID NOs |
|---|---|
| tcgcaacgtttgcgacgtcggtcga | SEQ ID NO: 64 |
| tcgcaacgtttgcgacggcgctcga | SEQ ID NO: 55 |
| tcgcaacgtttgcgacgtcgttcga | SEQ ID NO: 56 |
| tcgcaacgtttgcgacggcgttcga | SEQ ID NO: 57 |
| tcgcaacgtttgcgacgtcgttcg | SEQ ID NO: 58 |
| tcgcaacgtttgcgacgtcgttcgg | SEQ ID NO: 59 |
| tcgcaacgtttacgacgtcggtcga | SEQ ID NO: 60 |
| tcgcaacgtttacgacggcgctcga | SEQ ID NO: 61 |
| tcgcaacgtttacgacgtcgttcga | SEQ ID NO: 62 |
| tcgcaacgtttacgacggcgttcga | SEQ ID NO: 63 |

In another embodiment, the oligonucleotides of the present invention may be fully phosphorothioated in the internucleotide linkages. The examples of the oligonucleotides of the present invention are shown in the Table 2 as following:

TABLE 2

| sequences | SEQ ID NOs |
|---|---|
| tcgcaacgtttgcgacgtcggtcgA | SEQ ID NO: 6 |
| tcgcaacgtttgcgacggcgctcgA | SEQ ID NO: 7 |
| tcgcaacgtttgcgacgtcgttcgA | SEQ ID NO: 8 |
| tcgcaacgtttgcgacggcgttcgA | SEQ ID NO: 9 |
| tcgcaacgtttgcgacgtcgttcG | SEQ ID NO: 10 |

TABLE 2-continued

| sequences | SEQ ID NOs |
|---|---|
| tcgcaacgtttgcgacgtcgttcgG | SEQ ID NO: 11 |
| tcgcaacgtttacgacgtcggtcgA | SEQ ID NO: 12 |
| tcgcaacgtttacgacgcgctcgA | SEQ ID NO: 13 |
| tcgcaacgtttacgacgtcgttcgA | SEQ ID NO: 14 |
| tcgcaacgtttacgacggcgttcgA | SEQ ID NO: 15 |

The capital letters in the sequences above denotes a nucleoside or a nucleoside with phosphodiester bonding as the 3' internucleotide linkage, and the small letter denotes a nucleoside with phosphorothioation in the 3' internucleotide linkage.

In another embodiment, the oligonucleotides of the present invention may be partially phosphorothioated in the internucleotide linkages.

The oligonucleotides of the present invention may comprise a sequence motif caacg, preferably a partially phosphorothioated stretch, caaCg, Caacg or CaaCg, more preferably a partially phosphorothioated stretches, CaaCg.

The examples of such oligonucleotides are shown in the Table 3 as following:

TABLE 3

| Sequences and structures | SEQ ID NOs |
|---|---|
| tCgcaacgtttgcgacgtcgttcgA | SEQ ID NO: 16 |
| tCgcaaCgtttgcgacgtcgttcgA | SEQ ID NO: 17 |
| tCgCaaCgtttgcgacgtcgttcgA | SEQ ID NO: 18 |
| tCgCaacgtttgCgaCgtcgttcgA | SEQ ID NO: 19 |
| tCgCaacgtttgCgaCgtcgttCgA | SEQ ID NO: 20 |
| tCgCaaCgtttgcgacgCgttCgA | SEQ ID NO: 21 |
| tCgCaaCgtttgCgaCgtCgttCgA | SEQ ID NO: 22 |
| tCgCaaCgtttgcgacgtCggtCgA | SEQ ID NO: 28 |
| tCgCaaCgtttgcgacggCgctCgA | SEQ ID NO: 24 |
| tCgCaaCgtttgcgacggCgttCgA | SEQ ID NO: 26 |
| tCgCaaCgtttgcgacgcCgttCgA | SEQ ID NO: 27 |
| tCgCaaCgtttgcgacggCgtaCgA | SEQ ID NO: 28 |
| tCgCaaCgtttgcgacggCgtgCgA | SEQ ID NO: 29 |
| tCgCaaCgtttacgacgtCggtCgA | SEQ ID NO: 30 |
| tCgCaaCgtttacgacggCgctCgA | SEQ ID NO: 31 |
| tCgCaaCgtttacgacgtCgttCgA | SEQ ID NO: 32 |
| tCgCaaCgtttGcgacgtCggtCgA | SEQ ID NO: 33 |
| tCgCaaCgtttAcgacgtCggtCgA | SEQ ID NO: 34 |
| tCgCaaCgtttGcgacggCgctCgA | SEQ ID NO: 35 |
| tCgCaaCgtttAcgacggCgctCgA | SEQ ID NO: 36 |
| tCgCaaCgtttGcgacgtCgttCgA | SEQ ID NO: 37 |
| tCgCaaCgtttAcgacgtCgttCgA | SEQ ID NO: 38 |

TABLE 3-continued

| Sequences and structures | SEQ ID NOs |
|---|---|
| tCgCaaCgtttGcgacgtCggtCgG | SEQ ID NO: 39 |
| tCgCaaCgtttAcgacgtCggtCgG | SEQ ID NO: 40 |
| tCgCaaCgtttGcgacggCgctCgG | SEQ ID NO: 41 |
| tCgCaaCgtttAcgacggCgctCgG | SEQ ID NO: 42 |
| tCgCaaCgtttGcgacgtCgttCgG | SEQ ID NO: 43 |
| tCgCaaCgtttAcgacgtCgttCgG | SEQ ID NO: 44 |

The capital letters in the sequences above denotes a nucleoside or a nucleotide with phosphodiester bonding as the 3' internucleotide linkage, and the small letter denotes a nucleoside with phosphorothioation in the 3' internucleotide linkage.

The oligonucleotides of the present invention can bind to TLR9 and have the activity to enhance the signal transduction of the downstream of the receptor.

The TLR9 activation activity may be evaluated by the following phenomena as surrogate, but not limited to them (WO2014082254A, JP5011520B):

(i) strength of promoter activity of NF-kB binding oligonucleotide, described as the levels of GFP expression driven by the promoter in a cell such as CAL-1/NF-kB-GFP;

(ii) levels of cytokine productions from target cells; and (iii) levels of expressions of marker proteins, such as co-stimulatory molecules including CD40, CD80 or CD86 in the target cell such as antigen-presenting cells.

Activation of the target cells can be evaluated by the enhancement of the above-mentioned surrogate indicators. The enhancement of such markers shall be examined by the increase of the levels comparing to the normal status or the status without activating stimuli including addition of ligands.

Such an activity of the oligonucleotides of the present invention can be analyzed in the cultured cells, such as peripheral blood mononuclear cells (PBMC) or the established and immortalized cell lines. Such cell lines includes, HAL-1, and RCH-ACV in the place of B cells, CAL-1 (Maeda, T., et al., Int J Hematol, 2005. 81(2): p. 148-54). Gen2.2/Gen3 (Di Domizio, J., et al., Blood, 2009. 114(9): p. 1794-802) or PMDC05 (Narita, M., et al., Acta Haematol, 2008. 120(2): p. 91-9) in the place of plasmacytoid dendritic cells.

<Target Diseases>

The oligonucleotide of the present invention can be applied to prophylaxis or therapy of target diseases or disorders associated with immune response, or to modulation of immune response in a subject. The examples of target diseases or disorders are neoplasms, infectious diseases, Th2 or Th17-related diseases including the diseases occurring upon activation of Th2 or Th17, primary immunodeficiency disease, or post-traumatic stress disorder (PTSD).

The said neoplasms include (malignant) tumors, such as carcinomas (including malignant neoplasms, epithelial neoplasms, intraepithelial neoplasms, and hematopoietic tumors), sarcomas and mesotheliomas, benign tumors, dysplasia, and metaplasia. The said malignant tumors include, but not limited to, cancers such as lung cancer (small cell lung cancer and non-small cell lung cancer), colon cancer, rectal cancer, gastric cancer, esophagus cancer, pancreatic cancer, liver cancer, biliary tract cancer, bile duct cancer, renal cancer, pyeloureteral cancer, adrenal cancer, bladder cancer, testicle cancer, prostate cancer, penile cancer, thyroid gland cancer, uterus cancer, breast cancer, cervical cancer, endometrial cancer, ovarian cancer, melanoma, squamous cell cancer, neuroblastoma, oral cancer, acute lymphatic leukemia, acute myeloid leukemia, non-Hodgkin's lymphoma, Hodgkin's lymphoma, chronic myeloid leukemia, malignant lymphoma, and multiple myeloma.

The said sarcomas include, but not limited to, osteosarcoma, osteocystoma, aneurysmal bone cyst, osteoid osteoma, chondrosarcoma, poorly differentiated round/spindle cell tumors (includes ewing sarcoma), hemangioendothelioma, angiosarcoma, fibrosarcoma/myofibrosarcoma, chordoma, adamantinoma, liposarcoma, leiomyosarcoma, malignant peripheral nerve sheath tumor, rhabdomyosarcoma, synovial sarcoma, malignant solitary fibrous tumor, atypical lipomatous tumor, dermatofibrosarcoma protuberans, malignant solitary fibrous tumor, inflammatory myofibroblastic tumor, low-grade myofibroblastic sarcoma, fibrosarcoma (includes adult and sclerosing epithelioid varieties), myxofibrosarcoma, low-grade fibromyxoid sarcoma, giant cell tumor of soft tissues, malignant glomus tumor, rhabdomyosarcoma, hemangioendothelioma, angiosarcoma of soft tissue, extraskeletal osteosarcoma, gastrointestinal stromal tumor (gist), malignant peripheral nerve sheath tumor, malignant triton tumor, malignant granular cell tumor, malignant ossifying fibromyxoid tumor, stromal sarcoma, myoepithelial carcinoma, malignant phosphaturic mesenchymal tumor, epithelioid sarcoma, alveolar soft part sarcoma, clear cell sarcoma of soft tissue, extraskeletal myxoid chondrosarcoma, extraskeletal ewing sarcoma, desmoplastic small round cell tumor, extrarenal rhabdoid tumor, perivascular epithelioid cell tumor, intimal sarcoma, pleomorphic sarcoma and round cell sarcoma.

The said mesotheliomas include, but not limited to, pericardial mesothelioma, peritoneal mesothelioma, and pleural mesothelioma.

The said dysplasias include, but not limited to, myelodysplastic syndrome and cervical dysplasia.

The oligonucleotide of the present invention shows efficacy against target diseases based on the activation of immunity against malignant cells. If being used alone, it is expected that the efficacy would be higher when they are used against neoplasms with high immunogenicity. The neoplasms with high immunogenicity include, but not limited to, the cancer cells which express neoantigens, which are produced by mutations of the genes occurring during the course of tumorigenic steps; such cancers include the ones with deficiency in mismatch repair (dMMR) or microsatellite-instability-high (MSI-H) (Sargent, D. J., et al., J Clin Oncol, 2010. 28(20): p. 3219-26; Passardi, A., et al., Int J Mol Sci, 2017. 18(6): E1324).

The oligonucleotide of the present invention can activate pDC's through activation of TLR9. The activated pDCs further activate various other immune cells through interferons. Thus the oligonucleotide of the present invention can be applied to prophylaxis or therapy of various infectious diseases caused by microorganisms including viruses, bacteria, and fungi.

The viruses causing infectious diseases include, but not limited to, molluscum contagiosum virus, herpes simplex virus (HSV), chickenpox virus, herpes zoster virus, rotavirus, human papilloma virus, cytomegalovirus (CMV), poliovirus, coxsackievirus, rhinovirus, rubella virus, measles virus, influenza virus, mumps virus, respiratory syncytial (RS) virus, hepatitis virus and human immunodeficiency virus (HIV). Among those viruses, some viruses, such as CMV, HIV, influenza virus, HSV, Hepetitis B virus (HBV), or Hepatitis C virus (HCV), are reported to activate host immunity directly through binding to TLR9 (Swiecki, M., et al., Immunol Rev, 2010. 234(1): p. 142-62).

The bacteria causing infectious diseases are categorized into gram-negative and gram-positive, but the present invention can be applied to the bacteria of either of the group. It is at least reported that TLR9 is necessary for the activation of innate immunity against gram-negative bacteria (Bhan, U., et al., J Immunol, 2007. 179(6): p. 3937-46). The gram negative bacteria includes, but not limited to, *Neisseria gonorrhea, Neisseria meningitides. Hemophilus parainfluenzae, Escherichia coli, Pseudomonas aeruginosa, Chlamydia trachomatis*, and *Yersinia pestis. Moraxella catarrhalis, Haemophilus ducreyi, Bordetella pertussis, Bordetella parapertussis, Bordetella bronchiseptica, Citrobacter. Salmonella enterica* subsp. *enterica* serovar *Typhi, Salmonella enterica* subsp. *enterica* serovar Paratyphi A, *Salmonella enterica* subsp. *enterica* serovar Paratyphi B. *Salmonella Typhimurium, Salmonella enterica* serovar *Enteritidis, Shigella dysenteriae, Shigella frexneri, Shigella sonnei, Klebsiella pneumoniae, Klebsiella oxytoca, Enterobacter, Serratia, Hafnia, Proteus, Morganella, Providencia, Yersinia, Campylobacter, Vibrio cholera, Vibrio parahaemolyticus, Pseudomonas, Xanthomonas, Acinetobacter, Flavobacterium, Brucella, Legionella, Veillonella, Bacteroides* and *Fusobacterium.*

The infectious diseases caused by fungi include, but not limited to, Cryptococcosis, Candiasis, Aspergilosis, pneumonia caused by *Pneumocystis carinii*, Dermatophytosis caused by *Trichophyton*, and skin infection by *Tinea versicolor*. It is indeed reported that DNAs or RNAs derived from fungi are recognized by mammalian TLR9 (Kasperkovitz, P. V., et al., Infect Immun, 2011. 79(12): p. 4858-67; Patin, E. C., et al., Semin Cell Dev Biol, 2019. 89: p. 24-33).

The diseases related to Th2/Th17 are the diseases caused by the suppression of Th1 and activation of Th2 and/or Th17; the diseases include but not limited to asthma, atopic disease (dermatitis, eczema), allergies, multiple sclerosis, Inflammatory Bowel Disease including ulcerative colitis and Crohn disease, cutaneous lichen planus and Alzheimer's disease.

Primary Immunodeficiency diseases are disorders in which a part of the immune system is missing innately or does not function properly and it is known that the patients of the diseases are especially susceptible to the infections. It is well expected that the oligonucleotides of the invention will show efficacy especially in the patients lack functional TLR-related systems, such as the patients with IRAK4 deficiency, MyD88 deficiency. Unc93B deficiency or mutations in TLRs, but the efficacy is not limited in such diseases, as the oligonucleotides of the invention are expected to activate immunity broadly against infectious diseases.

Post-traumatic stress disorder (PTSD) is one of the diseases reported to be ameliorated by the TLR9 agonist and the disease is also considered to be one of the target diseases (Zimmerman, G., et al., Transl Psychiatry, 2012. 2: p. e78).

The oligonucleotides of the present invention can be used as one of the active ingredients of the pharmaceutical composition administered to the patients suffering from above-mentioned target diseases or disorders, but the oligonucleotides of the invention can also be applied to the subject for the prophylactic purpose of the above-mentioned target diseases.

The oligonucleotides of the present invention can be connected with other active molecules possibly through distinctive linkers. For example, the binding of pharmaceutical compounds for co-administration may ease co-administration; binding of lipid or pegylation may improve tissue distribution or pharmacokinetics. It is reported that pegylation of oligonucleotides elongate in vivo duration in a subject by lowering kidney clearance.

The oligonucleotides of the present invention can also be conjugated with some organic compounds such as Vitamin E (α-tocopherol) or Vitamin D in the aim of improvement of pharmacokinetics, such as in vivo half-life or cellular absorption (Winkler, J., Ther Deliv, 2013. 4(7): p. 791-809).

In order to connect the oligonucleotides of the present invention with other organic or inorganic moieties, an organic chemical compound, a linker, can be used; the linker, includes but not limited to glycerol, (S)-(−)-1,2,4-Butanetriol, 1,3,5-Pentanetriol, cis,cis-1,3,5,-Cyclohexanetriol, cistrans-1,3,5-Cyclohexanetriol, 1,3,5-tris-(2-Hydroxyethyl) isocyanurate, Tetraethyleneglycol, and Hexaethyleneglycol, diols such as 1,3-propane diol or dodecane-1,12-diol, cyclohexanediol, cholesterol, nitroindol, triethylene glycol, hexaethylene glycol, d-spacer, PEG-spacer and alkyl linker. The linker moiety can also be constituted with amino acids, nucleotides and/or their derivatives.

The linkers can also be used to make non-covalent bonds. The linkers include but not limited to biotin-avidin, SPB (succinimidyl-14-(psoralen-8-yloxy)]-butyrate) which intercalate into a nucleic acid, nucleic acids whose sequences are complementary and bind with each other, and protein-protein interaction such as coiled-coil structure . . .

In one embodiment, the oligonucleotides of the present invention can be used in combination with each other, with other oligonucleotides with similar mechanism of function, with other organic compounds, such as (poly) peptides/antibodies or nucleic acids/oligonucleotides, or inorganic compounds, such as cytotoxic agents, which are often used for improvement or modification of physical properties of drugs. Such combination can be generated either with or without covalent bonding.

The oligonucleotides of the present invention can be obtained from existing nucleic acid sources (e.g., genomic or cDNA), but are preferably synthetic. The oligonucleotides of the invention can be synthesized by a variety of automated nucleic acid synthesizers available in the market. These oligonucleotides are referred to as synthetic oligonucleotides.

The oligonucleotides of the present invention may be administered alone or co-administered with one or more of other active ingredients simultaneously or in sequence. The oligonucleotides of the present invention may also be utilized simultaneously or in sequence with one or more of other therapeutic methods.

The oligonucleotides of the present invention can be co-administered with conventional anti-cancer drugs or medications to alleviate various symptoms occurring along with tumor formation. The examples of the conventional anti-cancer drugs include, but not limited to: antibiotics, such as anthracycline or mytoxantrone; platinum; alkylating agents; antimetabolites; drugs for hormone therapy; phyto-alkaloids, such as *vinca* alkaloids; taxanes such as paclitaxel or docetaxel; and topoisomerase inhibitors, such as irinotecan or etoposide.

The oligonucleotides of the present invention can also be co-administered to the subjects in need with other molecular targeting drugs targeting biological characteristics of cancer cells; molecular targeting drugs include tyrosine kinase inhibitors, angiogenesis inhibitors or proteasome inhibitors. The examples of the molecular targeting drug include, but not limited to:

everolimus (Afinitor), tamoxifen (Nolvadex), toremifene (Fareston), fulvestrant (Faslodex), anastrozole (Arimidex), exemestane (Aromasin), lapatinib (Tykerb), letrozole (Femara), palbociclib (Ibrance), ribociclib (Kisqali), neratinib maleate (Nerlynx), abemaciclib (Verzenio), olaparib (Lynparza), regorafenib (Stivarga), imatinib mesylate (Gleevec), Lanreotide acetate (Somatuline Depot), sunitinib (Sutent), sorafenib (Nexavar), pazopanib (Votrient), temsirolimus (Torisel), axitinib (Inlyta), cabozantinib (Cabometyx), lenvatinib mesylate (Lenvima), Tretinoin (Vesanoid), dasatinib (Sprycel), nilotinib (Tasigna), bosutinib (Bosulif), ibrutinib (Imbruvica), idelalisib (Zydelig), venetoclax (Venclexta), ponatinib hydrochloride (Iclusig), midostaurin (Rydapt), enasidenib mesylate (Idhifa), inotuzumab ozogamicin (Besponsa), tisagenlecleucel (Kymriah), ivosidenib (Tibsovo), duvelisib (Copiktra), Sorafenib (Nexavar), crizotinib (Xalkori), erlotinib (Tarceva), gefitinib (Iressa), afatinib dimaleate (Gilotrif), ceritinib (LDK378/Zykadia), osimertinib (Tagrisso), alectinib (Alecensa), brigatinib (Alunbrig), trametinib (Mekinist), dabrafenib (Tafinlar), dacomitinib (Vizimpro), denileukin diftitox (Ontak), vorinostat (Zolinza), romidepsin (Istodax), bexarotene (Targretin), bortezomib (Velcade), pralatrexate (Folotyn), siltuximab (Sylvant), idelalisib (Zydelig), belinostat (Beleodaq), copanlisib hydrochloride (Aliqopa), acalabrutinib (Calquence), carfilzomib (Kyprolis), panobinostat (Farydak), ixazomib citrate (Ninlaro), ruxolitinib phosphate (Jakafi), Cabazitaxel (Jevtana), enzalutamide (Xtandi), abiraterone acetate (Zytiga), radium 223 dichloride (Xofigo), apalutamide (Erleada), Vismodegib (Erivedge), sonidegib (Odomzo), vemurafenib (Zelboraf), cobimetinib (Cotellic), alitretinoin (Panretin), encorafenib (Braftovi), binimetinib (Mektovi), cemiplimab-rwlc (Libtayo), alitretinoin (Panretin), and vandetanib (Caprelsa).

The oligonucleotides of the present invention may also be co-administered to the subjects with the anti-cancer antibody drugs. It is expected that co-administration with the ODN of the present invention synergistically enhances the activity antibody drugs which especially utilizes immune system to attack cancer cells. The examples of such antibody drugs include but not limited to:

(i) antibody drugs comprising single species of antibody: trastuzumab (Herceptin), alemutuzumab (Campath), bevacizumab (Avastin), pertuzumab (Perjeta), cetuximab (Erbitux), panitumumab (Vectibix), necitamumab (Portrazza), Dinutuximab (Unituxin), ramucirumab (Ciramza), olaratumab (Lartruvo), ipilimumab (Yervoy), nivolumab (Opdivo), pembrolizumab (Keytruda), atezolizumab (Tecentriq), denosumab (Xgeva), durvalumab (Imfinzi), avelumab (Bavencio), Ibritumomab tiuxetan (Zevalin), brentuximab vedotin (Adcetris), obinutuzumab (Gazyva), mogamulizumab-kpkc (Poteligeo), daratumumab (Darzalex), elotuzumab (Empliciti), rucaparib camsylate (Rubraca), niraparib tosylate monohydrate (Zejula), Anti-OX40;

(ii) antibody drugs comprising bispecific antibody: blinatumomab (Blincyto);

(iii) antibody drugs comprising Antibody-drug conjugate, ADC: ibritumomab tiuxetan (Zevalin), brentuximab vedotin (Adcetris), Ado-trastuzumab emtansine (Kadcyla), gemtuzumab ozogamicin (Mylotarg); and (iv) ziv-aflibercept (Zaltrap)

The oligonucleotides of the present invention may also be co-administered with cytokines such as GM-CSF. IFN-α, IFN—B or IFN-γ, which are already used in the standard care of the cancer therapies.

The oligonucleotides of the present invention may be utilized along with surgical procedures including radiation therapies, radio frequency ablation, cryoablation (Aarts, B. M., et al., Insights Imaging, 2019. 10(1): p. 53), or photodynamic therapy (PDT) after the administration of photosensitizer.

It is expected that the combination with the administration of oligonucleotides of the present invention will show synergistic efficacy, considering that especially PDT was reported to upregulate anti-cancer immunity (Kleinovink, J. W. et al., Cancer Immunol Res, 2019, 5(10): p. 832-838).

The oligonucleotides of the present invention may be administered as active ingredients in the adjuvant or neo-adjuvant setting (O'Donnell, J. S., et al., Clin Cancer Res, 2019, 25(19): p. 5743-5751).

The oligonucleotides of the present invention may also be used in combination with adoptive immune cell therapies. (also known as adoptive cell transfer (ACT)) such as chimeric antigen receptor T (CAR-T)-cell therapy (axicabtagene ciloleucel (Yescarta®) or tisagenlecleucel (Kymriah)), tumor-infiltrating lymphocyte (TIL) therapy, dendritic cell therapy or NK cell therapy. The ODN of the present invention may also be combined with the therapies using onco-lytic viruses, which utilizes artificially modified virus to lyse tumor mass (Davola, M. E., et al., Oncoimmunology, 2019. 8(6): p. e1581528; Sivanandam, V., et al., Mol Ther Onco-lytics, 2019. 13: p. 93-106; Raja, J., et al., J Immunother Cancer, 2018. 6(1): p. 140; Martinez-Quintanilla, J., et al., J Clin Invest, 2019. 130: p. 1407-1418; Harrington, K., et al., Nat Rev Drug Discov, 2019. 18(9): p. 689-706).

The oligonucleotides of the present invention may be used in combination with therapeutic vaccines, which is expected to enhance the immunity necessary for the therapies. Therapeutic vaccines are a class of vaccine used for the therapeutic purpose of existing diseases. Such therapeutic vaccines include not only vaccines prepared by weakened or detoxi-fied microorganisms, but also ex vivo cell vaccine prepared by ex vivo treated cells, and in vivo vaccine which activates immunity, such as anti-cancer immunity, by activating target immune cells. Ex vivo cell vaccine comprises Sipuleucel-T (Provenge), which is prepared from autologous or allogenic dendritic cells, or GVAX, which is prepared by modifying autologous or allogenic cancer cells. Loading of the antigens to such dendritic cells may be achieved by placing antigens including peptides, recombinant proteins, or tumor lysate, in contact with the dendritic cells in ex vivo culture, but may also be achieved by fusing cells expressing antigens (ex, cancer cells) with dendritic cells (Hollingsworth, R. E., et al., NPJ Vaccines, 2019. 4: p. 7).

The oligonucleotides of the present invention may be used in combination with a group of in vivo vaccines. In vivo vaccines may comprise tools for delivery to the target antigen-presenting cells (APCs) combined with antigens such as cancer antigens or virus antigens; the target proteins for the tools for delivery to APCs include cell surface proteins as following:

Dendritic cells: DEC20S, CDIIc, DC-SIGN, mannose receptor, TLRs, CD91 B cells: CD180, BCR, CD21, CD19

Plasmacytoid dendritic cells (pDCs): CD32, CLEC12a, BDCA2, DCIR, TLR9

The antigens used for the in vivo vaccines may include peptides or recombinant proteins comprising cancer anti-gens, which will be described later, or virus antigens; polynucleotides coding antigens may be utilized for the direct expression of antigens in such target APCs.

Prophylaxis cancer vaccines include, Hepatitis B virus vaccine, human papilloma virus (HPV) vaccine, such as Gardasil or Cervarix. It is also expected that the oligonucleotides of the present invention enhances prophylaxis activities of the marketed vaccines or the ones at premarket stages.

The oligonucleotides of the present invention may be utilized for the prophylaxis or therapies for the infectious diseases. The oligonucleotides may also be mixed with the vaccine composition as an adjuvant. Otherwise, the oligonucleotides may be administered to the subject in combination with the pharmaceutical composition for the treatment of infectious diseases including antibacterial agents, antifungal agents, antivirus agents, antiparasitic drugs, vaccines, antibody drugs to neutralize toxin.

The vaccines, which are used for the prophylaxis or therapy of infectious diseases, include the ones of the following categories:

Live, attenuated vaccines, which contain an weakened version of the living microbe.

Inactivated vaccines, which contain killed microbes, but retains antigenicity.

Subunit vaccines, which only contain antigens that stimulate immune system most efficiently.

Toxoid vaccines, which are aimed for the detoxification of the toxins from microbes.

Conjugate vaccines, which are specialized kinds of subunit vaccines, allowing establishment of immunity against microbes with weak immunity by conjugating other subunits with stronger immunogenicity.

Nucleic acid vaccines, which make the body cells to produce antigens achieving further in vivo immunization.

Recombinant vector vaccines, which carry genetic information of recombinant antigens in order to stimulate immunity against target microbes.

The example of the vaccines which may be used in combination with the oligonucleotide of the present invention are: BCG vaccine, cholera vaccine, Diphtheria vaccine, *Haemophilus influenzae* vaccine, Hepatitis A vaccine, Hepatitis B vaccine, Human Papillomavirus vaccine, pandemic HINI Influenza vaccine, seasonal Influenza vaccine, Japanese Encephalitis vaccine, Measles vaccine, Mumps vaccine, Meningococcal vaccine, Pneumococcal vaccine, Pertussis vaccine, Polio Vaccine, Rabies vaccine, Rotavirus vaccine, Rubella vaccine, Tetanus Toxoid vaccine, Typhoid vaccine, and Yellow Fever vaccine.

Recently, there are a class of medicines called immune checkpoint inhibitors (CPIs) eagerly developed, which affects immune checkpoint molecules, a group of proteins regulating immunity, to stimulate immunity necessary for the treatment of target diseases. The oligonucleotides of the present invention may be used with CPIs to enhance efficacy of CPIs synergistically through the activation of antigen-presenting cells related to immune checkpoint processes.

The examples of the target molecules of the immune checkpoint inhibitors are: PD-1. PD-L1, PD-L2, CD28, CD80, CD86, ICOS, B7RP1 (ICOSL), B7-H3 (CD276), B7-H4 (VTCN1), CD28H, B7-HS VISTA, BTLA, HVEM, CD40L, CD40, OX40, OX40L, CD137, CD137L, CD27, CD70, TIM3, GAL9, GITR, GITRL, LAG-3, MHC-II, CD47, ADORA2A (adenosine A2A receptor) and adenosine (Pardoll, D. M., Nat Rev Cancer. 2012. 12(4): p. 252-64).

The therapies or drugs which suppress the activity of immunosuppressive immune cells such as Tregs. Tumor associated macrophages (TAMs) or MDSCs may also be used for combination therapy with the oligonucleotides of the present invention. The examples of target molecules or pathways affected by such therapies or drugs are:

Tregs-Cytotoxic T-lymphocyte antigen-4 (CTLA-4), TGFbeta (TGFβ), IL-10, IL-35, ICOS, and lymphocyte activation gene-3 (LAG-3), Indoleamine 2, 3-dioxygenase (IDO), tryptophan 2, 3-dioxygenase (TDO), CD39, CD73, PI3K, Atg7 and AtgS TAMs-CCL2-CCR2 axis and CSF1/CSF1 receptor (CS-FIR) signaling MDSCs-PDE-S, COX-2, HDAC, STAT3, CCL2/CCR2, VEGF-A/MET/TIE2/VEGFR2 pathway, IL-8/CXCR1/2, Galectin-1 (Gal-1).

The therapies or drugs which remove such immunosuppressive immune cells can also be used for combination with the oligonucleotides of the present invention. Examples of the cell surface marker proteins which can be used for the depletion of such cells are as following:

Tregs-CD25, CTLA-4, PD-1, ICOS, GITR, OX40, CD15s, CCR4, and CCR8 TAMs-CD206, Legumain, scavenger receptor A and CD52

(Ohue, Y., et al., Cancer Sci, 2019. 110(7): p. 2080-2089; Yang, L., et al., J Hematol Oncol, 2017, 10(1): p. 58; Gabrilovich, D. I., Cancer Immunol Res, 2017, 5(1): p. 3-8;

Ding A. S. et al., Front Immunol, 2019, 10: p. 1715)

The oligonucleotides of the present invention can be used along with antigen proteins, peptides, glycoconjugates or other organic substances in the aim of enhancement of specific antigenic reactions against target diseases. The examples of the antigenic substances as below:

AFP, AKAP-4, ALK, Androgen receptor, B7H3, BAGE, bcr-abl, BMLF1, BmpA, BmpB, BOR1S, BRLF1, BZLF1, Carbonic anhydrase IX, Catalase B, CDC27, CDCA1, CDH3, CDK4, CEA, crf1, Cyclin B1, CYP1B1, DEPDC1, EBNA1, EBNA-1, EGFRVIII, Envelope Glycoprotein D, EpCAM, EphA2, EphA3, ERG, ETV6-AML, FAP, Fos-related antigen 1, FOXM1, Fucosyl GM1, GD2, GD3, Gell, GloboH, GM3, gp 100, GPC3, HA, HBV proteins, HCV proteins, HER2, Hexon, HJURP, HMWMAA, HPV-16 E6, HPV-16 E7, HPV-18 E7, idiotype of the surface Ig, IE-1, KIF20A, KOC1, KSV proteins, Large T antigen, Small T antigen, LCK, Legumain, LMP1, LMP2, MAD-CT-1, MAD-CT-2, MAGE, MAGE-3, MAGE-A1, MAGE-A4, MAM-A, Melan-A/MART-1, MELK, MELOE-1/2, Mesothelin, ML-IAP, MP1, MP2, MP65, MPHOSPH1, MUC1, Mucin-1, MYCN, NA, NA17, NeuGcOM3, Non-structural proteins NS4, Non-structural proteins NS5, NY-BR-1, NY-ESO-1, ospA, ospB, ospC, OY-TESI, p53, Page4, PAP, PAX3, PAX5, PDGFR-beta, penton, PLAC1, pmel17, pmp20, Polysialic acid, pp 65, PRAME, prostate-specific membrane antigen 10, Prostein, Proteinase3 (PRI), PSA, PSCA, PSMA, Ras, RGS5, RhoC, RM2, RNF43, RORI, Sarcoma translocation breakpoints, SART3, Select, Serine protease NS3, SHMP, sLe, SOD, Spermi protein 17, SSX2, STEAPI, STn, Survivin, TARP, Tax protein, telomerase, telomerase, TERT, Tie 2, TM4SF5, Tn, TOMM34, triosephosphate isomerase, TRP1, TRP2, TTK, tyrosinase, tyrosinase-related protein 1, tyrosinase-related protein 2, URLC10, VEGFR2, Virus capsid proteins, Virus core protein, Virus nucleoprotein, WT1, XAGE 1, alpha-actinin-4 and beta-catenin. Neoantigen is also a good candidate being used as an antigenic substance; neoantigen is an antigen newly formed by the in vivo process, such as mutagenesis occurring during tumor formation or produced from infectious foreign substances, which comes to be recognized by the own immune system.

Anticancer chemotherapy drugs, especially drugs inducing immunogenic cell death (ICD), may be co-administered with the oligonucleotides of the present invention, in order to show synergistically-enhanced efficacy. The examples of the drugs inducing ICD are: anthracyclins including mitoxantrone, Platinum-based anti-cancer drugs including Oxaliplatin, Cisplatin, Carboplatin, Nedaplatin, Triplatin tetranitrate, Picoplatin, Satraplatin (Hato, S. V., et al., Clin Cancer Res, 2014. 20(11): p. 2831-7).

Other drugs which are known for the property of activation of anti-cancer immunity, such as indoleamine 2,3-dioxygenase (IDO) inhibitors (Prendergast, G. C., et al., Cancer Res, 2017. 77(24): p. 6795-6811) or proteasome inhibitors including Bortezomib (Spisek, R., et al., Blood, 2007. 109(11): p. 4839-45; Chang, C. L., et al., J Immunol, 2012. 189(6): p. 3209-20) may be co-administered with the oligonucleotides of the present invention in order to show synergistic efficacy.

The oligonucleotides of the present invention can be co-administered with other TLR9 agonists or agonists for other TLRs, such as TLR3, 4, 8 or 7. The oligonucleotides of the present invention can also be used in combination with enhancers of intracellular nucleotide sensor signaling pathways, such as cGAS-STING pathway, or RIG-I/MDA5 pathway (Bode, C., et al., Eur J Immunol, 2016. 46(7): p. 1615-21; Iurescia, S., et al., Front Immunol, 2018. 9: p. 711), as those pathways have the target molecules in common with TLR9, such as IFN-α or NF-kB and it is expected to show synergistic effect when activated simultaneously. The examples of molecules activating each receptor are as following:

TLR3 agonist: Rintatolimod, Poly C 3SBIO, Poly(I: C), Hiltonol

TLR4 agonist: ALD046, CRX527, CRX675, G100, Lipid A, GSK1795091, OM174, PGN007

TLR7 agonist; Vesatolimod, VML600, 852A, NKTR262, TMX101, GS9620. RG7795, DSP0509, PF4878691, RG7854, RG7863. TMX202, TQA3334

TLR8 agonist: GS-9688, VTX 2337

TLR9 agonist: Heplisav, SD-101, IMO2125, IMO2055, MGN1703, MGN1706, CPG 7909, Litenimod, AST008, DUK-CPG-001, Actilon, CMP001, DV281, cobitolimod TLR9 and NOD2 agonist: MIS416

STINO signaling pathway activator: ADU-S100

STING agonist: MK-1454, SB 11285, IMSA101

RIG-I agonist: RGT 100

The oligonucleotides of the invention can be administered in/with a delivery carrier or in a form linked with a carrier. The carrier includes, but not limited to, sterol (e.g., cholesterol), cochleates, emulsomes. ISCOMs: a lipid (e.g., a cationic lipid, anionic lipid), liposomes; ethylene glycol (PEG); polyglycolide-co-lactide (PGLA); microspheres; polymers (e.g., carboxymethylcellulose (CMC), chitosan, mannitol, hydroxypropylmethylcellulose (HPMC)); live bacterial vectors (e.g., *Salmonella, Escherichia coli, bacillus* Calmette-Gurin, *Shigella, Lactobacillus*); live viral vectors (e.g., Vaccinia, Adenovirus, Herpes simplex), virosomes, virus-like particles.

The target subject to be administered with the oligonucleotide of the present invention is preferably human, but in one embodiment the subject can be non-human animals such as dog, cat, horse, pig, goat, sheep, cow, monkey, chicken, mouse, or rat.

"Therapeutically effective amount": In order to treat or prevent a target disease or disorder, a therapeutically effective amount of the oligonucleotides of the present invention is administered to a subject. The "therapeutically effective amount" of one or more than one of the oligonucleotides means a sufficient amount of the oligonucleotides used to achieve a desired result of treating or preventing a disorder in a subject. The oligonucleotides of the present invention may be employed in pure form or in pharmaceutically acceptable carriers. Alternatively, the ODN of the present invention may be administered as pharmaceutical compositions. The "amount" in the invention shall refer to a dose. The dose can be determined by standard techniques well known to those skilled in the art and can variously depend on the factors including, but not limited to the size or/and overall health of the subject or the severity of the disease symptom. Introduction of the oligonucleotide of the invention can be carried out as a single treatment or over a series of treatments. Subject doses of the oligonucleotide of the invention for the administration range from about 1 μg (micro gram) to 10 g per administration. Preferably, the doses range from 0.1 mg to 5 g. More preferably, the doses range from 0.3 mg to 3 g. The most preferably, the doses range from 1 mg to 1 g.

The therapeutically effective amount for human subject may be estimated based on the amount for suitable for non-human animals by using the human equivalent dose (HED) or human equivalent concentration (HEC). The therapeutically effective amount for human subject may be, but not limited to, 0.3-60 mg/day, preferably 1-30 mg/day, more preferably 2-8 mg/day.

"Route of administration": For clinical use, the oligonucleotide of the present invention can be administered alone or formulated in a pharmaceutical composition via any suitable route of administration that is effective to achieve the desired therapeutic result. The "route" of administering the oligonucleotide of the present invention shall mean the enteral, parenteral and topical administration or inhalation. The enteral routes of administration of the oligonucleotide of the present invention include oral, gastric, intestinal, and rectal. The parenteral route includes subcutaneous, intravenous, transdermal, intradermal, sublingual, intranasal, transmucosal, pulmonary, vaginal, aerosol, intraocular, intratracheal, intrarectal, intraspinal, intramuscular, intraarticular, intraperitoneal, intracardiac, intraosseus, intrathecal, intravitreal, inhalational or topical administration. The topical route of administration of the oligonucleotide of the invention denotes the application of the oligonucleotide externally to the epidermis, to the buccal cavity and into the ear, eye and nose. Intratumoral administration is one of the routes of administration, which is generally conducted by the injection of the test compound(s) in the tumors or in the peritumor region.

"Pharmaceutical composition": A pharmaceutical composition shall mean the composition comprising a therapeutically effective amount of the oligonucleotide of the present invention with or without a pharmaceutically acceptable carrier. The pharmaceutical compositions can comprise one or more oligonucleotides of the invention. The composition includes but not limited to aqueous or saline solutions, particles, aerosols, pellets, granules, powders, tablets, coated tablets, orally dissolving/disintegrating tablets, (micro) capsules, suppositories, syrups, emulsions, suspensions, creams, drops and other pharmaceutical compositions suitable for use in a variety of drug delivery systems. The compositions may be administered parenterally, orally, rectally, intravaginally, intraperitoneally, topically (in a dosage form as powders, ointments, gels, drops or transdermal patch), bucally, or as an oral or nasal spray. In all cases, the composition must be sterile and stable under the conditions of manufacture and storage and preserved against the microbial contamination. Pharmaceutical compositions of this invention for parenteral injection comprise pharmaceutically-acceptable sterile aqueous or nonaqueous solutions, dispersions, suspensions or emulsions, as well as sterile powders for reconstitution into sterile injectable solutions or dispersions just prior to use. The oligonucleotide of the invention can be suspended in an aqueous carrier, for example, in an isotonic buffer solution at a pH of about 3.0 to about 8.0, preferably at a pH of about 3,5 to about 7.4, 3.5 to 6.0, or 3.5 to about 5.0. The buffer solution includes sodium citrate-citric acid and sodium phosphate-phosphoric acid, and sodium acetate-acetic acid buffers. For oral administration, the composition will be formulated with edible carriers to form powders tablets, pills, orally dissolving/disintegrating tablets, dragees, capsules, liquids, gels, syrups, slurries, suspensions and the like. For a solid composition, conventional non-toxic solid carrier can include pharmaceutical grades of mannitol, lactose, starch, or magnesium stearate. For buccal administration, the composition will be tablet or lozenge in conventional manner. For inhalation, the composition will be an aerosol spray from pressurized pack, a nebulizer, or a dry powder and can be selected by one of skilled in the art. In some cases, in order to prolong the effect of the oligonucleotide of the invention, the oligonucleotide of the present invention are also suitably administered by sustained-release systems. The oligonucleotide of the present invention can be used in a liquid suspension of crystalline or amorphous material with poor water solubility to slow the releasing of the oligonucleotide. Alternatively, delayed releasing of a parenterally administered drug form of the oligonucleotide is accomplished by dissolving or suspending the oligonucleotide in hydrophobic material (such as an acceptable oil vehicle). Injectable depot form is made by entrapping the oligonucleotide in liposomes or microemulsions or other biodegradable semi-permeable polymer matrices such as polylactide-polyglycolide, polyorthoesters and polyanhydrides.

EXAMPLES

The invention will be described in more detail in the following Examples. Meanwhile, the invention is not limited to these Examples. In these Examples, herein, experiments using commercially available kits and reagents were done according to attached protocols, unless otherwise stated. The skilled artisan will appreciate that the oligonucleotides of the present invention can easily be applied to treat target diseases including cancers and infectious diseases. The present invention will now be demonstrated by the following non-limiting examples.

Materials and Methods

<Oligo-DeoxyNucleotides (ODNs)>

The single-strand oligodeoxynucleotides (ODNs) were synthesized at Hokkaido System Science Co., Ltd. by conventional phosphoramidite method in the form of baving no phosphate at 3' end and the purity and identity were confirmed at the manufacturer. The nucleosides with phosphorothioate (PS) internucleotide linkages at 3' ends are described in small letters, while the ones with phosphodiester (PO) intranucleotide linkages at 3' ends or the oligonucleosides are described in capital letters in the following examples. All synthesized ODNs were first dissolved with distilled pyrogen-free water and further dilutions were carried out using pyrogen-free reagents for the studies.

<10% FBS-RPMI-complete medium>

RPM11640 Medium is supplemented with 10% FBS, 2 mM L-Glutamine, 1% penicillin-streptomycin, 10 mM HEPES, 1 mM Sodium Pyruvate, and 50 mM 2-Mercaptoethanol. The medium was further filtered with 0.45 μm syringe filter.

<CAL-1 cells>

CAL-1 cells (a human plasmacytoid dendritic cell line; Maeda et al., Int J Hematol., 2005, 81, 148-54; JP5011520B) are cultured under humidified atmosphere and 5% $CO_2$ conditions at 37° C. with 10% FBS-RPMI-Complete Medium. CAL-1 cells become confluent for two days after subculturing to 1:5, but the cells are passaged before becoming confluent for the studies shown below. Suspension culture dish is used to culture CAL-1 cells.

<Detection of TLR9 Activation by GFP Induction Through NF-kB Activation>

The levels of transcriptional activity of NF-kB promoter, which is induced by TLR9 signaling pathway, were monitored as indication of levels of activity of TLR9 signaling. CAL-1/NF-kB-GFP cell line was established for monitoring the activity of NF-kB transcription factor in cell-based assays (WO2014082254A). For the establishment of the CAL-1/NF-kB-GFP cell line, the vector encoding GFP reporter gene driven by the NF-kB consensus transcriptional response element was transfected into CAL-1 cells by electroporation. Transfected cells were further selected with zeocin. Stable transfectants were produced by single-cell cloning of the selected transfectants. GFP expression induced by TLR9 agonist, CpG2395 (S'-tcgtcgtttteggcgegcgccG-3', SEQ ID NO:45), was confirmed. Briefly, CAL-1/NF-kB-GFP cells ($1 \times 10^5$/well) were plated in 96-wells flat-bottomed plate and cultured with or without CpG2395. The cells were incubated at 37° C. in a 5% $CO_2$ humidified incubator for 6 hours. GFP expression level in the cells was evaluated by flow cytometer (FACS Calibur, BD Bioscience Co., Ltd). The percentage of GFP positive cells was analyzed as an indication of the levels of TLR9 signaling activity. This established NF-kB-OFP/CAL-1 cells was used in each assay.

<Detection of TLR7 Activation>

Activity of TLR7 was measured as enzymatic activity of secreted embryonic alkaline phosphatase (SEAP) in HEK-Blue™ TLR7 cells (Invivogen). The cells were incubated with indicated oligonucleotides or TLR7 agonists, such as 1 μg (microgram)/ml of Gardiquimod (GQ) or 1 μg/ml of CL264, at 37° C. in a 5% $CO_2$ humidified incubator for 24 hours; the induced SEAP was measured by the levels of absorbance at 655 nm resulted from the cleavage of the substrates (HEK-Blue™ Detection, Invivogen).

<Detection of TLR8 Activation>

Activity of TLR8 was measured as enzymatic activity of secreted embryonic alkaline phosphatase (SEAP) in HEK-BlueIM TLR8 cells (Invivogen). The cells were incubated with indicated oligonucleotides or TLR7 agonists, such as 200 ng/ml of TL8-506 or 5 μg/ml of CL075, for 24 hours at 37° C. in a 5% $CO_2$ humidified incubator for 24 hours; the induced SEAP was measured by the levels of absorbance at 655 nm resulted from the cleavage of the substrates (HEK-Blue™ Detection, Invivogen).

<Detection of Cytokine Production>

The levels of cytokines were measured by ELISA with the following kits: human IFN-α (eBioscience), human IL-6, human TNF-α (Thermo Fisher Scientific), human IL-12p40 (BioLegend), mouse IFN-α (PBL), mouse IL-6, mouse TNF-α and mouse IL-12p40 (Thermo Fisher Scientific). Measurement was conducted according to the manufactures' protocols.

<Isolation of Human PBMCs>

Peripheral blood was recovered from healthy volunteers. Same volume of RPMI medium was added to the blood and mixed well. Human PBMCs were purified by centrifugation over Histopaque™. Briefly, Histopaque-1077 (SIGMA) was put into centrifugation tube and same volume of blood/RPMI mixture was placed onto the Histopaque™. The tube was centrifuged for 20 minutes at 1800 rpm (700×g). White layer in the middle was recovered with a pipet into another tube and 100% FBS-RPMI complete medium was added. The mixture solution was centrifuged for 10 minutes at 1800 rpm (700×g) and the supernatant was removed. The cell Example 1

The fully-phosphorothioated ODNs of the present invention have adjuvant activity.

The fully-phosphorothioated ODNs used in this study are listed in the following Table 4.

The small case letter denotes the nucleoside is phosphorothioate-modified in the internucleotide linkage at 3', and the capital case letter denotes that the nucleoside is un-modified (without phosphodiester linkage) at 3'.

TABLE 4

| ODN IDs | sequences | SEQ ID NOs |
|---|---|---|
| CpG2395 | 5'-tcgtcgttttcggcgcgcgccG-3' | SEQ ID NO: 45 |
| CpG685 | 5'-tcgtcgacgtcgttcgttctC-3' | SEQ ID NO: 46 |
| M362 | 5'-tcgtcgtcgttcgaacgacgttgaT-3' | SEQ ID NO: 47 |
| D60-1 | 5'-tcgaacgttcgaacgttcgaacgttcgaaT-3' | SEQ ID NO: 48 |
| A001 | 5'-tcgcaacgtttgcgacgtcggtcgA-3' | SEQ ID NO: 6 |
| A002 | 5'-tcgcaacgtttgcgacggcgctcgA-3' | SEQ ID NO: 7 |
| A003 | 5'-tcgcaacgtttgcgacgtcgttcgA-3' | SEQ ID NO: 8 |
| A004 | 5'-tcgcaacgtttgcgacggcgttcgA-3' | SEQ ID NO: 9 |
| A003#delA | 5'-tcgcaacgtttgcgacgtcgttcG-3' | SEQ ID NO: 10 |
| A003#endG | 5'-tcgcaacgtttgcgacgtcgttcgG-3' | SEQ ID NO: 11 |
| A011 | 5'-tcgcaacgtttacgacgtcggtcgA-3' | SEQ ID NO: 12 |
| A012 | 5'-tcgcaacgtttacgacggcgctcgA-3' | SEQ ID NO: 13 |
| A013 | 5'-tcgcaacgtttacgacgtcgttcgA-3' | SEQ ID NO: 14 |
| A014 | 5'-tcgcaacgtttacgacggcgttcgA-3' | SEQ ID NO: 15 | pellet was treated with 2 ml of distilled water to lyse erythrocytes, and then 20 ml of 10% FBS RPMI complete medium was immediately added to the tube. After washing twice with the medium, the cells were suspended in the medium and the cell number was counted. The freshly isolated PBMCs were used in each assay.

<Preparation of Mouse Splenocytes>

Spleen was recovered from mouse. The spleen was placed into the dish filled with RPMI medium. The spleen was crushed with nylon mesh by using the rubber tip of a syringe plunger (2.5 ml syringe). Spleen cells included in the medium were transferred to a 50 ml Falcon tube by filtrating through a 70 μm strainer. After centrifuged at 1500×g for 5 minutes, the cells were washed by 1×DPBS. The cells were treated with ACK lysis buffer to lyse erythrocytes. 1 ml of ACK Lysing Buffer was added to the cell pellet and pipetted 20 times with P1000 Pipette, and then the tube was left to stand on ice for 2 minutes. Twenty ml of RPMI complete medium with 10% FBS was immediately added to the tube. After washing twice with the medium, the cells were resuspended in the same medium and the cell number was counted. The splenocytes were then used for the further studies.

<Analysis of Immunostimulating Activity of ODNs>

The ODNs shown in the Table 4 were incubated with CAL-1/NF-kB-GFP cells for 6 hours at indicated concentration (0.1 μM or 0.3 μM). NF-kB activations by the ODNs were evaluated based on the percentage of GFP positive cells analyzed with flow cytometer (FACS Calibur, BD Bioscience Co., Ltd.). The data was analyzed with FlowJo™ ver 10 (FlowJo LLC).

As shown in FIG. 1A, GFP expression was induced in CAL-1/NF-kB-GFP cells by authentic TLR9 agonist; CpG2395 stimulation, indicating that activation of NF-kB was induced by TLR9 activation with CpG2395. The ODNs of this invention, fully phosphorothioated (PS) A001, A002, A003 and A004 were shown to have stronger TLR9 activation activity comparing to CpG2395. Further, as demonstrated in FIG. 1B, the ODNs of this invention exhibited stronger TLR9 activities than other known CpG ODNs, such as CpG685. M362 and D60-1, did. Considering that the levels of TLR9 activities induced by the ODNs do not depend on the nucleic acid lengths, the difference in the agonistic activities was considered to lie in the specific sequences.

As many previous reports argued that the importance of gtcgtt sequence in CpG ODNs for the optimal activation of human TLR9 (Hartmann, G. et al., J Immunol, 2000. 164(2): p. 944-53. Bauer, S., et al., Proc Natl Acad Sci USA, 2001. 98(16): p. 9237-42), CpG2395 and CpG685 (5'-tcgtcgacgicettegiteiC-3'; SEQ ID NO:46) has one gtcgtt sequence. In previous reports, it was claimed that the tcgt sequence at 5' end within CpG ODN is very important for the activation of human TLR9 (Pohar, J., et al., J Immunol, 2017. 198(5): p. 2093-2104; Ohto, U., et al., Immunity, 2018. 48(4): p. 649-658). The conventional CpG ODNs, CpG239S, CpG685 and M362 (S'-legtcgtcgttegaacgacgttgaT-3'; SEQ ID NO:47) have the tcgt sequence at the 5' end as the TLR9 activating motif, according to this rule.

Among the ODNs of this invention, only A003 has one gtcgtt sequence and others do not have the gtcgtt sequence, and all the ODNs of this invention do not have the tcgt sequence at 5' end. However, all ODNs of this invention exhibited stronger human TLR9 activation than conventional CpG ODNs, such as CpG2395, CpG685 and M362, did.

As described above, while 5'-tcgt and 'gtcgtt' motifs in authentic CpG ODNs are known as TLR9 activating motifs in human (Wang, X., et al., Vaccine, 2008. 26(15): p. 1893-901), those motifs in the ODNs of the present invention were shown to have negligible contribution to overall activity, suggesting that other optimal stretches/motifs for human TLR9 exist in the ODNs of this invention.

As shown in FIGS. 1C and 1D, the activities of A003 and A003 #endG were the same. While the activity of A003 #delA was slightly decreased by the conversion of the base at the 3' end, the activity was still much stronger than conventional CpG-ODN, CpG2395 (shown in FIG. 1A). This indicates that the nucleotide at 3' end is dispensable for the activity.

In addition, as shown in FIGS. 1E, 1F and 1G, each ODN set, A001 and A011; A002 and A012; A003 and A013; and

Example 2

The oligonucleotides of the present invention majorly activate TLR9.

<Human TLR7 and TLR8 Activation by the ODNs>

HEK blue™ TLR7 cells were stimulated with TLR agonists for 24 hours. As shown in FIG. 2A, TLR7 agonists Gardiquimod (GQ) and CL264 activated TLR7 and gave positive signals. In contrast, authentic TLR9 agonist CpG2395 and the ODNs of the present invention could not activate TLR7 signaling pathway.

In addition, HEK blue™ TLR8 cells were stimulated with TLR agonists for 24 hours. As shown in FIG. 2B, TLR8 agonists, TL8-506 and CL075, activated TLR8 and gave positive signals. In contrast, authentic TLR9 agonist CpG2395 and the ODNs of the present invention could not activate TLR8 signaling pathway.

Example 3

Characteristic nucleotide stretches with partial phosphorothioation of the oligonucleotides of the present invention The existence of minimum stretch of the oligonucleotides of this invention, which increases the TLR9 agonistic activity, was investigated.

<ODNs>

The single-strand ODNs with internucleotide linkages with partial phosphorothioation were prepared as listed in the Table 5.

TABLE 5

| ODN IDs | sequences | SEQ ID NOs |
|---------|-----------|------------|
| A003 | 5'-tcgcaacgtttgcgacgtcgttcgA-3' | SEQ ID NO: 8 |
| A103 | 5'-tCgcaacgtttgcgacgtcgttcgA-3' | SEQ ID NO: 16 |
| A203 | 5'-tCgcaaCgtttgcgacgtcgttcgA-3' | SEQ ID NO: 17 |
| A303 | 5'-tCgCaaCgtttgcgacgtcgttcgA-3' | SEQ ID NO: 18 |
| A403 | 5'-tCgCaacgtttgCgaCgtcgttcgA-3' | SEQ ID NO: 19 |
| A503 | 5'-tCgCaacgtttgCgaCgtcgttCgA-3' | SEQ ID NO: 20 |
| A603 | 5'-tCgCaaCgtttgcgacgtCgttCgA-3' | SEQ ID NO: 21 |
| A703 | 5'-tCgCaaCgtttgCgaCgtCgttCgA-3' | SEQ ID NO: 22 |
| DV093 | 5'-tCgtgcatcgatgcaacG-3' | SEQ ID NO: 49 |
| DV093C | 5'-tCgtgcatcgatgCaaCG-3' | SEQ ID NO: 50 |
| DV094 | 5'-aacaacaacgttgttgtT-3' | SEQ ID NO: 51 |
| DV094C | 5'-aaCaaCaaCgttgttgtT-3' | SEQ ID NO: 52 |

A004 and A014, exhibited similar levels of the activity to the another one in the same set, indicating that replacements of the indicated nucleotides in the ODNs do not give any significant changes in the activities of the ODNs.

Taken together, the mutations of bases at the position 12, 18, 21 and 25 from the 5' end within the ODNs may not cause the reduction of the stimulatory activities of the ODNs. The ODNs of the invention were shown to have 5'-tcgcaacgttt-n-cgaeg-n-cg-nn-cg-3' (SEQ ID NO:2) as the core structure with the TLR9 activating activity.

The small case letter denotes the nucleoside is phosphorothioate-modified in the internucleotide linkage at 3', and the capital case letter denotes that the nucleoside is with phosphodiester internucleotide linkage or un-modified (without phosphodiester linkage) at 3'.

<Analysis of the TLR9 Agonist Activity of the ODNs>

The agonist activities of the ODNs were analyzed by the GFP expressions in the CAL-1/NF-kB-GFP cells.

As shown in the FIG. 3A, fully PS A003 shows low activity at tested concentration during 6 hours stimulation.

As it has been reported that change of internucleotide linkage with phosphodiester (PO) bond in the CG motif of the authentic fully PS CpG ODNs increased activity for the activation of TLR9 (Pohar, J., et al., Sci Rep, 2017. 7(1): p. 14598, WO2004016805A), A103 and A203, which have CG motif with PO bond and retain the same sequence with A003, showed increased activity. However, additional PO bond at CA in the CAACG stretch of ODNs (A303) further up-regulate the activity as shown in FIGS. 3A and 3B. As it can be seen from the left panel of FIG. 3B (0.1 μM), A303 exhibited significantly stronger activity than A103 and A203 did. This suggests that importance of PO bonds within CAACG stretch (CaaCg) for the activity.

As shown in FIG. 3C, A403 and A503 exhibited reduced activity than A303 did, while both A403 and A503 have increased number of CG motifs with PO bond than A303 does. This indicates that numbers of CG motifs with PO bond in the ODNs of the present invention is not important for the activity, although the number of CG motifs with PO Interestingly, CaaCg stretch (CAACG motif with partial phosphorothioation) in DV093C and DV094C could not increase their activity comparing to the original DV093 or DV094. The change in internucleotide linkage changing the caacg stretch to CaaCg in DV093 and DV094 did not improve the activity as shown in the FIG. 3F. These data suggest that the existence of specific CaaCg stretch such as the one in the ODNs of the present invention, but not randomly located CaaCg ODNs, has unique property to increase TLR9 activity. Taken together, 5'-tCgCaaCg stretch (such as the one in A303 and A603) can be in the core structure of the ODNs of the present invention.

Example 4

Core Structures of the ODNs of the Present Invention
<ODNs>
The single-strand ODNs with internucleotide linkages with partial phosphorothioation were prepared as listed in the Table 6.

TABLE 6

| ODN IDs | sequences | SEQ ID NOs |
|---|---|---|
| A601 | 5'-tCgCaaCgtttgcgacgtCggtCgA-3' | SEQ ID NO: 23 |
| A602 | 5'-tCgCaaCgtttgcgacggCgctCgA-3' | SEQ ID NO: 24 |
| A603 | 5'-tCgCaaCgtttgcgacgtCgttCgA-3' | SEQ ID NO: 21 |
| A604 | 5'tCgCaaCgtttgcgacggCgttCgA-3' | SEQ ID NO: 26 |
| A605 | 5'-tCgCaaCgtttgcgacgcCgttCgA-3' | SEQ ID NO: 27 |
| A606 | 5'tCgCaaCgtttgcgacggCgtaCgA-3' | SEQ ID NO: 28 |
| A607 | 5'-tCgCaaCgtttgcgacggCgtgCgA-3' | SEQ ID NO: 29 |
| CpG2006 | 5'-tcgtcgttttgtcgttttgtcgtT-3' | SEQ ID NO: 53 | bond in authentic CpG ODNs is previously believed to be important for the activity (WO2004016805A). Importantly, both A403 and A503 do not have CaaCg stretch (2 PO bonds within CAACG motif). While A603 and A503 have same number of PO bond at CG motifs, A603 exhibited better activity than A503 did. A603 keeps CaaCg stretch like A303 and showed similar activity as A303, suggesting the importance of CaaCg stretch comparing to the increased numbers of CG motifs with PO bond for the optimal activity. A703 has PO bonds at all CG motifs, but exhibited smaller activity than A303 and A603 (stimulation at 0.1 μM) did, indicating that increase in numbers of CG motif with PO bond is dispensable for the maximized activity of the ODNs of the present invention. The total numbers of CG motifs with PO bond is negligible for the optimization of the activity, which is not expected from the previously known effect of Py (pyrimidine)-PO-Pu (purine) (WO2004016805A).

As shown in FIG. 3D, importance of CaaCg stretch was further confirmed by detection of inflammatory cytokine production induced by the ODNs. A303 and A603 induced similar levels of cytokines to each other and the production levels were higher than those of A403 and A503.

Importance of CaaCg stretch was examined in previously reported CpGs, DV093 and DV094 (FIG. 3E). While both DV093 and DV094 have caacg motif in their sequence, their activity was much smaller than A003.

The activities of the ODNs were analyzed by the GFP expressions in the CAL-1/NF-kB-GFP cells. As shown in the FIGS. 4A and 4B, all tested ODNs, which have varieties in bases at positions 18, 21 and 22 in 3' regions, exhibited similar levels of activities to each other and their activity was much higher than that of authentic CpG ODNs such as CpG2006. This indicates that the bases at positions 18, 21 and 22 in the 3' region of the ODNs are dispensable for the activity.

As described above, 'gtcgtt' motifs in authentic CpG ODNs are known as TLR9 activating motif for human (Wang, X., et al., Vaccine, 2008. 26(15): p. 1893-901) and CpG2006 has the three motifs in the sequence. In the meantime, A603 only has single motif among our tested ODNs and all tested ODNs including A603 exhibited similar levels of activity, indicating that other optimal motifs or stretches for human TLR9 activity exist in the ODNs of this invention. Further, our data indicates that the 'gtcgtt' motif in the ODNs of the present invention was shown to have negligible contribution to overall activity, as long as they keep Cg-nn-Cg stretch in their 3' regions. 3' end of the ODNs in this invention need the g-n-Cg-nn-Cg as a core structure.

As shown in FIG. 5A and 5B, the ODNs of the present invention as well as authentic TLR9 agonist CpG2395 could not activate both TLR7 and TLR8 signaling pathway, suggesting that the ODNs of the present invention were TLR9 agonists.

Example 5

Partially dephosphorothioated ODN of the present invention does not have TLR7 and TLR8 activity
<ODNs>
The single-strand ODNs with internucleotide linkages with partial phosphorothioation were prepared as listed in the Table 7.

TABLE 7

| ODN IDs | sequences | SEQ ID NOs |
|---|---|---|
| A601 | 5'tCgCaaCgtttgcgacgtCggtCgA-3' | SEQ ID NO: 23 |
| A601G | 5'-tCgCaaCgtttGcgacgtCggtCgA-3' | SEQ ID NO: 33 |
| A602 | 5'-tCgCaaCgtttgcgacggCgctCgA-3' | SEQ ID NO: 24 |
| A602G | 5'-tCgCaaCgtttGcgacggCgctCgA-3' | SEQ ID NO: 35 |
| A611 | 5'-tCgCaaCgtttacgacgtCggtCgA-3' | SEQ ID NO: 30 |
| A611A | 5'-tCgCaaCgtttAcgacgtCggtCgA-3' | SEQ ID NO: 34 |
| A612 | 5'-tCgCaaCgtttacgacggCgctCgA-3' | SEQ ID NO: 31 |
| A612A | 5'-tCgCaaCgtttAcgacggCgctCgA-3' | SEQ ID NO: 36 |

The activities of the ODNs were analyzed by the GFP expressions in the CAL~I/NF-KB-GFP cells. As shown in the FIGS. 6A, 6B and 6C, all tested ODNs, which have variation of the bases and/or the internucleotide linkages at 3' side at position 12, exhibited similar levels of activities on NF-kB activation. This indicates that the nucleotide at position 12 allow mutation and the inter-nucleotide linkage at the 3' of the nucleotide can either be PO or PS linkage.

As shown in FIGS. 7A and 7B, the ODNs as well as authentic TLR9 agonist CpG2395 could not activate both TLR7 and TLR8 signaling pathway, suggesting that the ODNs were TLR9 activator.

Taken together from Examples from 1 to 5, the ODNs of the invention were shown to have 5'-tcgcaacgtti-n-cgacg-n-cg-nn-cg-3' (SEQ ID NO:2) as core sequence. For the maximum human TLR9 stimulatory activity, the ODNs preferably have 5'-(CgCaaCgttt-n-cgacg-n-Cg-nn-Cg-3' (SEQ ID NO:5) as core structure.

Further, as the ODNs of present invention do not follow the previous reported rules, the ODNs of the present invention are distinct from reported authentic CpG ODNs and are novel type of TLR9 agonists.

Example 6

Evaluation of the Levels of TLR9 Stimulation in Human Cells
<Stimulation of HAL-01 Cells>
Human B-ALL cell line. HAL-01 cells, were purchased from DSMZ (Cat. ACC610). HAL-01 cells were maintained with 10% FBS-RPMI complete medium and stimulated with the ODNs for 24 hours at 1.0 μM. The cells were stained with APC conjugated anti-CD40 Ab (eBiosciences) and PE conjugated anti-CD86 Ab (BD Pharmingen). Induction of CD40 and CD86 expression was evaluated with flow cytometer.

<Stimulation of Human PBMCs>
Prepared human PBMCs ($5 \times 10^5$ cells/200 μl) were stimulated with the ODNs for 24 hours at 0.1 μM or 0.3 μM. The cell proliferation was evaluated with WST-1 assay (Roche) according to the manufactures' protocols. The culture supernatants were recovered and the cytokine productions were evaluated with ELISA according to the manufactures' protocols.

It is known that human B cells express TLR9 and thus TLR9 agonist can activate human B cells. It has been demonstrated that human B-ALL cell line was stimulated with TLR9 agonist and the surface expression of co-stimulatory molecules, such as CD40 and CD86, were up-regulated with the stimulation. As shown in FIG. &A, the ODNs of the present invention activated B-ALL cell line, HAL-01, cells, which was shown by the upregulated surface expression of CD40 and CD86.

It is demonstrated that ODNs of the present invention can induce the proliferation of human PBMCs and the inflammatory cytokine productions. As shown in FIGS. 8B and 8C, the ODNs of the present invention could stimulate human PBMCs, which induced the cell proliferations and inflammatory cytokine productions, such as IFN-α. IL-6 and IL-12.

Example 7

Evaluation of the Levels of TLR9 Stimulation in Mouse Cells
<Stimulation of Mouse Spleen Cells (Splenocytes)>
Prepared splenocytes were stimulated with the ODNs at 0.03 μM for 24 hours. The culture supernatants were recovered and the cytokine productions were evaluated with ELISA of the culture supernatants according to the manufactures' protocols. Prepared splenocytes were stimulated with the ODNs for 24 hours at various concentrations. The cell proliferation was evaluated with WST-1 assay (Roche) according to the manufactures' protocols.

It is known that TLR9 agonist can induce the inflammatory cytokine productions and the proliferation of mouse splenocytes. As shown in FIG. 9A, the ODNs of the present invention could induce mouse inflammatory cytokine productions, such as TNF-α and IL-12. Further, as shown in FIGS. 9B and 9C, the ODNs induced the proliferations of mouse splenocytes. The activities of the ODNs were clearly higher than that of authentic TLR9 agonists CpG2395 and CpG2006.

The tested ODNs A601, A602 and A603 have the structure 5'-tCgCaaCgttt-n-cgacg-n-Cg-an-Cg-3 (SEQ ID NO:5)

as core structure and these ODNs could activate mouse splenocytes as well as human PBMCs. This indicates that defined PO inter-linkage bond at precise position, such as 'tCgCaaCg' and 'Cg-nn-Cg' structures, would be important for optimal TLR9 activation in both mouse and human.

Example 8

In Vivo Anti-Tumor Efficacy of the ODNs
<CT26 Cells>
The BALB/c-derived mouse colon carcinoma cell line, CT26, was purchased from American Type Culture Collection (ATCC, CRL-2638). CT26 cells were cultured with 10% FBS-RPMI complete medium under humidified atmosphere and 5% CO2 conditions at 37° C.
<Inoculation of CT26 Cells into Mice>
CT26 cells were recovered with a 0.25% trypsin-EDTA solution in PBS. After suspending in medium, the cells were passed through a 40 μm strainer and counted with the number of cells. The concentration of the cells in the suspension was adjusted to $2\times10^6$ cells/ml. For inoculation into BALB/c mice, 100 μl of the cell suspension was used per mouse ($2\times10^5$ cells/mouse). After shaving the back of the mouse, 100 μl of CT26 cell suspension was injected subcutaneously into the right flanks of the mice with a 28 gauge needle. The mice were kept un-treated for two weeks until when the tumor volumes reached about 150 mm³. The tumor volume was measured every 2 or 3 days and the mice were divided into three groups based on the tumor volume. The tumor volume was calculated with the following formula:

$$\text{Tumor Volume (mm}^3) = 1/2 \text{ (Length} \times \text{Width}^2)$$

<Administration of the ODNs>
Administration of the ODNs (40 μg/50 μl/mouse) to peri-tumor was started on the grouping day (day 0) and repeated on day 2. Administration of the ODNs of the present invention was conducted twice in total during the study. The tumor volume and the body weight of each group mice were measured every two or three days. As shown in FIG. 10, administration of the ODNs of present invention clearly induced tumor regression in mice. On day 11, tumors in the almost all mice were rejected by the administration of the ODNs (FIGS. 10A and 10B). No weight loss was observed in each group of mice during the study (FIG. 10C). This indicates that the ODNs (A601 and A602) have anti-tumor activity and have little toxicity. In consideration of the fact that A601, A602 and A603 showed same activity in mouse splenocytes as shown in FIG. 9B, A603 will exhibit same strong anti-tumor activity as A601 and A602 did. The ODNs of present invention were proven to have anti-tumor activity.

Example 9

In Vivo Anti-Tumor Efficacy of the ODNs (2)
<Inoculation of CT26 Cells and Treatment with the ODNs>
CT26 cells were inoculated into right flanks of BALB/c mice as described above. The mice were kept un-treated for two weeks until when the tumor volumes reached about 100 mm³. The tumor volume was measured every 2 or 3 days and the mice were divided into three groups based on the tumor volume. Administration of the ODNs (A601 and A602) (40 μg/50 μl/mouse) into peri-tumor was started on the grouping day (day 0) and repeated on day 2. The administration of the ODNs of the present invention was conducted twice in total during the study. As a negative control, PBS was administered in the place of the solution containing ODNs. The tumor volume and the body weight of each group mice were measured every two or three days until tumor rejection was confirmed (day 14).

The tumor volume was calculated with the following formula:

$$\text{Tumor Volume(mm}^3) = 1/2 (\text{Length} \times \text{Width}^2)$$

<Re-Inoculation of CT26 Cells in the Treated Mice>
CT26 cells ($2\times10^5$) were re-inoculated to left flank of the mice on day 14, which had been inoculated with tumor and confirmed with tumor rejection, and the mice were further kept un-treated. The tumor volume of left flank in each mouse was measured every 2 or 3 days until 14 days after CT26 re-inoculation.

As shown in FIG. 11A, administration of the ODNs of present invention clearly induced tumor rejection in mice. Further, the mice treated with the ODNs rejected tumor as well (FIG. 11B). While tumor in left flank grew in mice without treatment with the ODNs of the present invention, all the mice treated with the ODNs rejected re-challenged tumor without any further treatment for 2 weeks (FIG. 11B). This suggests that the ODNs of present invention can induce and establish memory of anti-tumor immunity.

Example 10

In Vivo Efficacy of the ODNs Against Lung Metastasis
<CT26 Lung Metastasis Model>
The cell suspensions of CT26 cells were prepared as described above. The suspension was adjusted to a final concentration of $2.5\times10^6$ cells/ml. For the induction of lung metastasis of CT26 cells, 200 μl of the cell suspension was intravenously (I.V.) injected to BALB/c mice ($5\times10^5$ cells/mouse) from the tail vein using a 28 gauge needle (day 0). On day 2, administration of the ODNs was started (subcutaneous injection to the skin of the back, 40 μg/50 μl/mouse). Same dose of administration was repeated on day 5. As a negative control, PBS was administered in the place of the solution containing ODNs.

Measurement of body weight and observation of behavior of the mice were carried out three times a week after transplantation of CT26 cells. On day 18, the mice were sacrificed and the lung weights were measured. The metastatic tumor nodules in each lung from the mice were also counted.

As shown in FIG. 12, lung weights of the mice in PBS treated group were drastically increased and many tumor nodules were observed. In contrast, no such increase of lung weights was observed in the mice of the group treated with the ODNs of the present invention. Further, only a small number of tumor nodules were observed in the mice of the treated group. This indicates that the ODNs of present invention can suppress growth of the metastatic cancer cells in lung.

Example 11

In Vivo Efficacy of the ODNs Examined with Variation in Administration Routes
<CT26 Lung Metastasis Model>
The induction of lung metastasis with CT26 cells were performed as described above. On the next day of CT26 cells injection, administration of the ODN, A602 was started. In this study, two administration routes were tested. One is subcutaneous (S.C.) injection to the skin of the back (25 μg/50 μl/mouse) and another is intradermal (I.D.) injection into the root of the ear (25 µg/20 µl/mouse). Administration with the same dose was repeated on day 3 and day 5. After transplantation of CT26 cells, measurement of body weight and observation of behavior of the mice were carried out three times a week. On day 16, the mice were sacrificed and the metastatic tumor nodules in each lang from the mouse were counted.

<CT26 Liver Metastasis Model>

The cell suspensions of CT26 cells were prepared as described above. The cell suspension was adjusted to a final concentration of $1.0 \times 10^6$ cells/ml. For the induction of liver metastasis of CT26 cells, 100 µl of the cell suspension was injected to spleen ($1 \times 10^5$ cells/mouse) as described below (day 0). Briefly, mice were anesthetized and the skin was shaved. An abdominal incision (0.5 cm) was made adjacent to the spleen (a left flank incision was approximately 2 cm left of the abdominal midline). The prepared CT26 cell suspension was injected into the spleen using a 30 G needle, which was maintained in the spleen for five minutes following injection. To prevent bleeding, blood vessels leading to the spleen were tightly tied with surgical sutures and then splenectomized with a sharp scissor. The peritoneum and the skin were sutured and the mouse was warmed under light. Recovery of the mice from anesthesia was monitored and confirmed. On day 2, the mice were divided into three groups based on the body weight and administration of the ODN, A602, was started. In this study, two administration routes were tested. One is S.C. injection to the skin of the back (12.5 µg/50 µl/mouse) and another is I.D. injection into the root of the ear (12.5 µg/20 µl/mouse). Same dose of administration was repeated on day 5, day 8 and day 12. Measurement of body weight and observation of behavior of the mice were carried out three times a week after transplantation of CT26 cells. On day 20, the mice were sacrificed and the metastatic tumor nodules in each liver from the mouse were counted.

As shown in FIG. 13A, many tumor nodules were observed in PBS treated group. In contrast, only a small numbers of tumor nodules were observed in both of the groups treated by S.C. or I.D. route. Interestingly. I.D, administration into the root of the ear exhibited better efficacy than S.C. administration did. These results indicate that the ODNs of present invention can block the growth of metastatic cancer cells in lung and can achieve systemic efficacies.

As shown in FIG. 13B, severe liver metastasis was also observed in PBS treated group. In contrast, no tumor nodules were observed in both of the group treated by S.C. or I.D. route indicating that the ODNs of present invention can prevent growth of the metastatic cancer cells in liver and can achieve systemic efficacy.

Taken together, the ODNs of present invention can block and reject metastatic tumor growth systemically.

Example 12

Activation of Anti-Tumor Immunity of Human PBMCs

<Co-Culture of Human B-ALL Cells and Human PBMCs>

Prepared human PBMCs ($5 \times 10^5$ cells) were co-cultured with human B-ALL cell line, RCH-ACV ($5 \times 10^4$ cells) together with the ODNs (0.1 µM) in 200 µl of 10% FBS-RPMI-complete medium for 3 days and the co-cultured cells were recovered. The elimination of RCH-ACV by the human PBMCs was evaluated by the decrease in RCH-ACV cells distinguished by staining with APC conjugated anti-CD19 Ab and FITC conjugated anti-CD138 Ab. Human PBMCs alone and RCH-ACV alone were used as staining controls. Existence of CD19 and CD138 double positive cells (RCH-ACV) was analyzed with flowcytometer. Existence of RCH-ACV in no-stimulated PBMCs was set as 100% in FIG. 14B.

<Co-Culture of Human Colon Carcinoma Cells and Human PBMCs>

Prepared human PBMCs ($5 \times 10^5$ cells) were co-cultured with human colon carcinoma cell, COLO205 (ATCC, CCL-222) ($5 \times 10^4$ cells) together with the ODNs (0.1 µM) in 200 µl of 10% FBS-RPMI-complete medium for 3 days and the co-cultured cells were recovered. The elimination of COLO205 by the human PBMCs was evaluated by the decrease in COLO205 cells distinguished by staining with APC conjugated anti-CD24 Ab and FITC conjugated anti-CD45 Ab. Human PBMCs alone and COLO205 alone were used as staining controls. Existence of CD24 positive/CD45 negative cells (COLO205) was analyzed with flowcytometer. Existence of COLO205 in no-stimulated PBMCs was set as 100% in FIG. 15B.

As shown in FIG. 14A, RCH-ACV cells were CD19 and CD138 double positive, while no CD19 and CD138 double positive cells were observed in prepared human PBMCs alone. 8.6% of RCH-ACV cells were detected when human PBMCs and RCH-ACV were co-cultured in the no-stimulated condition. In the presence of A601, A602 and A603, only 0.2% to 0.3% of RCH-ACV were detected in the cultured cells, indicating that human PBMCs eliminated almost all of RCH-ACV cells in response to the ODNs of present invention. The efficacy of elimination of the hematologic cancer cells was further confirmed as shown in FIG. 14B.

As shown in FIG. 15A. COLO205 cells were CD24 positive and CD45 negative, while no such cells were observed in prepared human PBMCs alone. 19.2% of COLO205 cells were detected when human PBMCs and COLO20S were co-cultured in the no-stimulated condition (the culture without ODNs). In the presence of A601, A602 and A603, only 0.5% to 0.9% of COLO205 were detected in the cultured cells, indicating that human PBMCs eliminated almost all of COLO205 cells in response to the ODNs of present invention. The elimination efficacy was further confirmed as shown in FIG. 15B.

Taken together, it is suggested that activated human PBMCs with the ODNs of present invention can eliminate both hematological malignancies and solid tumors.

Example 13

Efficacy of the ODNs Other than A601, A602 and A603

Human PBMCs and mouse splenocytes were stimulated with the ODNs of present invention (0.15 µM) for 24 hours and the cell proliferations were evaluated with WST-1 assay.

Human PBMCs were co-cultured with cancer cells (RCH-ACV or COLO205) together with the ODNs of present invention (0.1 µM) for 3 days as were done in the Example 12. The elimination of the cancer cells by human PBMCs was examined. Existence of cancer cells in no-stimulated PBMC's set as 100% in FIG. 16B.

As previously shown in FIG. 6, all the ODNs, A601. A602, A601G, A611A, A602G and A612A, exhibited similar levels in the activity of TLR9 activation when examined in the CAL-1/NF-kB-GFP cells. To evaluate whether the ODNs show same traits in primary human PBMCs and mouse cells, the ODNs AKOIG, A611A, A602G and A612A were evaluated in several assay systems, which was previously tested with A601 and A602. As shown in FIG. 16A, all tested ODNs of present invention did induce cell proliferation in a similar magnitude in both human PBMCs and mouse splenocytes. Further, as shown in FIG. 16B, all tested ODNs of present invention induced significant elimination of cancer cells in the presence of human PBMCs. These results indicate that activated human PBMCs with the ODNs, A601G, A611A, A602G and A612A, can eliminate both hematological malignancies and solid tumors as A601 and A602 do.

Collectively, all the ODNs of present invention, which exhibited similar levels of activities with A601 or A602 does in the CAL-1/NF-kB-GFP cells, are suggested to induce the elimination of human cancer cells in human PBMCs as well as anti-tumor immune reactions in mice.

INDUSTRIAL APPLICABILITY

The present invention provides novel oligonucleotides and their derivative oligonucleotides. In addition, the present invention provides pharmaceutical composition comprising the oligonucleotide(s) selected from the said oligonucleotides. The present invention also provides method of treatment of the target diseases by the administration of oligonucleotide(s) selected from the said oligonucleotides.

---

The invention claimed is:

1. A single strand oligonucleotide comprising a nucleotide sequence motif 5'-tcgcaacgttt-n-cgacg-n-cg-nn-cg-3' (SEQ ID NO:2), wherein n denotes any base, and wherein the total base number of the single strand oligonucleotide is 24 or 25.

2. The oligonucleotide according to claim 1, wherein the oligonucleotide comprises a sequence motif selected from the group consisting of:

```
                                  (SEQ ID NO: 54)
  5'-tcgcaacgtttgcgacgtcggtcga;

(SEQ ID NO: 55)
  5'-tcgcaacgtttgcgacggcgctcga;

(SEQ ID NO: 56)
  5'-tcgcaacgtttgcgacgtcgttcga;

(SEQ ID NO: 57)
  5'-tcgcaacgtttgcgacggcgttcga;

(SEQ ID NO: 58)
  5'-tcgcaacgtttgcgacgtcgttcg;

(SEQ ID NO: 59)
  5'-tcgcaacgtttgcgacgtcgttcgg;

(SEQ ID NO: 60)
  5'-tcgcaacgtttacgacgtcggtcga;

(SEQ ID NO: 61)
  5'-tcgcaacgtttacgacggcgctcga;

(SEQ ID NO: 62)
  5'-tcgcaacgtttacgacgtcgttcga; and (SEQ ID NO: 63)
  5'-tcgcaacgtttacgacggcgttcga.
```

3. The oligonucleotide according to claim 1, wherein the internucleotide linkage(s) of the oligonucleotide is partially or fully chemically modified.

4. The oligonucleotide according to claim 3, wherein the chemically-modified internucleotide linkage is phosphoro-thioated.

5. The oligonucleotide according to claim 1, wherein the oligonucleotide comprises a partially phosphorothioated oligonucleotide stretch selected from the group consisting of:

```
                                  (SEQ ID NO: 16)
  5'-tCgcaacgtttgcgacgtcgttcgA-3';

(SEQ ID NO: 17)
  5'-tCgcaaCgtttgcgacgtcgttcgA-3';

(SEQ ID NO: 18)
  5'-tCgCaaCgtttgcgacgtcgttcgA-3';

(SEQ ID NO: 19)
  5'-tCgCaacgtttgCgaCgtcgttcgA-3';

(SEQ ID NO: 20)
  5'-tCgCaacgtttgCgaCgtcgttCgA-3';

(SEQ ID NO: 21)
  5'-tCgCaaCgtttgcgacgtCgttCgA-3';

(SEQ ID NO: 22)
  5'-tCgCaaCgtttgCgaCgtCgttCgA-3';

(SEQ ID NO: 23)
  5'-tCgCaaCgtttgcgacgtCggtCgA-3';

(SEQ ID NO: 24)
  5'-tCgCaaCgtttgcgacggCgctCgA-3';
```

-continued

```
                                  (SEQ ID NO: 26)
  5'-tCgCaaCgtttgcgacggCgttCgA-3';

(SEQ ID NO: 27)
  5'-tCgCaaCgtttgcgacgcCgttCgA-3';

(SEQ ID NO: 28)
  5'-tCgCaaCgtttgcgacggCgtaCgA-3';

(SEQ ID NO: 29)
  5'-tCgCaaCgtttgcgacggCgtgCgA-3';

(SEQ ID NO: 30)
  5'-tCgCaaCgtttacgacgtCggtCgA-3';

(SEQ ID NO: 31)
  5'-tCgCaaCgtttacgacggCgctCgA-3';

(SEQ ID NO: 32)
  5'-tCgCaaCgtttacgacgtCgttCgA-3';

(SEQ ID NO: 33)
  5'-tCgCaaCgtttGcgacgtCggtCgA-3';

(SEQ ID NO: 34)
  5'-tCgCaaCgtttAcgacgtCggtCgA-3';

(SEQ ID NO: 35)
  5'-tCgCaaCgtttGcgacggCgctCgA-3';

(SEQ ID NO: 36)
  5'-tCgCaaCgtttAcgacggCgctCgA-3';

(SEQ ID NO: 37)
  5'-tCgCaaCgtttGcgacgtCgttCgA-3';

(SEQ ID NO: 38)
  5'-tCgCaaCgtttAcgacgtCgttCgA-3';

(SEQ ID NO: 39)
  5'-tCgCaaCgtttGcgacgtCggtCgG-3';

(SEQ ID NO: 40)
  5'-tCgCaaCgtttAcgacgtCggtCgG-3';

(SEQ ID NO: 41)
  5'-tCgCaaCgtttGcgacggCgctCgG-3';

(SEQ ID NO: 42)
  5'-tCgCaaCgtttAcgacggCgctCgG-3';

(SEQ ID NO: 43)
  5'-tCgCaaCgtttGcgacgtCgttCgG-3'; and (SEQ ID NO: 44)
  5'-tCgCanCgittAcgacgtCgttCgG-3';
``` wherein the capital letter denotes a nucleoside with no modified internucleotide linkage at 3', and the small letter denotes a nucleoside with an internucleotide linkage with phosphorothioation at 3'.

6. The oligonucleotide according to claim 1, wherein the oligonucleotide comprises a partially phosphorothioated oligonucleotide stretch selected from the group consisting of:

```
                                  (SEQ ID NO: 33)
  5'-tCgCaaCgtttGcgacgtCggtCgA-3';

(SEQ ID NO: 34)
  5'-tCgCaaCgtttAcgacgtCggtCgA-3';

(SEQ ID NO: 35)
  5'-tCgCaaCgtttGcgacggCgctCgA-3'; and (SEQ ID NO: 36)
  5'-tCgCaaCgtttAcgacggCgctCgA-3',
``` wherein the capital letter denotes a nucleoside with no modified internucleotide linkage at 3', and the small letter denotes a nucleoside with an internucleotide linkage with phosphorothioation at 3'.

7. A pharmaceutical composition, comprising (i) a therapeutically effective amount of the oligonucleotide according to claim 1 or a double-strand oligonucleotide comprising the oligonucleotide according to claim 1, and (ii) a pharmaceutical acceptable carrier.

\* \* \* \* \*

SEQUENCE LISTING

```
<160> NUMBER OF SEQ ID NOS: 63

<210> SEQ ID NO 1
<211> LENGTH: 11
<212> TYPE: DNA
<213> ORGANISM: Artificial Sequence
<220> FEATURE:
<223> OTHER INFORMATION: synthetic construct

<400> SEQUENCE: 1
tcgcaacgtt t                                                         11

<210> SEQ ID NO 2
<211> LENGTH: 24
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (12)..(12)
<223> OTHER INFORMATION: n stands for any base
<220> FEATURE:
<221> NAME/KEY: misc_feature
<222> LOCATION: (18)..(18)
<223> OTHER INFORMATION: n stands for any base
<220> FEATURE:
<221> NAME/KEY: misc_feature
<222> LOCATION: (21)..(21)
<223> OTHER INFORMATION: n stands for any base
<220> FEATURE:
<221> NAME/KEY: misc_feature
<222> LOCATION: (22)..(22)
<223> OTHER INFORMATION: n stands for any base

<400> SEQUENCE: 2
tcgcaacgtt tncgacgncg nncg                                           24

<210> SEQ ID NO 3
<211> LENGTH: 24
<212> TYPE: DNA
<213> ORGANISM: Artificial Sequence
<220> FEATURE:
<223> OTHER INFORMATION: synthetic construct

<400> SEQUENCE: 3
tcgcaacgtt trcgacgkcg bdcg                                           24

<210> SEQ ID NO 4
<211> LENGTH: 25
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
```

```
<222> LOCATION: (22)..(22)
<223> OTHER INFORMATION: n stands for any base

<400> SEQUENCE: 4
tcgcaacgtt trcgacgkcg bncgr                                         25

<210> SEQ ID NO 5
<211> LENGTH: 24
<212> TYPE: DNA
<213> ORGANISM: Artificial Sequence
<220> FEATURE:
<223> OTHER INFORMATION: synthetic construct
<220> FEATURE:
<221> NAME/KEY: modified_base
<222> LOCATION: (1)..(1)
<223> OTHER INFORMATION: phosphorothioate-modified at 3' internucleotide
      bond
<220> FEATURE:
<221> NAME/KEY: modified_base
<222> LOCATION: (3)..(3)
<223> OTHER INFORMATION: phosphorothioate-modified at 3' internucleotide
      bond
<220> FEATURE:
<221> NAME/KEY: modified_base
<222> LOCATION: (5)..(6)
<223> OTHER INFORMATION: phosphorothioate-modified at 3' internucleotide
      bond
<220> FEATURE:
<221> NAME/KEY: modified_base
<222> LOCATION: (8)..(18)
<223> OTHER INFORMATION: phosphorothioate-modified at 3' internucleotide
      bond
<220> FEATURE:
<221> NAME/KEY: misc_feature
<222> LOCATION: (12)..(12)
<223> OTHER INFORMATION: n stands for any base
<220> FEATURE:
<221> NAME/KEY: misc_feature
<222> LOCATION: (18)..(18)
<223> OTHER INFORMATION: n stands for any base
<220> FEATURE:
<221> NAME/KEY: modified_base
<222> LOCATION: (20)..(22)
<223> OTHER INFORMATION: phosphorothioate-modified at 3' internucleotide
      bond
<220> FEATURE:
<221> NAME/KEY: misc_feature
<222> LOCATION: (21)..(21)
<223> OTHER INFORMATION: n stands for any base
<220> FEATURE:
<221> NAME/KEY: misc_feature
<222> LOCATION: (22)..(22)
<223> OTHER INFORMATION: n stands for any base

<400> SEQUENCE: 5
tcgcaacgtt tncgacgncg nncg                                          24

<210> SEQ ID NO 6
<211> LENGTH: 25
<212> TYPE: DNA
<213> ORGANISM: Artificial Sequence
<220> FEATURE:
<223> OTHER INFORMATION: synthetic construct
<220> FEATURE:
<221> NAME/KEY: modified_base
<222> LOCATION: (1)..(24)
<223> OTHER INFORMATION: phosphorothioate-modified at 3' internucleotide
      bond

<400> SEQUENCE: 6
tcgcaacgtt tgcgacgtcg gtcga                                         25

<210> SEQ ID NO 7
```

<211> LENGTH: 25
<212> TYPE: DNA
<213> ORGANISM: Artificial Sequence
<220> FEATURE:
<223> OTHER INFORMATION: synthetic construct
<220> FEATURE:
<221> NAME/KEY: modified_base
<222> LOCATION: (1)..(24)
<223> OTHER INFORMATION: phosphorothioate-modified at 3' internucleotide
      bond

<400> SEQUENCE: 7
tcgcaacgtt tgcgacggcg ctcga                                          25

<210> SEQ ID NO 8
<211> LENGTH: 25
<212> TYPE: DNA
<213> ORGANISM: Artificial Sequence
<220> FEATURE:
<223> OTHER INFORMATION: synthetic construct
<220> FEATURE:
<221> NAME/KEY: modified_base
<222> LOCATION: (1)..(24)
<223> OTHER INFORMATION: phosphorothioate-modified at 3' internucleotide
      bond

<400> SEQUENCE: 8
tcgcaacgtt tgcgacgtcg ttcga                                          25

<210> SEQ ID NO 9
<211> LENGTH: 25
<212> TYPE: DNA
<213> ORGANISM: Artificial Sequence
<220> FEATURE:
<223> OTHER INFORMATION: synthetic construct
<220> FEATURE:
<221> NAME/KEY: modified_base
<222> LOCATION: (1)..(24)
<223> OTHER INFORMATION: phosphorothioate-modified at 3' internucleotide
      bond

<400> SEQUENCE: 9
tcgcaacgtt tgcgacggcg ttcga                                          25

<210> SEQ ID NO 10
<211> LENGTH: 24
<212> TYPE: DNA
<213> ORGANISM: Artificial Sequence
<220> FEATURE:
<223> OTHER INFORMATION: synthetic construct
<220> FEATURE:
<221> NAME/KEY: modified_base
<222> LOCATION: (1)..(23)
<223> OTHER INFORMATION: phosphorothioate-modified at 3' internucleotide
      bond

<400> SEQUENCE: 10
tcgcaacgtt tgcgacgtcg ttcg                                           24

<210> SEQ ID NO 11
<211> LENGTH: 25
<212> TYPE: DNA
<213> ORGANISM: Artificial Sequence
<220> FEATURE:
<223> OTHER INFORMATION: synthetic construct
<220> FEATURE:
<221> NAME/KEY: modified_base
<222> LOCATION: (1)..(24)
<223> OTHER INFORMATION: phosphorothioate-modified at 3' internucleotide
      bond

```
<400> SEQUENCE: 11
tcgcaacgtt tgcgacgtcg ttcgg                                     25

<210> SEQ ID NO 12
<211> LENGTH: 25
<212> TYPE: DNA
<213> ORGANISM: Artificial Sequence
<220> FEATURE:
<223> OTHER INFORMATION: synthetic construct
<220> FEATURE:
<221> NAME/KEY: modified_base
<222> LOCATION: (1)..(24)
<223> OTHER INFORMATION: phosphorothioate-modified at 3' internucleotide
      bond

<400> SEQUENCE: 12
tcgcaacgtt tacgacgtcg gtcga                                     25

<210> SEQ ID NO 13
<211> LENGTH: 25
<212> TYPE: DNA
<213> ORGANISM: Artificial Sequence
<220> FEATURE:
<223> OTHER INFORMATION: synthetic construct
<220> FEATURE:
<221> NAME/KEY: modified_base
<222> LOCATION: (1)..(24)
<223> OTHER INFORMATION: phosphorothioate-modified at 3' internucleotide
      bond

<400> SEQUENCE: 13
tcgcaacgtt tacgacggcg ctcga                                     25

<210> SEQ ID NO 14
<211> LENGTH: 25
<212> TYPE: DNA
<213> ORGANISM: Artificial Sequence
<220> FEATURE:
<223> OTHER INFORMATION: synthetic construct
<220> FEATURE:
<221> NAME/KEY: modified_base
<222> LOCATION: (1)..(24)
<223> OTHER INFORMATION: phosphorothioate-modified at 3' internucleotide
      bond

<400> SEQUENCE: 14
tcgcaacgtt tacgacgtcg ttcga                                     25

<210> SEQ ID NO 15
<211> LENGTH: 25
<212> TYPE: DNA
<213> ORGANISM: Artificial Sequence
<220> FEATURE:
<223> OTHER INFORMATION: synthetic construct
<220> FEATURE:
<221> NAME/KEY: modified_base
<222> LOCATION: (1)..(24)
<223> OTHER INFORMATION: phosphorothioate-modified at 3' internucleotide
      bond

<400> SEQUENCE: 15
tcgcaacgtt tacgacggcg ttcga                                     25

<210> SEQ ID NO 16
<211> LENGTH: 25
<212> TYPE: DNA
<213> ORGANISM: Artificial Sequence
<220> FEATURE:
<223> OTHER INFORMATION: synthetic construct
```

-continued

```
<220> FEATURE:
<221> NAME/KEY: modified_base
<222> LOCATION: (1)..(1)
<223> OTHER INFORMATION: phosphorothioate-modified at 3' internucleotide
      bond
<220> FEATURE:
<221> NAME/KEY: modified_base
<222> LOCATION: (3)..(24)
<223> OTHER INFORMATION: phosphorothioate-modified at 3' internucleotide
      bond

<400> SEQUENCE: 16
tcgcaacgtt tgcgacgtcg ttcga                                              25

<210> SEQ ID NO 17
<211> LENGTH: 25
<212> TYPE: DNA
<213> ORGANISM: Artificial Sequence
<220> FEATURE:
<223> OTHER INFORMATION: synthetic construct
<220> FEATURE:
<221> NAME/KEY: modified_base
<222> LOCATION: (1)..(1)
<223> OTHER INFORMATION: phosphorothioate-modified at 3' internucleotide
      bond
<220> FEATURE:
<221> NAME/KEY: modified_base
<222> LOCATION: (3)..(6)
<223> OTHER INFORMATION: phosphorothioate-modified at 3' internucleotide
      bond
<220> FEATURE:
<221> NAME/KEY: modified_base
<222> LOCATION: (8)..(24)
<223> OTHER INFORMATION: phosphorothioate-modified at 3' internucleotide
      bond

<400> SEQUENCE: 17
tcgcaacgtt tgcgacgtcg ttcga                                              25

<210> SEQ ID NO 18
<211> LENGTH: 25
<212> TYPE: DNA
<213> ORGANISM: Artificial Sequence
<220> FEATURE:
<223> OTHER INFORMATION: synthetic construct
<220> FEATURE:
<221> NAME/KEY: modified_base
<222> LOCATION: (1)..(1)
<223> OTHER INFORMATION: phosphorothioate-modified at 3' internucleotide
      bond
<220> FEATURE:
<221> NAME/KEY: modified_base
<222> LOCATION: (3)..(3)
<223> OTHER INFORMATION: phosphorothioate-modified at 3' internucleotide
      bond
<220> FEATURE:
<221> NAME/KEY: modified_base
<222> LOCATION: (5)..(6)
<223> OTHER INFORMATION: phosphorothioate-modified at 3' internucleotide
      bond
<220> FEATURE:
<221> NAME/KEY: modified_base
<222> LOCATION: (8)..(24)
<223> OTHER INFORMATION: phosphorothioate-modified at 3' internucleotide
      bond

<400> SEQUENCE: 18
tcgcaacgtt tgcgacgtcg ttcga                                              25

<210> SEQ ID NO 19
<211> LENGTH: 25
<212> TYPE: DNA
<213> ORGANISM: Artificial Sequence
```

```
<220> FEATURE:
<223> OTHER INFORMATION: synthetic construct
<220> FEATURE:
<221> NAME/KEY: modified_base
<222> LOCATION: (1)..(1)
<223> OTHER INFORMATION: phosphorothioate-modified at 3' internucleotide
      bond
<220> FEATURE:
<221> NAME/KEY: modified_base
<222> LOCATION: (3)..(3)
<223> OTHER INFORMATION: phosphorothioate-modified at 3' internucleotide
      bond
<220> FEATURE:
<221> NAME/KEY: modified_base
<222> LOCATION: (5)..(12)
<223> OTHER INFORMATION: phosphorothioate-modified at 3' internucleotide
      bond
<220> FEATURE:
<221> NAME/KEY: modified_base
<222> LOCATION: (14)..(15)
<223> OTHER INFORMATION: phosphorothioate-modified at 3' internucleotide
      bond
<220> FEATURE:
<221> NAME/KEY: modified_base
<222> LOCATION: (17)..(24)
<223> OTHER INFORMATION: phosphorothioate-modified at 3' internucleotide
      bond

<400> SEQUENCE: 19
tcgcaacgtt tgcgacgtcg ttcga                                             25

<210> SEQ ID NO 20
<211> LENGTH: 25
<212> TYPE: DNA
<213> ORGANISM: Artificial Sequence
<220> FEATURE:
<223> OTHER INFORMATION: synthetic construct
<220> FEATURE:
<221> NAME/KEY: modified_base
<222> LOCATION: (1)..(1)
<223> OTHER INFORMATION: phosphorothioate-modified at 3' internucleotide
      bond
<220> FEATURE:
<221> NAME/KEY: modified_base
<222> LOCATION: (3)..(3)
<223> OTHER INFORMATION: phosphorothioate-modified at 3' internucleotide
      bond
<220> FEATURE:
<221> NAME/KEY: modified_base
<222> LOCATION: (5)..(12)
<223> OTHER INFORMATION: phosphorothioate-modified at 3' internucleotide
      bond
<220> FEATURE:
<221> NAME/KEY: modified_base
<222> LOCATION: (14)..(15)
<223> OTHER INFORMATION: phosphorothioate-modified at 3' internucleotide
      bond
<220> FEATURE:
<221> NAME/KEY: modified_base
<222> LOCATION: (17)..(22)
<223> OTHER INFORMATION: phosphorothioate-modified at 3' internucleotide
      bond
<220> FEATURE:
<221> NAME/KEY: modified_base
<222> LOCATION: (24)..(24)
<223> OTHER INFORMATION: phosphorothioate-modified at 3' internucleotide
      bond

<400> SEQUENCE: 20
tcgcaacgtt tgcgacgtcg ttcga                                             25

<210> SEQ ID NO 21
<211> LENGTH: 25
<212> TYPE: DNA
<213> ORGANISM: Artificial Sequence
```

-continued

```
<220> FEATURE:
<223> OTHER INFORMATION: synthetic construct
<220> FEATURE:
<221> NAME/KEY: modified_base
<222> LOCATION: (1)..(1)
<223> OTHER INFORMATION: phosphorothioate-modified at 3' internucleotide
      bond
<220> FEATURE:
<221> NAME/KEY: modified_base
<222> LOCATION: (3)..(3)
<223> OTHER INFORMATION: phosphorothioate-modified at 3' internucleotide
      bond
<220> FEATURE:
<221> NAME/KEY: modified_base
<222> LOCATION: (5)..(6)
<223> OTHER INFORMATION: phosphorothioate-modified at 3' internucleotide
      bond
<220> FEATURE:
<221> NAME/KEY: modified_base
<222> LOCATION: (8)..(18)
<223> OTHER INFORMATION: phosphorothioate-modified at 3' internucleotide
      bond
<220> FEATURE:
<221> NAME/KEY: modified_base
<222> LOCATION: (20)..(22)
<223> OTHER INFORMATION: phosphorothioate-modified at 3' internucleotide
      bond
<220> FEATURE:
<221> NAME/KEY: modified_base
<222> LOCATION: (24)..(24)
<223> OTHER INFORMATION: phosphorothioate-modified at 3' internucleotide
      bond

<400> SEQUENCE: 21
tcgcaacgtt tgcgacgtcg ttcga                                              25

<210> SEQ ID NO 22
<211> LENGTH: 25
<212> TYPE: DNA
<213> ORGANISM: Artificial Sequence
<220> FEATURE:
<223> OTHER INFORMATION: synthetic construct
<220> FEATURE:
<221> NAME/KEY: modified_base
<222> LOCATION: (1)..(1)
<223> OTHER INFORMATION: phosphorothioate-modified at 3' internucleotide
      bond
<220> FEATURE:
<221> NAME/KEY: modified_base
<222> LOCATION: (3)..(3)
<223> OTHER INFORMATION: phosphorothioate-modified at 3' internucleotide
      bond
<220> FEATURE:
<221> NAME/KEY: modified_base
<222> LOCATION: (5)..(6)
<223> OTHER INFORMATION: phosphorothioate-modified at 3' internucleotide
      bond
<220> FEATURE:
<221> NAME/KEY: modified_base
<222> LOCATION: (8)..(12)
<223> OTHER INFORMATION: phosphorothioate-modified at 3' internucleotide
      bond
<220> FEATURE:
<221> NAME/KEY: modified_base
<222> LOCATION: (14)..(15)
<223> OTHER INFORMATION: phosphorothioate-modified at 3' internucleotide
      bond
<220> FEATURE:
<221> NAME/KEY: modified_base
<222> LOCATION: (17)..(18)
<223> OTHER INFORMATION: phosphorothioate-modified at 3' internucleotide
      bond
<220> FEATURE:
<221> NAME/KEY: modified_base
<222> LOCATION: (20)..(22)
<223> OTHER INFORMATION: phosphorothioate-modified at 3' internucleotide
      bond
```

-continued

```
<220> FEATURE:
<221> NAME/KEY: modified_base
<222> LOCATION: (24)..(24)
<223> OTHER INFORMATION: phosphorothioate-modified at 3' internucleotide
      bond

<400> SEQUENCE: 22
tcgcaacgtt tgcgacgtcg ttcga                                          25

<210> SEQ ID NO 23
<211> LENGTH: 25
<212> TYPE: DNA
<213> ORGANISM: Artificial Sequence
<220> FEATURE:
<223> OTHER INFORMATION: synthetic construct
<220> FEATURE:
<221> NAME/KEY: modified_base
<222> LOCATION: (1)..(1)
<223> OTHER INFORMATION: phosphorothioate-modified at 3' internucleotide
      bond
<220> FEATURE:
<221> NAME/KEY: modified_base
<222> LOCATION: (3)..(3)
<223> OTHER INFORMATION: phosphorothioate-modified at 3' internucleotide
      bond
<220> FEATURE:
<221> NAME/KEY: modified_base
<222> LOCATION: (5)..(6)
<223> OTHER INFORMATION: phosphorothioate-modified at 3' internucleotide
      bond
<220> FEATURE:
<221> NAME/KEY: modified_base
<222> LOCATION: (8)..(18)
<223> OTHER INFORMATION: phosphorothioate-modified at 3' internucleotide
      bond
<220> FEATURE:
<221> NAME/KEY: modified_base
<222> LOCATION: (20)..(22)
<223> OTHER INFORMATION: phosphorothioate-modified at 3' internucleotide
      bond
<220> FEATURE:
<221> NAME/KEY: modified_base
<222> LOCATION: (24)..(24)
<223> OTHER INFORMATION: phosphorothioate-modified at 3' internucleotide
      bond

<400> SEQUENCE: 23
tcgcaacgtt tgcgacgtcg gtcga                                          25

<210> SEQ ID NO 24
<211> LENGTH: 25
<212> TYPE: DNA
<213> ORGANISM: Artificial Sequence
<220> FEATURE:
<223> OTHER INFORMATION: synthetic construct
<220> FEATURE:
<221> NAME/KEY: modified_base
<222> LOCATION: (1)..(1)
<223> OTHER INFORMATION: phosphorothioate-modified at 3' internucleotide
      bond
<220> FEATURE:
<221> NAME/KEY: modified_base
<222> LOCATION: (3)..(3)
<223> OTHER INFORMATION: phosphorothioate-modified at 3' internucleotide
      bond
<220> FEATURE:
<221> NAME/KEY: modified_base
<222> LOCATION: (5)..(6)
<223> OTHER INFORMATION: phosphorothioate-modified at 3' internucleotide
      bond
<220> FEATURE:
<221> NAME/KEY: modified_base
<222> LOCATION: (8)..(18)
<223> OTHER INFORMATION: phosphorothioate-modified at 3' internucleotide
      bond
```

```
<220> FEATURE:
<221> NAME/KEY: modified_base
<222> LOCATION: (20)..(22)
<223> OTHER INFORMATION: phosphorothioate-modified at 3' internucleotide
      bond
<220> FEATURE:
<221> NAME/KEY: modified_base
<222> LOCATION: (24)..(24)
<223> OTHER INFORMATION: phosphorothioate-modified at 3' internucleotide
      bond

<400> SEQUENCE: 24
tcgcaacgtt tgcgacggcg ctcga                                          25

<210> SEQ ID NO 25

<400> SEQUENCE: 25

000

<210> SEQ ID NO 26
<211> LENGTH: 25
<212> TYPE: DNA
<213> ORGANISM: Artificial Sequence
<220> FEATURE:
<223> OTHER INFORMATION: synthetic construct
<220> FEATURE:
<221> NAME/KEY: modified_base
<222> LOCATION: (1)..(1)
<223> OTHER INFORMATION: phosphorothioate-modified at 3' internucleotide
      bond
<220> FEATURE:
<221> NAME/KEY: modified_base
<222> LOCATION: (3)..(3)
<223> OTHER INFORMATION: phosphorothioate-modified at 3' internucleotide
      bond
<220> FEATURE:
<221> NAME/KEY: modified_base
<222> LOCATION: (5)..(6)
<223> OTHER INFORMATION: phosphorothioate-modified at 3' internucleotide
      bond
<220> FEATURE:
<221> NAME/KEY: modified_base
<222> LOCATION: (8)..(18)
<223> OTHER INFORMATION: phosphorothioate-modified at 3' internucleotide
      bond
<220> FEATURE:
<221> NAME/KEY: modified_base
<222> LOCATION: (20)..(22)
<223> OTHER INFORMATION: phosphorothioate-modified at 3' internucleotide
      bond
<220> FEATURE:
<221> NAME/KEY: modified_base
<222> LOCATION: (24)..(24)
<223> OTHER INFORMATION: phosphorothioate-modified at 3' internucleotide
      bond

<400> SEQUENCE: 26
tcgcaacgtt tgcgacggcg ttcga                                          25

<210> SEQ ID NO 27
<211> LENGTH: 25
<212> TYPE: DNA
<213> ORGANISM: Artificial Sequence
<220> FEATURE:
<223> OTHER INFORMATION: synthetic construct
<220> FEATURE:
<221> NAME/KEY: modified_base
<222> LOCATION: (1)..(1)
<223> OTHER INFORMATION: phosphorothioate-modified at 3' internucleotide
      bond
<220> FEATURE:
<221> NAME/KEY: modified_base
<222> LOCATION: (3)..(3)
```

<223> OTHER INFORMATION: phosphorothioate-modified at 3' internucleotide
      bond
<220> FEATURE:
<221> NAME/KEY: modified_base
<222> LOCATION: (5)..(6)
<223> OTHER INFORMATION: phosphorothioate-modified at 3' internucleotide
      bond
<220> FEATURE:
<221> NAME/KEY: modified_base
<222> LOCATION: (8)..(18)
<223> OTHER INFORMATION: phosphorothioate-modified at 3' internucleotide
      bond
<220> FEATURE:
<221> NAME/KEY: modified_base
<222> LOCATION: (20)..(22)
<223> OTHER INFORMATION: phosphorothioate-modified at 3' internucleotide
      bond
<220> FEATURE:
<221> NAME/KEY: modified_base
<222> LOCATION: (24)..(24)
<223> OTHER INFORMATION: phosphorothioate-modified at 3' internucleotide
      bond

<400> SEQUENCE: 27
tcgcaacgtt tgcgacgccg ttcga                                           25

<210> SEQ ID NO 28
<211> LENGTH: 25
<212> TYPE: DNA
<213> ORGANISM: Artificial Sequence
<220> FEATURE:
<223> OTHER INFORMATION: synthetic construct
<220> FEATURE:
<221> NAME/KEY: modified_base
<222> LOCATION: (1)..(1)
<223> OTHER INFORMATION: phosphorothioate-modified at 3' internucleotide
      bond
<220> FEATURE:
<221> NAME/KEY: modified_base
<222> LOCATION: (3)..(3)
<223> OTHER INFORMATION: phosphorothioate-modified at 3' internucleotide
      bond
<220> FEATURE:
<221> NAME/KEY: modified_base
<222> LOCATION: (5)..(6)
<223> OTHER INFORMATION: phosphorothioate-modified at 3' internucleotide
      bond
<220> FEATURE:
<221> NAME/KEY: modified_base
<222> LOCATION: (8)..(18)
<223> OTHER INFORMATION: phosphorothioate-modified at 3' internucleotide
      bond
<220> FEATURE:
<221> NAME/KEY: modified_base
<222> LOCATION: (20)..(22)
<223> OTHER INFORMATION: phosphorothioate-modified at 3' internucleotide
      bond
<220> FEATURE:
<221> NAME/KEY: modified_base
<222> LOCATION: (24)..(24)
<223> OTHER INFORMATION: phosphorothioate-modified at 3' internucleotide
      bond

<400> SEQUENCE: 28
tcgcaacgtt tgcgacggcg tacga                                           25

<210> SEQ ID NO 29
<211> LENGTH: 25
<212> TYPE: DNA
<213> ORGANISM: Artificial Sequence
<220> FEATURE:
<223> OTHER INFORMATION: synthetic construct
<220> FEATURE:
<221> NAME/KEY: modified_base
<222> LOCATION: (1)..(1)

-continued

```
<223> OTHER INFORMATION: phosphorothioate-modified at 3' internucleotide
      bond
<220> FEATURE:
<221> NAME/KEY: modified_base
<222> LOCATION: (3)..(3)
<223> OTHER INFORMATION: phosphorothioate-modified at 3' internucleotide
      bond
<220> FEATURE:
<221> NAME/KEY: modified_base
<222> LOCATION: (5)..(6)
<223> OTHER INFORMATION: phosphorothioate-modified at 3' internucleotide
      bond
<220> FEATURE:
<221> NAME/KEY: modified_base
<222> LOCATION: (8)..(18)
<223> OTHER INFORMATION: phosphorothioate-modified at 3' internucleotide
      bond
<220> FEATURE:
<221> NAME/KEY: modified_base
<222> LOCATION: (20)..(22)
<223> OTHER INFORMATION: phosphorothioate-modified at 3' internucleotide
      bond
<220> FEATURE:
<221> NAME/KEY: modified_base
<222> LOCATION: (24)..(24)
<223> OTHER INFORMATION: phosphorothioate-modified at 3' internucleotide
      bond

<400> SEQUENCE: 29
tcgcaacgtt tgcgacggcg tgcga                                           25

<210> SEQ ID NO 30
<211> LENGTH: 25
<212> TYPE: DNA
<213> ORGANISM: Artificial Sequence
<220> FEATURE:
<223> OTHER INFORMATION: synthetic construct
<220> FEATURE:
<221> NAME/KEY: modified_base
<222> LOCATION: (1)..(1)
<223> OTHER INFORMATION: phosphorothioate-modified at 3' internucleotide
      bond
<220> FEATURE:
<221> NAME/KEY: modified_base
<222> LOCATION: (3)..(3)
<223> OTHER INFORMATION: phosphorothioate-modified at 3' internucleotide
      bond
<220> FEATURE:
<221> NAME/KEY: modified_base
<222> LOCATION: (5)..(6)
<223> OTHER INFORMATION: phosphorothioate-modified at 3' internucleotide
      bond
<220> FEATURE:
<221> NAME/KEY: modified_base
<222> LOCATION: (8)..(18)
<223> OTHER INFORMATION: phosphorothioate-modified at 3' internucleotide
      bond
<220> FEATURE:
<221> NAME/KEY: modified_base
<222> LOCATION: (20)..(22)
<223> OTHER INFORMATION: phosphorothioate-modified at 3' internucleotide
      bond
<220> FEATURE:
<221> NAME/KEY: modified_base
<222> LOCATION: (24)..(24)
<223> OTHER INFORMATION: phosphorothioate-modified at 3' internucleotide
      bond

<400> SEQUENCE: 30
tcgcaacgtt tacgacgtcg gtcga                                           25

<210> SEQ ID NO 31
<211> LENGTH: 25
<212> TYPE: DNA
<213> ORGANISM: Artificial Sequence
```

```
<220> FEATURE:
<223> OTHER INFORMATION: synthetic construct
<220> FEATURE:
<221> NAME/KEY: modified_base
<222> LOCATION: (1)..(1)
<223> OTHER INFORMATION: phosphorothioate-modified at 3' internucleotide
      bond
<220> FEATURE:
<221> NAME/KEY: modified_base
<222> LOCATION: (3)..(3)
<223> OTHER INFORMATION: phosphorothioate-modified at 3' internucleotide
      bond
<220> FEATURE:
<221> NAME/KEY: modified_base
<222> LOCATION: (5)..(6)
<223> OTHER INFORMATION: phosphorothioate-modified at 3' internucleotide
      bond
<220> FEATURE:
<221> NAME/KEY: modified_base
<222> LOCATION: (8)..(18)
<223> OTHER INFORMATION: phosphorothioate-modified at 3' internucleotide
      bond
<220> FEATURE:
<221> NAME/KEY: modified_base
<222> LOCATION: (20)..(22)
<223> OTHER INFORMATION: phosphorothioate-modified at 3' internucleotide
      bond
<220> FEATURE:
<221> NAME/KEY: modified_base
<222> LOCATION: (24)..(24)
<223> OTHER INFORMATION: phosphorothioate-modified at 3' internucleotide
      bond

<400> SEQUENCE: 31
tcgcaacgtt tacgacggcg ctcga                                            25

<210> SEQ ID NO 32
<211> LENGTH: 25
<212> TYPE: DNA
<213> ORGANISM: Artificial Sequence
<220> FEATURE:
<223> OTHER INFORMATION: synthetic construct
<220> FEATURE:
<221> NAME/KEY: modified_base
<222> LOCATION: (1)..(1)
<223> OTHER INFORMATION: phosphorothioate-modified at 3' internucleotide
      bond
<220> FEATURE:
<221> NAME/KEY: modified_base
<222> LOCATION: (3)..(3)
<223> OTHER INFORMATION: phosphorothioate-modified at 3' internucleotide
      bond
<220> FEATURE:
<221> NAME/KEY: modified_base
<222> LOCATION: (5)..(6)
<223> OTHER INFORMATION: phosphorothioate-modified at 3' internucleotide
      bond
<220> FEATURE:
<221> NAME/KEY: modified_base
<222> LOCATION: (8)..(18)
<223> OTHER INFORMATION: phosphorothioate-modified at 3' internucleotide
      bond
<220> FEATURE:
<221> NAME/KEY: modified_base
<222> LOCATION: (20)..(22)
<223> OTHER INFORMATION: phosphorothioate-modified at 3' internucleotide
      bond
<220> FEATURE:
<221> NAME/KEY: modified_base
<222> LOCATION: (24)..(24)
<223> OTHER INFORMATION: phosphorothioate-modified at 3' internucleotide
      bond

<400> SEQUENCE: 32
tcgcaacgtt tacgacgtcg ttcga                                            25
```

```
<210> SEQ ID NO 33
<211> LENGTH: 25
<212> TYPE: DNA
<213> ORGANISM: Artificial Sequence
<220> FEATURE:
<223> OTHER INFORMATION: synthetic construct
<220> FEATURE:
<221> NAME/KEY: modified_base
<222> LOCATION: (1)..(1)
<223> OTHER INFORMATION: phosphorothioate-modified at 3' internucleotide
      bond
<220> FEATURE:
<221> NAME/KEY: modified_base
<222> LOCATION: (3)..(3)
<223> OTHER INFORMATION: phosphorothioate-modified at 3' internucleotide
      bond
<220> FEATURE:
<221> NAME/KEY: modified_base
<222> LOCATION: (5)..(6)
<223> OTHER INFORMATION: phosphorothioate-modified at 3' internucleotide
      bond
<220> FEATURE:
<221> NAME/KEY: modified_base
<222> LOCATION: (8)..(11)
<223> OTHER INFORMATION: phosphorothioate-modified at 3' internucleotide
      bond
<220> FEATURE:
<221> NAME/KEY: modified_base
<222> LOCATION: (13)..(18)
<223> OTHER INFORMATION: phosphorothioate-modified at 3' internucleotide
      bond
<220> FEATURE:
<221> NAME/KEY: modified_base
<222> LOCATION: (20)..(22)
<223> OTHER INFORMATION: phosphorothioate-modified at 3' internucleotide
      bond
<220> FEATURE:
<221> NAME/KEY: modified_base
<222> LOCATION: (24)..(24)
<223> OTHER INFORMATION: phosphorothioate-modified at 3' internucleotide
      bond

<400> SEQUENCE: 33
tcgcaacgtt tgcgacgtcg gtcga                                           25

<210> SEQ ID NO 34
<211> LENGTH: 25
<212> TYPE: DNA
<213> ORGANISM: Artificial Sequence
<220> FEATURE:
<223> OTHER INFORMATION: synthetic construct
<220> FEATURE:
<221> NAME/KEY: modified_base
<222> LOCATION: (1)..(1)
<223> OTHER INFORMATION: phosphorothioate-modified at 3' internucleotide
      bond
<220> FEATURE:
<221> NAME/KEY: modified_base
<222> LOCATION: (3)..(3)
<223> OTHER INFORMATION: phosphorothioate-modified at 3' internucleotide
      bond
<220> FEATURE:
<221> NAME/KEY: modified_base
<222> LOCATION: (5)..(6)
<223> OTHER INFORMATION: phosphorothioate-modified at 3' internucleotide
      bond
<220> FEATURE:
<221> NAME/KEY: modified_base
<222> LOCATION: (8)..(11)
<223> OTHER INFORMATION: phosphorothioate-modified at 3' internucleotide
      bond
<220> FEATURE:
<221> NAME/KEY: modified_base
<222> LOCATION: (13)..(18)
<223> OTHER INFORMATION: phosphorothioate-modified at 3' internucleotide
      bond
```

```
<220> FEATURE:
<221> NAME/KEY: modified_base
<222> LOCATION: (20)..(22)
<223> OTHER INFORMATION: phosphorothioate-modified at 3' internucleotide
      bond
<220> FEATURE:
<221> NAME/KEY: modified_base
<222> LOCATION: (24)..(24)
<223> OTHER INFORMATION: phosphorothioate-modified at 3' internucleotide
      bond

<400> SEQUENCE: 34
tcgcaacgtt tacgacgtcg gtcga                                             25

<210> SEQ ID NO 35
<211> LENGTH: 25
<212> TYPE: DNA
<213> ORGANISM: Artificial Sequence
<220> FEATURE:
<223> OTHER INFORMATION: synthetic construct
<220> FEATURE:
<221> NAME/KEY: modified_base
<222> LOCATION: (1)..(1)
<223> OTHER INFORMATION: phosphorothioate-modified at 3' internucleotide
      bond
<220> FEATURE:
<221> NAME/KEY: modified_base
<222> LOCATION: (3)..(3)
<223> OTHER INFORMATION: phosphorothioate-modified at 3' internucleotide
      bond
<220> FEATURE:
<221> NAME/KEY: modified_base
<222> LOCATION: (5)..(6)
<223> OTHER INFORMATION: phosphorothioate-modified at 3' internucleotide
      bond
<220> FEATURE:
<221> NAME/KEY: modified_base
<222> LOCATION: (8)..(11)
<223> OTHER INFORMATION: phosphorothioate-modified at 3' internucleotide
      bond
<220> FEATURE:
<221> NAME/KEY: modified_base
<222> LOCATION: (13)..(18)
<223> OTHER INFORMATION: phosphorothioate-modified at 3' internucleotide
      bond
<220> FEATURE:
<221> NAME/KEY: modified_base
<222> LOCATION: (20)..(22)
<223> OTHER INFORMATION: phosphorothioate-modified at 3' internucleotide
      bond
<220> FEATURE:
<221> NAME/KEY: modified_base
<222> LOCATION: (24)..(24)
<223> OTHER INFORMATION: phosphorothioate-modified at 3' internucleotide
      bond

<400> SEQUENCE: 35
tcgcaacgtt tgcgacggcg ctcga                                             25

<210> SEQ ID NO 36
<211> LENGTH: 25
<212> TYPE: DNA
<213> ORGANISM: Artificial Sequence
<220> FEATURE:
<223> OTHER INFORMATION: synthetic construct
<220> FEATURE:
<221> NAME/KEY: modified_base
<222> LOCATION: (1)..(1)
<223> OTHER INFORMATION: phosphorothioate-modified at 3' internucleotide
      bond
<220> FEATURE:
<221> NAME/KEY: modified_base
<222> LOCATION: (3)..(3)
<223> OTHER INFORMATION: phosphorothioate-modified at 3' internucleotide
      bond
```

```
<220> FEATURE:
<221> NAME/KEY: modified_base
<222> LOCATION: (5)..(6)
<223> OTHER INFORMATION: phosphorothioate-modified at 3' internucleotide
      bond
<220> FEATURE:
<221> NAME/KEY: modified_base
<222> LOCATION: (8)..(11)
<223> OTHER INFORMATION: phosphorothioate-modified at 3' internucleotide
      bond
<220> FEATURE:
<221> NAME/KEY: modified_base
<222> LOCATION: (13)..(18)
<223> OTHER INFORMATION: phosphorothioate-modified at 3' internucleotide
      bond
<220> FEATURE:
<221> NAME/KEY: modified_base
<222> LOCATION: (20)..(22)
<223> OTHER INFORMATION: phosphorothioate-modified at 3' internucleotide
      bond
<220> FEATURE:
<221> NAME/KEY: modified_base
<222> LOCATION: (24)..(24)
<223> OTHER INFORMATION: phosphorothioate-modified at 3' internucleotide
      bond

<400> SEQUENCE: 36
tcgcaacgtt tacgacggcg ctcga                                              25

<210> SEQ ID NO 37
<211> LENGTH: 25
<212> TYPE: DNA
<213> ORGANISM: Artificial Sequence
<220> FEATURE:
<223> OTHER INFORMATION: synthetic construct
<220> FEATURE:
<221> NAME/KEY: modified_base
<222> LOCATION: (1)..(1)
<223> OTHER INFORMATION: phosphorothioate-modified at 3' internucleotide
      bond
<220> FEATURE:
<221> NAME/KEY: modified_base
<222> LOCATION: (3)..(3)
<223> OTHER INFORMATION: phosphorothioate-modified at 3' internucleotide
      bond
<220> FEATURE:
<221> NAME/KEY: modified_base
<222> LOCATION: (5)..(6)
<223> OTHER INFORMATION: phosphorothioate-modified at 3' internucleotide
      bond
<220> FEATURE:
<221> NAME/KEY: modified_base
<222> LOCATION: (8)..(11)
<223> OTHER INFORMATION: phosphorothioate-modified at 3' internucleotide
      bond
<220> FEATURE:
<221> NAME/KEY: modified_base
<222> LOCATION: (13)..(18)
<223> OTHER INFORMATION: phosphorothioate-modified at 3' internucleotide
      bond
<220> FEATURE:
<221> NAME/KEY: modified_base
<222> LOCATION: (20)..(22)
<223> OTHER INFORMATION: phosphorothioate-modified at 3' internucleotide
      bond
<220> FEATURE:
<221> NAME/KEY: modified_base
<222> LOCATION: (24)..(24)
<223> OTHER INFORMATION: phosphorothioate-modified at 3' internucleotide
      bond

<400> SEQUENCE: 37
tcgcaacgtt tgcgacgtcg ttcga                                              25

<210> SEQ ID NO 38
```

-continued

```
<211> LENGTH: 25
<212> TYPE: DNA
<213> ORGANISM: Artificial Sequence
<220> FEATURE:
<223> OTHER INFORMATION: synthetic construct
<220> FEATURE:
<221> NAME/KEY: modified_base
<222> LOCATION: (1)..(1)
<223> OTHER INFORMATION: phosphorothioate-modified at 3' internucleotide
      bond
<220> FEATURE:
<221> NAME/KEY: modified_base
<222> LOCATION: (3)..(3)
<223> OTHER INFORMATION: phosphorothioate-modified at 3' internucleotide
      bond
<220> FEATURE:
<221> NAME/KEY: modified_base
<222> LOCATION: (5)..(6)
<223> OTHER INFORMATION: phosphorothioate-modified at 3' internucleotide
      bond
<220> FEATURE:
<221> NAME/KEY: modified_base
<222> LOCATION: (8)..(11)
<223> OTHER INFORMATION: phosphorothioate-modified at 3' internucleotide
      bond
<220> FEATURE:
<221> NAME/KEY: modified_base
<222> LOCATION: (13)..(18)
<223> OTHER INFORMATION: phosphorothioate-modified at 3' internucleotide
      bond
<220> FEATURE:
<221> NAME/KEY: modified_base
<222> LOCATION: (20)..(22)
<223> OTHER INFORMATION: phosphorothioate-modified at 3' internucleotide
      bond
<220> FEATURE:
<221> NAME/KEY: modified_base
<222> LOCATION: (24)..(24)
<223> OTHER INFORMATION: phosphorothioate-modified at 3' internucleotide
      bond

<400> SEQUENCE: 38
tcgcaacgtt tacgacgtcg ttcga                                          25

<210> SEQ ID NO 39
<211> LENGTH: 25
<212> TYPE: DNA
<213> ORGANISM: Artificial Sequence
<220> FEATURE:
<223> OTHER INFORMATION: synthetic construct
<220> FEATURE:
<221> NAME/KEY: modified_base
<222> LOCATION: (1)..(1)
<223> OTHER INFORMATION: phosphorothioate-modified at 3' internucleotide
      bond
<220> FEATURE:
<221> NAME/KEY: modified_base
<222> LOCATION: (3)..(3)
<223> OTHER INFORMATION: phosphorothioate-modified at 3' internucleotide
      bond
<220> FEATURE:
<221> NAME/KEY: modified_base
<222> LOCATION: (5)..(6)
<223> OTHER INFORMATION: phosphorothioate-modified at 3' internucleotide
      bond
<220> FEATURE:
<221> NAME/KEY: modified_base
<222> LOCATION: (8)..(11)
<223> OTHER INFORMATION: phosphorothioate-modified at 3' internucleotide
      bond
<220> FEATURE:
<221> NAME/KEY: modified_base
<222> LOCATION: (13)..(18)
<223> OTHER INFORMATION: phosphorothioate-modified at 3' internucleotide
      bond
<220> FEATURE:
<221> NAME/KEY: modified_base
```

```
<222> LOCATION: (20)..(22)
<223> OTHER INFORMATION: phosphorothioate-modified at 3' internucleotide
      bond
<220> FEATURE:
<221> NAME/KEY: modified_base
<222> LOCATION: (24)..(24)
<223> OTHER INFORMATION: phosphorothioate-modified at 3' internucleotide
      bond

<400> SEQUENCE: 39
tcgcaacgtt tgcgacgtcg gtcgg                                              25

<210> SEQ ID NO 40
<211> LENGTH: 25
<212> TYPE: DNA
<213> ORGANISM: Artificial Sequence
<220> FEATURE:
<223> OTHER INFORMATION: synthetic construct
<220> FEATURE:
<221> NAME/KEY: modified_base
<222> LOCATION: (1)..(1)
<223> OTHER INFORMATION: phosphorothioate-modified at 3' internucleotide
      bond
<220> FEATURE:
<221> NAME/KEY: modified_base
<222> LOCATION: (3)..(3)
<223> OTHER INFORMATION: phosphorothioate-modified at 3' internucleotide
      bond
<220> FEATURE:
<221> NAME/KEY: modified_base
<222> LOCATION: (5)..(6)
<223> OTHER INFORMATION: phosphorothioate-modified at 3' internucleotide
      bond
<220> FEATURE:
<221> NAME/KEY: modified_base
<222> LOCATION: (8)..(11)
<223> OTHER INFORMATION: phosphorothioate-modified at 3' internucleotide
      bond
<220> FEATURE:
<221> NAME/KEY: modified_base
<222> LOCATION: (13)..(18)
<223> OTHER INFORMATION: phosphorothioate-modified at 3' internucleotide
      bond
<220> FEATURE:
<221> NAME/KEY: modified_base
<222> LOCATION: (20)..(22)
<223> OTHER INFORMATION: phosphorothioate-modified at 3' internucleotide
      bond
<220> FEATURE:
<221> NAME/KEY: modified_base
<222> LOCATION: (24)..(24)
<223> OTHER INFORMATION: phosphorothioate-modified at 3' internucleotide
      bond

<400> SEQUENCE: 40
tcgcaacgtt tacgacgtcg gtcgg                                              25

<210> SEQ ID NO 41
<211> LENGTH: 25
<212> TYPE: DNA
<213> ORGANISM: Artificial Sequence
<220> FEATURE:
<223> OTHER INFORMATION: synthetic construct
<220> FEATURE:
<221> NAME/KEY: modified_base
<222> LOCATION: (1)..(1)
<223> OTHER INFORMATION: phosphorothioate-modified at 3' internucleotide
      bond
<220> FEATURE:
<221> NAME/KEY: modified_base
<222> LOCATION: (3)..(3)
<223> OTHER INFORMATION: phosphorothioate-modified at 3' internucleotide
      bond
<220> FEATURE:
<221> NAME/KEY: modified_base
```

```
<222> LOCATION: (5)..(6)
<223> OTHER INFORMATION: phosphorothioate-modified at 3' internucleotide
      bond
<220> FEATURE:
<221> NAME/KEY: modified_base
<222> LOCATION: (8)..(11)
<223> OTHER INFORMATION: phosphorothioate-modified at 3' internucleotide
      bond
<220> FEATURE:
<221> NAME/KEY: modified_base
<222> LOCATION: (13)..(18)
<223> OTHER INFORMATION: phosphorothioate-modified at 3' internucleotide
      bond
<220> FEATURE:
<221> NAME/KEY: modified_base
<222> LOCATION: (20)..(22)
<223> OTHER INFORMATION: phosphorothioate-modified at 3' internucleotide
      bond
<220> FEATURE:
<221> NAME/KEY: modified_base
<222> LOCATION: (24)..(24)
<223> OTHER INFORMATION: phosphorothioate-modified at 3' internucleotide
      bond

<400> SEQUENCE: 41
tcgcaacgtt tgcgacggcg ctcgg                                                       25

<210> SEQ ID NO 42
<211> LENGTH: 25
<212> TYPE: DNA
<213> ORGANISM: Artificial Sequence
<220> FEATURE:
<223> OTHER INFORMATION: synthetic construct
<220> FEATURE:
<221> NAME/KEY: modified_base
<222> LOCATION: (1)..(1)
<223> OTHER INFORMATION: phosphorothioate-modified at 3' internucleotide
      bond
<220> FEATURE:
<221> NAME/KEY: modified_base
<222> LOCATION: (3)..(3)
<223> OTHER INFORMATION: phosphorothioate-modified at 3' internucleotide
      bond
<220> FEATURE:
<221> NAME/KEY: modified_base
<222> LOCATION: (5)..(6)
<223> OTHER INFORMATION: phosphorothioate-modified at 3' internucleotide
      bond
<220> FEATURE:
<221> NAME/KEY: modified_base
<222> LOCATION: (8)..(11)
<223> OTHER INFORMATION: phosphorothioate-modified at 3' internucleotide
      bond
<220> FEATURE:
<221> NAME/KEY: modified_base
<222> LOCATION: (13)..(18)
<223> OTHER INFORMATION: phosphorothioate-modified at 3' internucleotide
      bond
<220> FEATURE:
<221> NAME/KEY: modified_base
<222> LOCATION: (20)..(22)
<223> OTHER INFORMATION: phosphorothioate-modified at 3' internucleotide
      bond
<220> FEATURE:
<221> NAME/KEY: modified_base
<222> LOCATION: (24)..(24)
<223> OTHER INFORMATION: phosphorothioate-modified at 3' internucleotide
      bond

<400> SEQUENCE: 42
tcgcaacgtt tacgacggcg ctcgg                                                       25

<210> SEQ ID NO 43
<211> LENGTH: 25
<212> TYPE: DNA
```

```
<213> ORGANISM: Artificial Sequence
<220> FEATURE:
<223> OTHER INFORMATION: synthetic construct
<220> FEATURE:
<221> NAME/KEY: modified_base
<222> LOCATION: (1)..(1)
<223> OTHER INFORMATION: phosphorothioate-modified at 3' internucleotide
      bond
<220> FEATURE:
<221> NAME/KEY: modified_base
<222> LOCATION: (3)..(3)
<223> OTHER INFORMATION: phosphorothioate-modified at 3' internucleotide
      bond
<220> FEATURE:
<221> NAME/KEY: modified_base
<222> LOCATION: (5)..(6)
<223> OTHER INFORMATION: phosphorothioate-modified at 3' internucleotide
      bond
<220> FEATURE:
<221> NAME/KEY: modified_base
<222> LOCATION: (8)..(11)
<223> OTHER INFORMATION: phosphorothioate-modified at 3' internucleotide
      bond
<220> FEATURE:
<221> NAME/KEY: modified_base
<222> LOCATION: (13)..(18)
<223> OTHER INFORMATION: phosphorothioate-modified at 3' internucleotide
      bond
<220> FEATURE:
<221> NAME/KEY: modified_base
<222> LOCATION: (20)..(22)
<223> OTHER INFORMATION: phosphorothioate-modified at 3' internucleotide
      bond
<220> FEATURE:
<221> NAME/KEY: modified_base
<222> LOCATION: (24)..(24)
<223> OTHER INFORMATION: phosphorothioate-modified at 3' internucleotide
      bond

<400> SEQUENCE: 43
tcgcaacgtt tgcgacgtcg ttcgg                                              25

<210> SEQ ID NO 44
<211> LENGTH: 25
<212> TYPE: DNA
<213> ORGANISM: Artificial Sequence
<220> FEATURE:
<223> OTHER INFORMATION: synthetic construct
<220> FEATURE:
<221> NAME/KEY: modified_base
<222> LOCATION: (1)..(1)
<223> OTHER INFORMATION: phosphorothioate-modified at 3' internucleotide
      bond
<220> FEATURE:
<221> NAME/KEY: modified_base
<222> LOCATION: (3)..(3)
<223> OTHER INFORMATION: phosphorothioate-modified at 3' internucleotide
      bond
<220> FEATURE:
<221> NAME/KEY: modified_base
<222> LOCATION: (5)..(6)
<223> OTHER INFORMATION: phosphorothioate-modified at 3' internucleotide
      bond
<220> FEATURE:
<221> NAME/KEY: modified_base
<222> LOCATION: (8)..(11)
<223> OTHER INFORMATION: phosphorothioate-modified at 3' internucleotide
      bond
<220> FEATURE:
<221> NAME/KEY: modified_base
<222> LOCATION: (13)..(18)
<223> OTHER INFORMATION: phosphorothioate-modified at 3' internucleotide
      bond
<220> FEATURE:
<221> NAME/KEY: modified_base
<222> LOCATION: (20)..(22)
<223> OTHER INFORMATION: phosphorothioate-modified at 3' internucleotide
``` bond
<220> FEATURE:
<221> NAME/KEY: modified_base
<222> LOCATION: (24)..(24)
<223> OTHER INFORMATION: phosphorothioate-modified at 3' internucleotide
     bond

<400> SEQUENCE: 44
tcgcaacgtt tacgacgtcg ttcgg                                            25

<210> SEQ ID NO 45
<211> LENGTH: 22
<212> TYPE: DNA
<213> ORGANISM: Artificial Sequence
<220> FEATURE:
<223> OTHER INFORMATION: synthetic construct
<220> FEATURE:
<221> NAME/KEY: modified_base
<222> LOCATION: (1)..(21)
<223> OTHER INFORMATION: phosphorothioate-modified at 3' internucleotide
     bond

<400> SEQUENCE: 45
tcgtcgtttt cggcgcgcgc cg                                               22

<210> SEQ ID NO 46
<211> LENGTH: 21
<212> TYPE: DNA
<213> ORGANISM: Artificial Sequence
<220> FEATURE:
<223> OTHER INFORMATION: synthetic construct
<220> FEATURE:
<221> NAME/KEY: modified_base
<222> LOCATION: (1)..(20)
<223> OTHER INFORMATION: phosphorothioate-modified at 3' internucleotide
     bond

<400> SEQUENCE: 46
tcgtcgacgt cgttcgttct c                                                21

<210> SEQ ID NO 47
<211> LENGTH: 25
<212> TYPE: DNA
<213> ORGANISM: Artificial Sequence
<220> FEATURE:
<223> OTHER INFORMATION: synthetic construct
<220> FEATURE:
<221> NAME/KEY: modified_base
<222> LOCATION: (1)..(24)
<223> OTHER INFORMATION: phosphorothioate-modified at 3' internucleotide
     bond

<400> SEQUENCE: 47
tcgtcgtcgt tcgaacgacg ttgat                                           25

<210> SEQ ID NO 48
<211> LENGTH: 30
<212> TYPE: DNA
<213> ORGANISM: Artificial Sequence
<220> FEATURE:
<223> OTHER INFORMATION: synthetic construct
<220> FEATURE:
<221> NAME/KEY: modified_base
<222> LOCATION: (1)..(29)
<223> OTHER INFORMATION: phosphorothioate-modified at 3' internucleotide
     bond

<400> SEQUENCE: 48
tcgaacgttc gaacgttcga acgttcgaat                                      30

```
<210> SEQ ID NO 49
<211> LENGTH: 18
<212> TYPE: DNA
<213> ORGANISM: Artificial Sequence
<220> FEATURE:
<223> OTHER INFORMATION: synthetic construct
<220> FEATURE:
<221> NAME/KEY: modified_base
<222> LOCATION: (1)..(1)
<223> OTHER INFORMATION: phosphorothioate-modified at 3' internucleotide
      bond
<220> FEATURE:
<221> NAME/KEY: modified_base
<222> LOCATION: (3)..(17)
<223> OTHER INFORMATION: phosphorothioate-modified at 3' internucleotide
      bond

<400> SEQUENCE: 49
tcgtgcatcg atgcaacg                                                      18

<210> SEQ ID NO 50
<211> LENGTH: 18
<212> TYPE: DNA
<213> ORGANISM: Artificial Sequence
<220> FEATURE:
<223> OTHER INFORMATION: synthetic construct
<220> FEATURE:
<221> NAME/KEY: modified_base
<222> LOCATION: (1)..(1)
<223> OTHER INFORMATION: phosphorothioate-modified at 3' internucleotide
      bond
<220> FEATURE:
<221> NAME/KEY: modified_base
<222> LOCATION: (3)..(13)
<223> OTHER INFORMATION: phosphorothioate-modified at 3' internucleotide
      bond
<220> FEATURE:
<221> NAME/KEY: modified_base
<222> LOCATION: (15)..(16)
<223> OTHER INFORMATION: phosphorothioate-modified at 3' internucleotide
      bond

<400> SEQUENCE: 50
tcgtgcatcg atgcaacg                                                      18

<210> SEQ ID NO 51
<211> LENGTH: 18
<212> TYPE: DNA
<213> ORGANISM: Artificial Sequence
<220> FEATURE:
<223> OTHER INFORMATION: synthetic construct
<220> FEATURE:
<221> NAME/KEY: modified_base
<222> LOCATION: (1)..(17)
<223> OTHER INFORMATION: phosphorothioate-modified at 3' internucleotide
      bond

<400> SEQUENCE: 51
aacaacaacg ttgttgtt                                                      18

<210> SEQ ID NO 52
<211> LENGTH: 18
<212> TYPE: DNA
<213> ORGANISM: Artificial Sequence
<220> FEATURE:
<223> OTHER INFORMATION: synthetic construct
<220> FEATURE:
<221> NAME/KEY: modified_base
<222> LOCATION: (1)..(2)
<223> OTHER INFORMATION: phosphorothioate-modified at 3' internucleotide
      bond
<220> FEATURE:
```

-continued

```
<221> NAME/KEY: modified_base
<222> LOCATION: (4)..(5)
<223> OTHER INFORMATION: phosphorothioate-modified at 3' internucleotide
      bond
<220> FEATURE:
<221> NAME/KEY: modified_base
<222> LOCATION: (7)..(8)
<223> OTHER INFORMATION: phosphorothioate-modified at 3' internucleotide
      bond
<220> FEATURE:
<221> NAME/KEY: modified_base
<222> LOCATION: (10)..(17)
<223> OTHER INFORMATION: phosphorothioate-modified at 3' internucleotide
      bond

<400> SEQUENCE: 52
aacaacaacg ttgttgtt                                                    18

<210> SEQ ID NO 53
<211> LENGTH: 24
<212> TYPE: DNA
<213> ORGANISM: Artificial Sequence
<220> FEATURE:
<223> OTHER INFORMATION: synthetic construct
<220> FEATURE:
<221> NAME/KEY: modified_base
<222> LOCATION: (1)..(23)
<223> OTHER INFORMATION: phosphorothioate-modified at 3' internucleotide
      bond

<400> SEQUENCE: 53
tcgtcgtttt gtcgttttgt cgtt                                             24

<210> SEQ ID NO 54
<211> LENGTH: 25
<212> TYPE: DNA
<213> ORGANISM: Artificial Sequence
<220> FEATURE:
<223> OTHER INFORMATION: synthetic construct

<400> SEQUENCE: 54
tcgcaacgtt tgcgacgtcg gtcga                                            25

<210> SEQ ID NO 55
<211> LENGTH: 25
<212> TYPE: DNA
<213> ORGANISM: Artificial Sequence
<220> FEATURE:
<223> OTHER INFORMATION: synthetic construct

<400> SEQUENCE: 55
tcgcaacgtt tgcgacggcg ctcga                                            25

<210> SEQ ID NO 56
<211> LENGTH: 25
<212> TYPE: DNA
<213> ORGANISM: Artificial Sequence
<220> FEATURE:
<223> OTHER INFORMATION: synthetic construct

<400> SEQUENCE: 56
tcgcaacgtt tgcgacgtcg ttcga                                            25

<210> SEQ ID NO 57
<211> LENGTH: 25
<212> TYPE: DNA
<213> ORGANISM: Artificial Sequence
<220> FEATURE:
<223> OTHER INFORMATION: synthetic construct
```

<400> SEQUENCE: 57
tcgcaacgtt tgcgacggcg ttcga                                    25

<210> SEQ ID NO 58
<211> LENGTH: 24
<212> TYPE: DNA
<213> ORGANISM: Artificial Sequence
<220> FEATURE:
<223> OTHER INFORMATION: synthetic construct

<400> SEQUENCE: 58
tcgcaacgtt tgcgacgtcg ttcg                                     24

<210> SEQ ID NO 59
<211> LENGTH: 25
<212> TYPE: DNA
<213> ORGANISM: Artificial Sequence
<220> FEATURE:
<223> OTHER INFORMATION: synthetic construct

<400> SEQUENCE: 59
tcgcaacgtt tgcgacgtcg ttcgg                                    25

<210> SEQ ID NO 60
<211> LENGTH: 25
<212> TYPE: DNA
<213> ORGANISM: Artificial Sequence
<220> FEATURE:
<223> OTHER INFORMATION: synthetic construct

<400> SEQUENCE: 60
tcgcaacgtt tacgacgtcg gtcga                                    25

<210> SEQ ID NO 61
<211> LENGTH: 25
<212> TYPE: DNA
<213> ORGANISM: Artificial Sequence
<220> FEATURE:
<223> OTHER INFORMATION: synthetic construct

<400> SEQUENCE: 61
tcgcaacgtt tacgacggcg ctcga                                    25

<210> SEQ ID NO 62
<211> LENGTH: 25
<212> TYPE: DNA
<213> ORGANISM: Artificial Sequence
<220> FEATURE:
<223> OTHER INFORMATION: synthetic construct

<400> SEQUENCE: 62
tcgcaacgtt tacgacgtcg ttcga                                    25

<210> SEQ ID NO 63
<211> LENGTH: 25
<212> TYPE: DNA
<213> ORGANISM: Artificial Sequence
<220> FEATURE:
<223> OTHER INFORMATION: synthetic construct

<400> SEQUENCE: 63
tcgcaacgtt tacgacggcg ttcga                                    25